(12) United States Patent
Naya et al.

(10) Patent No.: US 7,187,444 B2
(45) Date of Patent: Mar. 6, 2007

(54) MEASURING METHOD AND APPARATUS USING ATTENUATION IN TOTAL INTERNAL REFLECTION

(75) Inventors: Masayuki Naya, Kaisei-machi (JP); Mitsuru Sawano, Kaisei-machi (JP); Shu Sato, Kaisei-machi (JP); Toshihito Kimura, Kaisei-machi (JP); Hitoshi Shimizu, Kaisei-machi (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 10/291,566

(22) Filed: Nov. 12, 2002

(65) Prior Publication Data
US 2003/0090668 A1    May 15, 2003

(30) Foreign Application Priority Data

| Nov. 12, 2001 | (JP) | ............................. 2001-346217 |
| Mar. 13, 2002 | (JP) | ............................. 2002-068357 |
| Mar. 28, 2002 | (JP) | ............................. 2002-092282 |
| Mar. 29, 2002 | (JP) | ............................. 2002-095313 |
| Aug. 28, 2002 | (JP) | ............................. 2002-249680 |
| Aug. 30, 2002 | (JP) | ............................. 2002-254780 |

(51) Int. Cl.
*G01N 21/55* (2006.01)

(52) U.S. Cl. ............................................. 356/445

(58) Field of Classification Search .............. 356/445, 356/451, 453, 128; 250/339.01–339.15
See application file for complete search history.

(56) References Cited

U.S. PATENT DOCUMENTS

| 3,810,040 | A | * | 5/1974 | Martin et al. .................. 372/51 |
| 4,818,710 | A | * | 4/1989 | Sutherland et al. ......... 436/527 |
| 5,313,264 | A | | 5/1994 | Ivarsson et al. |
| 5,341,215 | A | * | 8/1994 | Seher .......................... 356/445 |
| 5,491,556 | A | * | 2/1996 | Stewart et al. ............... 356/445 |
| 5,923,031 | A | | 7/1999 | Naya |
| 6,330,062 | B1 | * | 12/2001 | Corn et al. .................. 356/445 |
| 6,493,097 | B1 | | 12/2002 | Ivarsson |
| 6,577,396 | B1 | | 6/2003 | Naya |
| 6,597,456 | B2 | * | 7/2003 | Kubo et al. .................. 356/445 |
| 6,667,807 | B2 | * | 12/2003 | Lieberman .................. 356/445 |

(Continued)

FOREIGN PATENT DOCUMENTS

EP       0 851 658 A2    7/1998

(Continued)

OTHER PUBLICATIONS

Takayuki Okamoto, "Spectral Research" Surface Refracto-Sensor Using Evanescent Waves: Principles and Instrumentations, vol. 47, No. 1, Dec. 8, 1998.

*Primary Examiner*—Michael P. Stafira
(74) *Attorney, Agent, or Firm*—Sughrue Mion, PLLC

(57) ABSTRACT

In a measuring method utilizing the phenomenon of attenuation in total internal reflection in which a light beam is caused to enter a dielectric block provided with a film layer to be brought into contact with a sample so that total internal reflection conditions are satisfied at the interface of the dielectric block and the film layer and various angles of incidence of the light beam to the interface of the dielectric block and the film layer can be obtained, and the intensity of the light beam reflected in total internal reflection at the interface is detected, the light beam is caused to intermittently impinge upon the dielectric block.

80 Claims, 34 Drawing Sheets

U.S. PATENT DOCUMENTS

| | | |
|---|---|---|
| 2002/0080358 A1 | 6/2002 | Shimizu |
| 2003/0189707 A1 | 10/2003 | Naya et al. |

FOREIGN PATENT DOCUMENTS

| | | |
|---|---|---|
| EP | 1 186 881 A1 | 3/2002 |
| JP | 59-061759 A | 4/1984 |
| JP | 6-167443 A | 6/1994 |
| JP | 11-051857 A | 2/1999 |
| JP | 11-326194 A | 11/1999 |
| JP | 2000-227360 A | 8/2000 |
| JP | 2001-255267 | 9/2001 |
| JP | 2001-330560 A | 11/2001 |
| JP | 2002-048707 A | 2/2002 |
| WO | WO 90/05295 A1 | 5/1990 |
| WO | WO 98/34098 A1 | 8/1998 |
| WO | WO 00/29830 | 5/2000 |

* cited by examiner

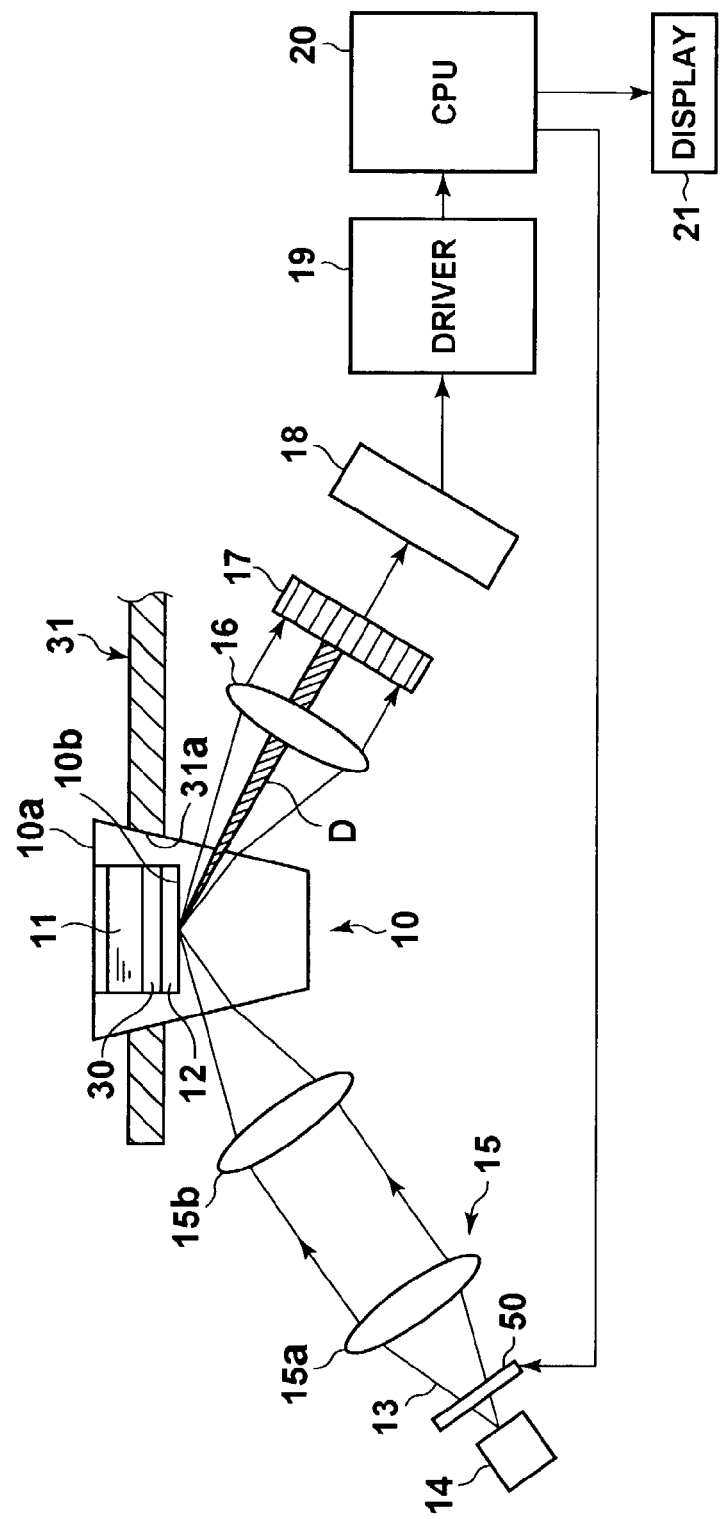

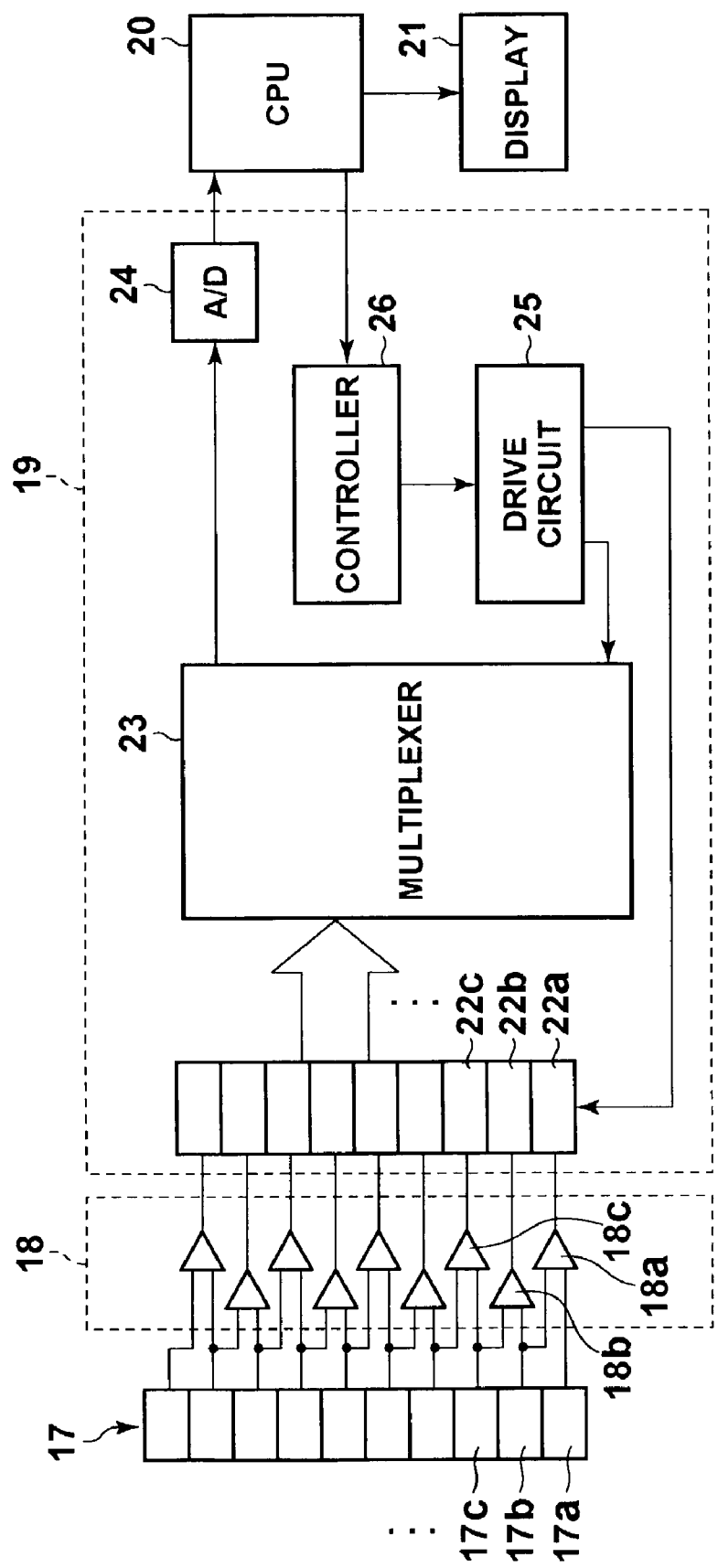

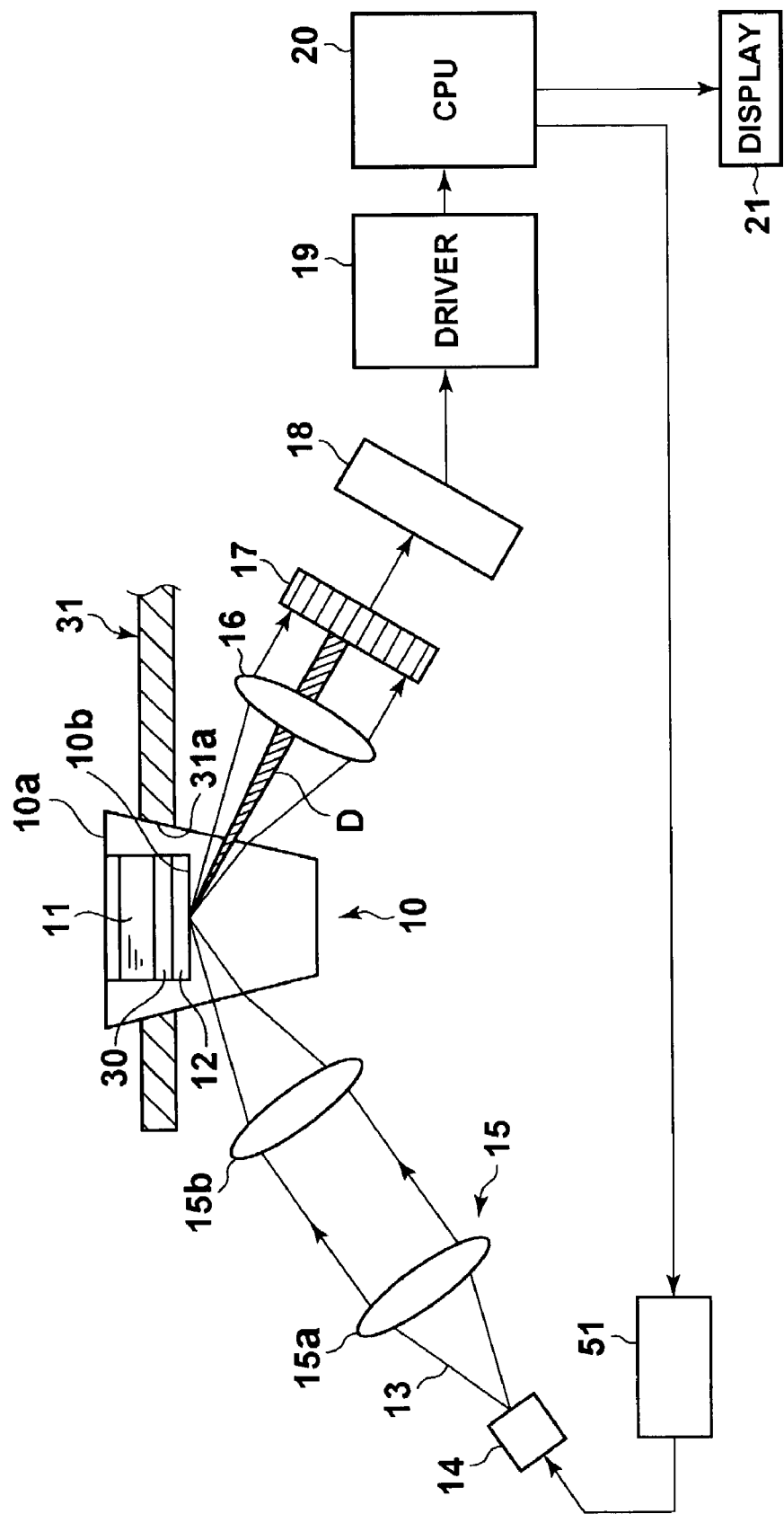

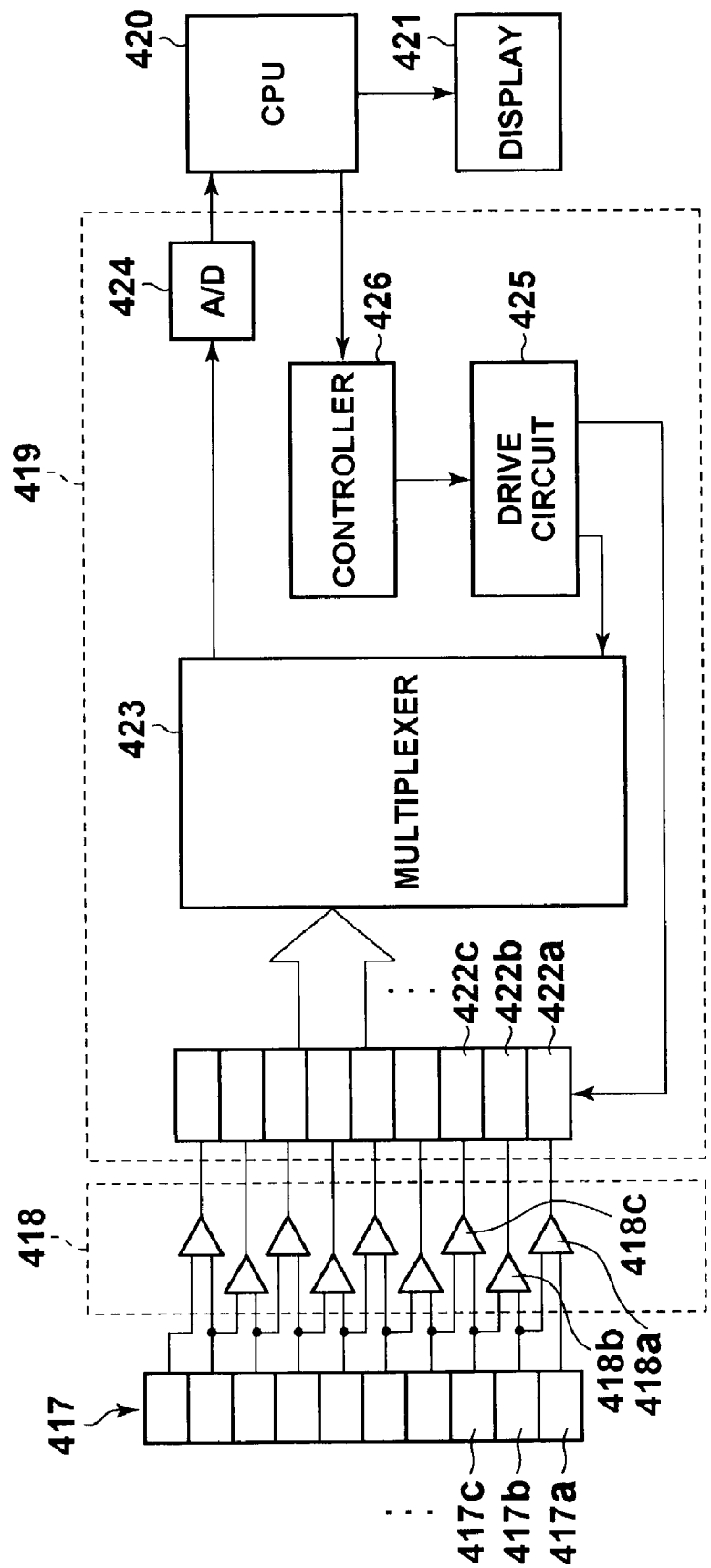

MEASURING METHOD AND APPARATUS USING ATTENUATION IN TOTAL INTERNAL REFLECTION

BACKGROUND OF THE INVENTION

1. Field of the Invention

This invention relates to a measuring method and apparatus using attenuation in total internal reflection such as a surface plasmon sensor for quantitatively analyzing a material in a sample on the basis of generation of surface plasmon, and more particularly to a measuring method and apparatus for measuring on the basis of generation of surface plasmon which is detected as a dark line in measuring light.

2. Description of the Related Art

In metal, free electrons vibrate in a group to generate compression waves called plasma waves. The compression waves generated in a metal surface are quantized into surface plasmon.

There have been proposed various surface plasmon sensors for quantitatively analyzing a material in a sample utilizing a phenomenon that such surface plasmon is excited by light waves. Among those, one employing a system called "Kretschmann configuration" is best known. See, for instance, Japanese Unexamined Patent Publication No. 6(1994)-167443.

The plasmon resonance sensor using the Kretschmann configuration basically comprises a dielectric block shaped, for instance, like a prism, a metal film which is formed on one face of the dielectric block and is brought into contact with a sample, a light source emitting a light beam, an optical system which causes the light beam to enter the dielectric block at various angles of incidence so that total internal reflection conditions are satisfied at the interface of the dielectric block and the metal film and various angles of incidence of the light beam to the interface of the dielectric block and the metal film including an angle of incidence at which attenuation in total internal reflection is generated due to surface plasmon resonance can be obtained, and a photodetector means which detects the intensity of the light beam reflected in total internal reflection at the interface and detects a state of surface plasmon resonance, i.e., a state of attenuation in total internal reflection.

In order to obtain various angles of incidence of the light beam to the interface, a relatively thin incident light beam may be caused to impinge upon the interface while deflecting the incident light beam or a relatively thick incident light beam may be caused to impinge upon the interface in the form of convergent light or divergent light so that components of the incident light beam impinge upon the interface at various angles. In the former case, the light beam which is reflected from the interface at an angle which varies as the incident light beam is deflected may be detected by a photodetector which is moved in synchronization with deflection of the incident light beam or by an area sensor extending in the direction in which reflected light beam is moved as a result of deflection. In the latter case, an area sensor which extends in directions so that all the components of light reflected from the interface at various angles can be detected by the area sensor may be used.

In such a plasmon resonance sensor, when a light beam impinges upon the interface at a particular angle of incidence θsp not smaller than the angle of total internal reflection, evanescent waves having an electric field distribution in the sample in contact with the metal film are generated and surface plasmon is excited in the interface between the metal film and the sample. When the wave vector of the evanescent waves is equal to the wave number of the surface plasmon and wave number matching is established, the evanescent waves and the surface plasmon resonate and light energy is transferred to the surface plasmon, whereby the intensity of light reflected in total internal reflection at the interface of the dielectric block and the metal film sharply drops. The sharp intensity drop is generally detected as a dark line by the photodetector.

The aforesaid resonance occurs only when the incident light beam is p-polarized. Accordingly, it is necessary to set the light beam to impinge upon the interface in the form of p-polarized light.

When the wave number of the surface plasmon can be known from the angle of incidence θsp at which the phenomenon of attenuation in total internal reflection (ATR) takes place, the dielectric constant of the sample can be obtained. That is, $$K_{sp}(\omega) = \frac{\omega}{c} \sqrt{\frac{\varepsilon_m(\omega)\varepsilon_s}{\varepsilon_m(\omega) + \varepsilon_s}}$$

wherein $K_{sp}$ represents the wave number of the surface plasmon, $\omega$ represents the angular frequency of the surface plasmon, c represents the speed of light in a vacuum, and $\varepsilon_m$ and $\varepsilon_s$ respectively represent the dielectric constants of the metal and the sample.

When the dielectric constant $\varepsilon_s$ of the sample is known, the concentration of a specific material in the sample can be determined on the basis of a predetermined calibration curve or the like. Accordingly, a property related to the dielectric constant (refractive index) of the sample can be detected by detecting the angle of incidence θsp at which the intensity of light reflected in total internal reflection from the interface of the prism and the metal film sharply drops (this angel θsp will be referred to as "the attenuation angle θsp", hereinbelow).

In such a surface plasmon sensor, it has been proposed, in order to measure the attenuation angle θsp accurately with a wide dynamic range, to use a photodetector in the form of an array of a plurality of photodetector elements arranged in a predetermined direction so that light beam components reflected at different angles at the interface impinge upon different photodetector elements as disclosed in Japanese Unexamined Patent Publication No. 11(1999)-326194.

In this case, the output signals output from the photodetector elements are generally differentiated in the direction in which the photodetector elements are arranged, and the refractive-index-related property of the material to be measured is generally obtained on the basis of the differentials.

As a similar apparatus utilizing the phenomenon of attenuation in total internal reflection (ATR), there has been known a leaky mode sensor described in, for instance, "Spectral Research" Vol.47, No.1 (1998), pp21 to 23 & pp26 and 27. The leaky mode sensor basically comprises a dielectric block shaped, for instance, like a prism, a clad layer which is formed on one face of the dielectric block, an optical waveguide layer which is formed on the clad layer and is brought into contact with a sample, a light source emitting a light beam, an optical system which causes the light beam to enter the dielectric block at various angles of incidence so that total internal reflection conditions are satisfied at the interface of the dielectric block and the clad layer and various angles of incidence of the light beam to the interface of the dielectric block and the clad layer including an angle of incidence at which attenuation in total internal reflection is generated due to optical waveguide mode excitation can be obtained, and a photodetector means which detects the intensity of the light beam reflected in total internal reflection at the interface and detects a state of waveguide mode excitation, i.e., a state of attenuation in total internal reflection (ATR).

In the leaky mode sensor with this arrangement, when the light beam is caused to impinge upon the clad layer through the dielectric block at an angle not smaller than an angle of total internal reflection, only light having a particular wave number and impinging upon the optical waveguide layer at a particular angle of incidence comes to propagate through the optical waveguide layer in a waveguide mode after passing through the clad layer. When the waveguide mode is thus excited, almost all the incident light is taken in the optical waveguide layer and accordingly, the intensity of light reflected in total internal reflection at the interface of the dielectric block and the clad layer sharply drops. That is, attenuation in total internal reflection occurs. Since the wave number of light to be propagated through the optical waveguide layer in a waveguide mode depends upon the refractive index of the sample on the optical waveguide layer, the refractive index and/or the properties of the sample related to the refractive index can be detected on the basis of the angle of incidence at which the attenuation in total internal reflection occurs.

Also in such a leaky mode sensor, a photodetector in the form of an array of a plurality of photodetector elements can be used to detect the position of the dark line generated due to the attenuation in total internal reflection, and at the same time differentiation of the output signals output from the photodetector elements is often applied.

The surface plasmon sensor and the leaky mode sensor are sometimes used in random screening for finding a specific material combined with a predetermined sensing material in the field of pharmacy. In this case, a sensing material is fixed on the film layer (the metal film in the case of the surface plasmon sensor and the clad layer and the optical waveguide layer in the case of the leaky mode sensor), and a sample liquid containing a material to be analyzed is spotted on the sensing material. Then the attenuation angle $\theta sp$ is repeatedly measured each time a predetermined time lapses.

When the sample material (the material to be analyzed in the sample liquid) is combined with the sensing material, the refractive index of the sensing material changes with time due to combination with the sample material. Accordingly, by measuring the attenuation angle $\theta sp$, at which attenuation in total internal reflection takes place, for every predetermined time, thereby detecting whether the attenuation angle $\theta sp$ changes (to know the state of combination of the sample material with the sensing material), it is possible to know whether the sample material is a specific material to be combined with the sensing material. As combinations of such a specific material and a sensing material, there have been known combinations of an antigen and an antibody and of an antibody and another antibody. For example, rabbit antihuman IgG antibody is fixed on the surface of the film layer as the sensing material with human IgG antibody employed as the specific material.

In order to detect the state of combination of the sample material with the sensing material, the total reflection attenuation angle $\theta sp$ (the angle of incidence $\theta sp$ at which attenuation in total internal reflection takes place) itself need not necessarily be detected. For example, the amount of change in the total reflection attenuation angle $\theta sp$ after the sample liquid is spotted onto the sensing material is measured and the state of combination of the sample material with the sensing material may be measured on the basis of the amount of change of the total reflection attenuation angle $\theta sp$. When a photodetector in the form of an array of a plurality of photodetector elements and differentiation of the output signals output from the photodetector elements are employed, the state of combination of the sample material with the sensing material can be measured on the basis of the amount of change of the differentiation of the output signals. (See our Japanese Patent Application No. 2000-398309.)

In the practical apparatuses utilizing the phenomenon of attenuation in total internal reflection such as a surface plasmon sensor or a leaky mode sensor, the amount of change of the total reflection attenuation angle $\theta sp$ is measured by spotting a sample liquid comprising solvent and a sample material onto a film layer formed on the bottom of a measuring chip in the form of a cup or dish.

This applicant has disclosed a measuring apparatus utilizing the phenomenon of attenuation in total internal reflection in which a plurality of measuring chips are placed on, for instance, a turn table and are measured in sequence, thereby shortening the time required to measure a lot of samples. (Japanese Unexamined Patent Publication No. 2001-330560)

Further, this applicant has disclosed a measuring apparatus utilizing the phenomenon of attenuation in total internal reflection in which measuring chips each having a plurality of sample liquid holding portion are used so that measurement on a plurality of samples can be done at one time without moving the measuring chips. (Japanese Patent Application No. 2001-397411)

In measuring apparatuses utilizing the phenomenon of attenuation in total internal reflection, it is necessary to keep constant the environmental temperature throughout measurement since the refractive index of the sample is changed depending on the temperature around the dielectric block.

However, since the dielectric block is kept exposed to a light beam, the temperature around the dielectric block is raised, which changes the refractive index of the sample and causes drift of the detecting signal.

Further, when the film layer (the metal film in the case of the surface plasmon sensor and the clad layer and the optical waveguide layer in the case of the leaky mode sensor) is non-uniform in thickness, or the sensing material fixed on the film layer is non-uniform in reactivity, or when dust adhere to the film layer, the result of measurement can fluctuate according to the position where the light beam impinges upon the interface. The sensing material described above is discussed in detail, for instance, in our Japanese Patent Application 2001-113647.

The problem of fluctuation in the result of measurement may be overcome by causing the light beam to impinge upon the interface between the film layer and the dielectric block not to be focused thereon as disclosed in Japanese Patent Application 2000-149415. That is, when the light beam impinges upon the interface over an area of a certain width, measurement can be done under a condition where the thickness of the film layer, the reactivity of the sensing material and the like are averaged and fluctuation in the result of measurement can be suppressed.

However, when the light beam is not focused on the interface and impinges upon the interface over an area of a certain width, the range of angle of incidence of the light beam at which the attenuation in total internal reflection takes place is widened and the measuring sensitivity deteriorates.

Further, the problem of fluctuation in the result of measurement may be overcome by preparing a plurality of measuring units, each comprising a dielectric block and a film layer, for one sample, and carrying out measurement on one sample a plurality of times using different measuring units, and statistically processing the results of measurement. However, this approach is disadvantageous in that it takes a long time to obtain result of measurement for one sample.

Further in the case where a photodetector in the form of an array of a plurality of photodetector elements arranged in a predetermined direction is employed to detect the position of a dark line as disclosed in Japanese Unexamined Patent Publication No. 11(1999)-326194, the output characteristics versus the position of the dark line becomes non-linear and it becomes difficult to perform exact measurement when the photodetector elements of the photodetector are not uniform in sensitivity or the sensitivity characteristics of the photodetector elements are non-linear.

Conventionally, the intensity of the light beam reflected at the interface is generally detected by a photodetector which is moved in synchronization with deflection of the light beam or an area sensor such as a CCD having a large light receiving face. However, the former is disadvantageous in that since it requires a mechanical drive mechanism, it is not suitable for analyzing samples at high speed though a wide dynamic range can be ensured with respect to the measuring range of the attenuation angle θsp, whereas the latter is disadvantageous in that since the area sensor is low in resolution and dynamic range for charge accumulation, it is difficult to ensure high analyzing accuracy though being suitable for analyzing samples at high speed.

In order to avoid the difficulties described above, we, this applicant, have proposed a measuring apparatus in which the intensity of the light beam reflected at the interface is detected by a photodetector means comprising a plurality of photodetector elements, the outputs of adjacent pairs of photodetector elements of the photodetector means are differentiated and the attenuation angle θsp is obtained on the basis of the differentials as disclosed, for instance, in Japanese Unexamined Patent Publication No. 11(1999)-326194. This apparatus can detect the attenuation angle θsp more accurately with a wider dynamic range as compared with area sensors like a CCD.

Recently, there has been a demand in apparatuses such as that disclosed in Japanese Unexamined Patent Publication No. 11(1999)-326194 that the profile of the light beam detected by the photodetector means is to be known. However, in such a measuring apparatus, each of the photodetector elements is large in size in order to increase the output signal of the photodetector element. That is, the photodetector elements are arranged at rough pitches, which results in low resolution of the beam profile.

Whereas when the photodetector elements are arranged at fine pitches in order to detect the beam profile in a high resolution, the output signal of each photodetector element becomes too weak to accurately obtain the attenuation angle θsp. Further, when the amount of light received by each photodetector element is small, influence of noise is strengthened.

SUMMARY OF THE INVENTION

In view of the foregoing observations and description, the primary object of the present, invention is to provide a measuring method and apparatus using attenuation in total internal reflection in which drift of the detecting signal is prevented.

Another object of the present invention is to provide a measuring apparatus in which fluctuation in the result of measurement due to non-uniformity of the thickness of the film layer and/or the reactivity of the sensing material and due to dust adhering to the film layer can be prevented and which can efficiently effect measurement at a high sensitivity.

Still another object of the present invention is to provide a measuring method and apparatus for detecting the position of a dark line by the use of a plurality of photodetector elements in which measuring error due to difference in sensitivity between the photodetector elements can be suppressed, whereby the measuring accuracy is improved.

Still another object of the present invention is to provide a measuring method and apparatus in which the intensity of the light beam reflected at the interface is detected by a plurality of photodetector elements, the outputs of adjacent pairs of photodetector elements of the photodetector means are differentiated and the attenuation angle θsp is detected on the basis of the differentials and which is improved so that the attenuation angle θsp can be accurately detected and the beam profile can be detected at high resolution.

In accordance with a first aspect of the present invention, there is provided a measuring method utilizing the phenomenon of attenuation in total internal reflection in which a light beam is caused to enter a dielectric block provided on one face thereof with a film layer to be brought into contact with a sample so that total internal reflection conditions are satisfied at the interface of the dielectric block and the film layer and various angles of incidence of the light beam to the interface of the dielectric block and the film layer can be obtained, and the intensity of the light beam reflected in total internal reflection at the interface is detected thereby detecting a state of attenuation in total internal reflection, wherein the improvement comprises the step of causing said light beam to intermittently impinge upon the dielectric block, thereby preventing temperature fluctuation of the dielectric block.

In accordance with a second aspect of the present invention, there is provided a measuring method utilizing the phenomenon of attenuation in total internal reflection in which a light beam is caused to enter a dielectric block provided on its face with a metal film to be brought into contact with a sample so that total internal reflection conditions are satisfied at the interface of the dielectric block and the metal film and various angles of incidence of the light beam to the interface of the dielectric block and the metal film can be obtained, and the intensity of the light beam reflected in total internal reflection at the interface is detected thereby detecting a state of attenuation in total internal reflection involved by surface plasmon resonance, wherein the improvement comprises the step of causing said light beam to intermittently impinge upon the dielectric block, thereby preventing temperature fluctuation of the dielectric block.

In accordance with a third aspect of the present invention, there is provided a measuring method utilizing the phenomenon of attenuation in total internal reflection in which a light beam is caused to enter a dielectric block provided on its face with a clad layer and on the clad layer with an optical waveguide layer to be brought into contact with a sample so that total internal reflection conditions are satisfied at the interface of the dielectric block and the clad layer and various angles of incidence of the light beam to the interface of the dielectric block and the clad layer can be obtained, and the intensity of the light beam reflected in total internal reflection at the interface is detected thereby detecting a state of attenuation in total internal reflection involved by waveguide mode excitation on the optical waveguide layer, wherein the improvement comprises the step of causing said light beam to intermittently impinge upon the dielectric block, thereby preventing temperature fluctuation of the dielectric block.

In the methods in accordance with the first to third aspects of the present invention, it is preferred that measurement be started after a lapse of a transient response time from initiation of the light beam impinging upon the dielectric block, the transient response time being a time required for the light beam detecting signal (representing the intensity of the light beam reflected in total internal reflection at the interface) to become substantially constant from initiation of the light beam impinging upon the dielectric block.

In accordance with a fourth aspect of the present invention, there is provided a measuring apparatus for carrying out the measuring method in accordance with the first aspect of the present invention. That is, the measuring apparatus in accordance with the fourth aspect of the present invention comprises a dielectric block, a film layer which is formed on one face of the dielectric block and is brought into contact with a sample, a light source which emits a light beam, an optical system which causes the light beam to enter the dielectric block so that total internal reflection conditions are satisfied at the interface of the dielectric block and the film layer and various angles of incidence of the light beam to the interface of the dielectric block and the film layer can be obtained, and a photodetector means which detects the intensity of the light beam reflected in total internal reflection at the interface, thereby detecting a state of attenuation in total internal reflection, wherein the improvement comprises an intermittent light beam projecting means which causes said light beam to intermittently impinge upon the dielectric block.

In accordance with a fifth aspect of the present invention, there is provided a measuring apparatus for carrying out the measuring method in accordance with the second aspect of the present invention. That is, the measuring apparatus in accordance with the fifth aspect of the present invention comprises a dielectric block, a metal film which is formed on one face of the dielectric block and is brought into contact with a sample, a light source which emits a light beam, an optical system which causes the light beam to enter the dielectric block so that total internal reflection conditions are satisfied at the interface of the dielectric block and the metal film and various angles of incidence of the light beam to the interface of the dielectric block and the metal film can be obtained, and a photodetector means which detects the intensity of the light beam reflected in total internal reflection at the interface, thereby detecting a state of attenuation in total internal reflection, wherein the improvement comprises an intermittent light beam projecting means which causes said light beam to intermittently impinge upon the dielectric block.

In accordance with a sixth aspect of the present invention, there is provided a measuring apparatus for carrying out the measuring method in accordance with the third aspect of the present invention. That is, the measuring apparatus in accordance with the sixth aspect of the present invention comprises a dielectric block, a clad layer which is formed on one face of the dielectric block, an optical waveguide layer which is formed on the clad layer and is brought into contact with a sample, a light source which emits a light beam, an optical system which causes the light beam to enter the dielectric block so that total internal reflection conditions are satisfied at the interface of the dielectric block and the clad layer and various angles of incidence of the light beam to the interface of the dielectric block and the clad layer can be obtained, and a photodetector means which detects the intensity of the light beam reflected in total internal reflection at the interface, thereby detecting a state of attenuation in total internal reflection, wherein the improvement comprises an intermittent light beam projecting means which causes said light beam to intermittently impinge upon the dielectric block.

In the measuring apparatuses in accordance with fourth to sixth aspects of the present invention, the intermittent light beam projecting means may comprise, for instance, a shutter means which intermittently closes and opens the path of the light beam from the light source to the dielectric block, or an intermittent light source drive means which intermittently drives the light source. When an intermittent light source drive means is employed as the intermittent light beam projecting means, it is preferred that the intermittent light source drive means be provided with a wavelength stabilizing means which stabilizes the wavelength of the light beam emitted from the light source.

Since typical solvent employed in the measurement is $4.5 \times 110^{-4}$ in the ratio of change of the refractive index to change of the temperature (dn/dt), it is necessary to suppress change of the temperature to not larger than 1° C. in order to suppress change of the refractive index to not larger than $110^{-4}$.

For this purpose, the intermittent light projecting means is arranged to cause the light beam to impinge upon the dielectric block so that change of the temperature due to projection of the light beam onto the dielectric block is suppressed preferably to not larger than 0.5° C. and more preferably to not larger than 0.1° C.

Further, it is preferred that the photodetector means starts measurement after a lapse of a transient response time from initiation of the light beam impinging upon the dielectric block.

In the methods and apparatuses in accordance with the first to sixth aspects of the present invention, since the light beam is caused to intermittently impinge upon the dielectric block, whereby the time for which the light beam impinges upon the dielectric block is shortened, change of temperature of the sample and change of temperature of the dielectric block which affect the sample are suppressed and accordingly, drift of the detecting signal is prevented.

In accordance with a seventh aspect of the present invention, there is provided a measuring apparatus comprising a dielectric block, a film layer which is formed on one face of the dielectric block and is brought into contact with a sample, a light source which emits a light beam, an optical system which causes the light beam to enter the dielectric block at an angle of incidence such that total internal reflection conditions are satisfied at the interface of the dielectric block and the film layer, and a photodetector means which detects the intensity of the light beam reflected in total internal reflection at the interface, wherein the improvement comprises a relative movement means which moves the optical system and the dielectric block relatively to each other so that the position in which the light beam impinges upon the interface changes, and an operation means which statistically processes a plurality of pieces of data, which are output from the photodetector means when the optical system and the dielectric block are in different positions relatively to each other and represent the intensities of the light beam reflected in the different positions of the interface, and obtains data representative of the intensities of the light beam reflected at the interface.

In accordance with an eighth aspect of the present invention, there is provided a measuring apparatus comprising a dielectric block, a metal film which is formed on one face of the dielectric block and is brought into contact with a sample, a light source which emits a light beam, an optical system which causes the light beam to enter the dielectric block at an angle of incidence such that total internal reflection conditions are satisfied at the interface of the dielectric block and the metal film, and a photodetector means which detects the intensity of the light beam reflected in total internal reflection at the interface, wherein the improvement comprises a relative movement means and an operation means which are equivalent to those of the measuring system in accordance with the seventh aspect of the present invention.

In accordance with a ninth aspect of the present invention, there is provided a measuring apparatus comprising a dielectric block, a film layer consisting of a clad layer formed on one face of the dielectric block and an optical waveguide layer which is formed on the clad layer and is brought into contact with a sample, a light source which emits a light beam, an optical system which causes the light beam to enter the dielectric block at an angle of incidence such that total internal reflection conditions are satisfied at the interface of the dielectric block and the clad layer, and a photodetector means which detects the intensity of the light beam reflected in total internal reflection at the interface, wherein the improvement comprises a relative movement means and an operation means which are equivalent to those of the measuring system in accordance with the seventh aspect of the present invention.

The position in which the light beam impinges upon the interface may be changed, instead of employing a relative movement means which moves the optical system and the dielectric block relatively to each other, by specially structuring the optical system. That is, in accordance with a tenth aspect of the present invention, there is provided a measuring apparatus comprising a dielectric block, a film layer which is formed on one face of the dielectric block and is brought into contact with a sample, a light source which emits a light beam, an optical system which causes the light beam to enter the dielectric block at an angle of incidence such that total internal reflection conditions are satisfied at the interface of the dielectric block and the film layer, and a photodetector means which detects the intensity of the light beam reflected in total internal reflection at the interface, wherein the improvement comprises that the optical system is arranged to be able to cause the light beam to impinge upon the interface in a plurality of different positions, and there is provided an operation means which is equivalent to those of the measuring system in accordance with the seventh aspect of the present invention.

In accordance with an eleventh aspect of the present invention, there is provided a measuring apparatus comprising a dielectric block, a metal film which is formed on one face of the dielectric block and is brought into contact with a sample, a light source which emits a light beam, an optical system which causes the light beam to enter the dielectric block at an angle of incidence such that total internal reflection conditions are satisfied at the interface of the dielectric block and the metal film, and a photodetector means which detects the intensity of the light beam reflected in total internal reflection at the interface, wherein the improvement comprises that the optical system is arranged to be able to cause the light beam to impinge upon the interface in a plurality of different positions, and there is provided an operation means which is equivalent to those of the measuring system in accordance with the seventh aspect of the present invention.

In accordance with a twelfth aspect of the present invention, there is provided a measuring apparatus comprising a dielectric block, a film layer consisting of a clad layer formed on one face of the dielectric block and an optical waveguide layer which is formed on the clad layer and is brought into contact with a sample, a light source which emits a light beam, an optical system which causes the light beam to enter the dielectric block at an angle of incidence such that total internal reflection conditions are satisfied at the interface of the dielectric block and the clad layer, and a photodetector means which detects the intensity of the light beam reflected in total internal reflection at the interface, wherein the improvement comprises that the optical system is arranged to be able to cause the light beam to impinge upon the interface in a plurality of different positions, and there is provided an operation means which is equivalent to those of the measuring system in accordance with the seventh aspect of the present invention.

In the measuring apparatuses of the seventh to twelfth aspects of the present invention, the sample may be analyzed in various ways on the basis of the intensity of the light beam reflected in total internal reflection at the interface. For example, the sample may be analyzed by detecting the position (angle) of a dark line generated by attenuation in total internal reflection by causing the light beam to impinge upon the interface so that total internal reflection conditions are satisfied at the interface and various angles of incidence of the light beam to the interface are obtained, and measuring the intensity of the light beam reflected in total internal reflection at the interface by positions corresponding to angles of incidence, or by causing a plurality of light beams having different wavelengths to impinge upon the interface so that total internal reflection conditions are satisfied at the interface, measuring the intensities of the light beams reflected in total internal reflection at the interface by wavelengths and detecting the degree of attenuation in total internal reflection by wavelengths as disclosed in "Porous Gold in Surface Plasmon Resonance Measurement" by D. V. Noort, K. Johansen, and C. F. Mandenius (EUROSENSORS XIII, 1999, pp.585–588).

Further, the sample may be analyzed by causing a light beam to impinge upon the interface so that total internal reflection conditions are satisfied at the interface, splitting a part of the light beam before impinging upon the interface, causing the part of the light beam to interfere with the light beam reflected in total internal reflection at the interface, and measuring the intensity of the light beam after the interference as disclosed in "Surface Plasmon Resonance Interferometry for Micro-Array Biosensing" by P. I. Nikitin, A. N. Grigorenko, A. A. Beloglazov, M. V. Valeico, A. I. Savchuk, and O. A. Savchuk (EUROSENSORS XIII, 1999, pp.235–238).

The optical system employed in the measuring apparatuses in accordance with the tenth to twelfth aspects of the present invention may be, for instance, an optical system which splits a light beam into a plurality of light beams and causes the light beams to impinge upon the interface in different positions or an optical system which deflects a light beam to impinge upon the interface in different positions.

The operation means employed in the measuring apparatuses in accordance with the seventh to twelfth aspects of the present invention may be, for instance, a means which takes a median of the plurality of pieces of data, which represent the intensities of the light beam reflected in the different positions of the interface, as data representative of the intensities of the light beam reflected at the interface.

Further, the operation means employed in the measuring apparatuses in accordance with the seventh to twelfth aspects of the present invention may be a means which takes a median of the plurality of pieces of data, which represent the intensities of the light beam reflected in the different positions of the interface, and obtains an average of the data included in a range of a predetermined width including the median as data representative of the intensities of the light beam reflected at the interface.

Further, the operation means employed in the measuring apparatuses in accordance with the seventh to twelfth aspects of the present invention may be a means which takes an average of the plurality of pieces of data, which represent the intensities of the light beam reflected in the different positions of the interface, minus the maximum value and the minimum value as data representative of the intensities of the light beam reflected at the interface.

In the apparatuses in accordance with the seventh to twelfth aspects of the present invention, since data representative of the intensities of the light beam reflected at the interface is obtained by statistically processing a plurality of pieces of data, which are output from the photodetector means when the optical system and the dielectric block are in different positions relatively to each other and represent the intensities of the light beam reflected in the different positions of the interface, fluctuation in the result of measurement due to non-uniformity of the thickness of the film layer and/or the reactivity of the sensing material and due to dust adhering to the film layer can be prevented.

Further since it is not necessary to cause the light beam to impinge upon the interface not to be focused thereon, the range of angle of incidence of the light beam at which the attenuation in total internal reflection is observed is not widened and the measuring sensitivity does not deteriorate.

Further, in accordance with the seventh to twelfth aspects of the present invention, fluctuation of the result of measurement can be prevented by the use of only a single measuring unit (comprising a dielectric block and a film layer), and accordingly, the time required to supply the sample and carry out the measuring process can be shortened and measurement can be done more efficiently as compared with the case where measurement on one sample is done by the use of a plurality of measuring units.

In accordance with a thirteenth aspect of the present invention, there is provided a measuring method for analyzing a sample by the use of a measuring apparatus comprising a measuring chip consisting of a dielectric block, a film layer formed on one face of the dielectric block and a sample holding system which holds the sample on the surface of the film layer, a light source which emits a light beam, an optical system which causes the light beam to enter the dielectric block at an angle of incidence such that total internal reflection conditions are satisfied at the interface of the dielectric block and the film layer, and a photodetector means which comprises a plurality of photodetector elements and detects the intensity of the light beam reflected in total internal reflection at the interface, wherein the improvement comprises the steps of measuring the intensity of the light beam reflected in total internal reflection at the interface a plurality of times in a time series, smoothing a plurality of pieces of measured data obtained and analyzing the sample on the basis of the smoothed pieces of measured data.

In accordance with a fourteenth aspect of the present invention, there is provided a measuring apparatus comprising a measuring chip consisting of a dielectric block, a film layer formed on one face of the dielectric block and a sample holding system which holds the sample on the surface of the film layer, a light source which emits a light beam, an optical system which causes the light beam to enter the dielectric block at an angle of incidence such that total internal reflection conditions are satisfied at the interface of the dielectric block and the film layer, and a photodetector means which comprises a plurality of photodetector elements and detects the intensity of the light beam reflected in total internal reflection at the interface, wherein the improvement comprises a smoothing means which smoothes a plurality of pieces of measured data obtained by measuring the intensity of the light beam reflected in total internal reflection at the interface a plurality of times in a time series.

The measuring apparatus may be in the form of, for instance, a surface plasmon sensor where the film layer is of a metal film or a leaky mode sensor where the film layer consists of a clad layer formed on one face of the dielectric block and an optical waveguide layer formed on the clad layer.

In the measuring method and apparatus of the thirteenth and fourteenth aspects of the present invention, the sample may be analyzed in various ways on the basis of the intensity of the light beam reflected in total internal reflection at the interface. For example, the sample may be analyzed by detecting the position (angle) of a dark line generated by attenuation in total internal reflection by causing the light beam to impinge upon the interface so that total internal reflection conditions are satisfied at the interface and various angles of incidence of the light beam to the interface are obtained, and measuring the intensity of the light beam reflected in total internal reflection at the interface by positions corresponding to angles of incidence, or by causing a plurality of light beams having different wavelengths to impinge upon the interface so that total internal reflection conditions are satisfied at the interface, measuring the intensities of the light beams reflected in total internal reflection at the interface by wavelengths and detecting the degree of attenuation in total internal (position and degree of the dark line) reflection by wavelengths as disclosed in "Porous Gold in Surface Plasmon Resonance Measurement" by D. V. Noort, K. Johansen, and C. F. Mandenius (EUROSENSORS XIII, 1999, pp.585–588).

In the measuring method and apparatus of the thirteenth and fourteenth aspects of the present invention, "smoothing" is a process for suppressing measuring errors due to sensitivities of the respective photodetector elements. The measuring errors may be suppressed by reducing the difference between the measured data and an estimated true value by a least square method, or by cutting redundant frequency components from output signals continuously output from the photodetector means by the use of a frequency filter such as a low-pass filter, a high-pass filter or a band-pass filter.

The expression "a plurality of pieces of measured data obtained by measuring a plurality of times in a time series" should be broadly interpreted to include not only pieces of data obtained by intermittent measurement but also pieces of data obtained by continuous measurement for a predetermined time interval.

In the method and apparatus in accordance with the thirteenth and fourteenth aspects of the present invention, since a plurality of pieces of measured data obtained are smoothed and the sample is analyzed on the basis of the smoothed pieces of measured data, measuring errors due to sensitivities of the respective photodetector elements are suppressed and the measuring accuracy is improved.

In accordance with a fifteenth aspect of the present invention, there is provided a measuring method for analyzing a sample by the use of a measuring apparatus comprising a measuring chip consisting of a dielectric block, a film layer formed on one face of the dielectric block and a sample holding system which holds the sample on the surface of the film layer, a light source which emits a light beam, an optical system which causes the light beam to enter the dielectric block at an angle of incidence such that total internal reflection conditions are satisfied at the interface of the dielectric block and the film layer, and a photodetector means which comprises a plurality of photodetector elements and detects the intensity of the light beam reflected in total internal reflection at the interface, wherein the improvement comprises the steps of dividing the plurality of photodetector elements into a plurality of groups, differentiating the sums of the outputs of the photodetector elements in adjacent two groups in the direction in which the photodetector elements are arranged and analyzing the sample by obtaining an angle of reflection at which the intensity of the light reflected at the interface takes an absolute minimum on the basis of the differentials.

In accordance with a sixteenth aspect of the present invention, there is provided a measuring method for analyzing a sample by the use of a measuring apparatus comprising a measuring chip consisting of a dielectric block, a film layer formed on one face of the dielectric block and a sample holding system which holds the sample on the surface of the film layer, a light source which emits a light beam, an optical system which causes the light beam to enter the dielectric block at an angle of incidence such that total internal reflection conditions are satisfied at the interface of the dielectric block and the film layer, and a photodetector means which comprises a plurality of photodetector elements and detects the intensity of the light beam reflected in total internal reflection at the interface, wherein the improvement comprises the steps of calculating averages of outputs of a predetermined number of adjacent photodetector elements in sequence in the direction in which the photodetector elements are arranged, differentiating the averages in the direction in which the photodetector elements are arranged and analyzing the sample by obtaining an angle of reflection at which the intensity of the light reflected at the interface takes an absolute minimum on the basis of the differentials.

In accordance with a seventeenth aspect of the present invention, there is provided a measuring apparatus comprising a measuring chip consisting of a dielectric block, a film layer formed on one face of the dielectric block and a sample holding system which holds the sample on the surface of the film layer, a light source which emits a light beam, an optical system which causes the light beam to enter the dielectric block at an angle of incidence such that total internal reflection conditions are satisfied at the interface of the dielectric block and the film layer, and a photodetector means which comprises a plurality of photodetector elements and detects the intensity of the light beam reflected in total internal reflection at the interface, wherein the improvement comprises, an operation means which divides the plurality of photodetector elements into a plurality of groups, differentiates the sums of the outputs of the photodetector elements in adjacent two groups in the direction in which the photodetector elements are arranged and obtains an angle of reflection at which the intensity of the light reflected at the interface takes an absolute minimum on the basis of the differentials.

In accordance with a eighteenth aspect of the present invention, there is provided a measuring apparatus comprising a measuring chip consisting of a dielectric block, a film layer formed on one face of the dielectric block and a sample holding system which holds the sample on the surface of the film layer, a light source which emits a light beam, an optical system which causes the light beam to enter the dielectric block at an angle of incidence such that total internal reflection conditions are satisfied at the interface of the dielectric block and the film layer, and a photodetector means which comprises a plurality of photodetector elements and detects the intensity of the light beam reflected in total internal reflection at the interface, wherein the improvement comprises an operation means which calculates averages of outputs of a predetermined number of adjacent photodetector elements in sequence in the direction in which the photodetector elements are arranged, differentiates the averages in the direction in which the photodetector elements are arranged and obtains an angle of reflection at which the intensity of the light reflected at the interface takes an absolute minimum on the basis of the differentials.

The measuring apparatus may be in the form of, for instance, a surface plasmon sensor where the film layer is of a metal film or a leaky mode sensor where the film layer consists of a clad layer formed on one face of the dielectric block and an optical waveguide layer formed on the clad layer.

In the measuring method and apparatus of the fifteenth to eighteenth aspects of the present invention, the sample may be analyzed in various ways on the basis of the intensity of the light beam reflected in total internal reflection at the interface. For example, the sample may be analyzed by detecting the position (angle) of a dark line generated by attenuation in total internal reflection by causing the light beam to impinge upon the interface so that total internal reflection conditions are satisfied at the interface and various angles of incidence of the light beam to the interface are obtained, and measuring the intensity of the light beam reflected in total internal reflection at the interface by positions corresponding to angles of incidence, or by causing a plurality of light beams having different wavelengths to impinge upon the interface so that total internal reflection conditions are satisfied at the interface, measuring the intensities of the light beams reflected in total internal reflection at the interface by wavelengths and detecting the degree of attenuation in total internal reflection (position and degree of the dark line) by wavelengths as disclosed in "Porous Gold in Surface Plasmon Resonance Measurement" by D. V. Noort, K. Johansen, and C. F. Mandenius (EUROSENSORS XIII, 1999, pp.585–588).

In the measuring method and apparatus of the fifteenth and seventeenth aspects of the present invention, the expression "dividing the plurality of photodetector elements into a plurality of groups and differentiating the sums of the outputs of the photodetector elements in adjacent two groups in the direction in which the photodetector elements are arranged" means not only the case where the sums of the outputs of the photodetector elements in adjacent two groups are obtained and the sums are differentiated in the direction in which the photodetector elements are arranged but also the case where the outputs of two photodetector elements respectively in adjacent two groups are first differentiated in the direction in which the photodetector elements are arranged and then the differentials are summed. That is, any process of calculation may be employed so long as the same differential values are obtained.

For example, assuming that the photodetector means comprises first to sixth photodetector elements and the six photodetector elements are divided into a first group consisting of the first to third photodetector elements and second group consisting of the fourth to sixth photodetector elements, the outputs of the first to third photodetector elements in the first group may be summed while the outputs of the fourth to sixth photodetector elements in the second group are summed, and the sum of the outputs of the first to third photodetector elements in the first group and the sum of the outputs of the fourth to sixth photodetector elements in the second group may be differentiated in the direction in which the photodetector elements are arranged, or the output of the first photodetector element in the first group and the output of the fourth photodetector element in the second group may be first differentiated in the direction in which the photodetector elements are arranged as well as the output of the second photodetector element in the first group and the output of the fifth photodetector element in the second group and the output of the third photodetector element in the first group and the output of the sixth photodetector element in the second group and then the differentials may be summed. Otherwise, the difference between the output of the first photodetector element in the first group and the output of the sixth photodetector element in the second group, the difference between the output of the second photodetector element in the first group and the output of the fifth photodetector element in the second group and the difference between the output of the third photodetector element in the first group and the output of the fourth photodetector element in the second group may be summed and the sum may be divided by the distance between the groups, i.e., in this particular example, the distance corresponding to three photodetector elements.

In the measuring method and apparatus of the sixteenth and eighteenth aspects of the present invention, the expression "calculating averages of outputs of a predetermined number of adjacent photodetector elements in sequence in the direction in which the photodetector elements are arranged and differentiating the averages in the direction in which the photodetector elements are arranged" means not only the case where averages of outputs of a predetermined number of adjacent photodetector elements in sequence in the direction in which the photodetector elements are arranged are obtained and the averages are differentiated in the direction in which the photodetector elements are arranged but also the case where the outputs of adjacent two photodetector elements are first differentiated in the direction in which the photodetector elements are arranged and then the differentials for a predetermined number of photodetector elements are averaged. That is, any process of calculation may be employed so long as the same differential values are obtained.

For example, assuming that the photodetector means comprises first to fourth photodetector elements, averages of outputs of three adjacent photodetector elements are calculated in sequence in the direction in which the photodetector elements are arranged and differentiating the averages in the direction in which the photodetector elements are arranged, the average of the outputs of the first to third photodetector elements and the average of the outputs of the second to fourth photodetector elements may be first calculated and the averages may be differentiated in the direction in which the photodetector elements are arranged, or the outputs of the first and second photodetector elements may be differentiated in the direction in which the photodetector elements are arranged as well as the outputs of the second photodetector element and the third photodetector element and the outputs of the third photodetector element and the fourth photodetector element and then the differentials maybe averaged. Further, the "average, of outputs of a predetermined number of adjacent photodetector elements" need not be an average itself but may be any value so long as it reflects the average. For example, a value corresponding to the sum of the outputs of the predetermined number of photodetector elements or a value obtained by dividing or multiplying the sum of the outputs of the predetermined number of photodetector elements by a certain value may be employed as the average.

Further, the "angle of reflection at which the intensity of the light reflected at the interface takes an absolute minimum" need not be an angle of reflection at which the intensity of the light reflected at the interface takes an absolute minimum itself but may be any value so long as it reflects the angle of reflection at which the intensity of the light reflected at the interface takes an absolute minimum. For example, an angle reflection close to the angle of reflection at which the intensity of the light reflected at the interface takes an absolute minimum may be employed. The "absolute minimum" should be an absolute minimum generated by attenuation in total internal reflection and does not include an absolute minimum generated by noise or the like.

In the measuring method and apparatus of the fifteenth and seventeenth aspects of the present invention, since the outputs of a plurality of photodetector elements are summed and the sums are differentiated, the signals to be differentiated are sufficiently large in output even if each photodetector element is small in size and accordingly, the photodetector elements can be arranged at fines pitches, which allows to obtain a beam profile in high resolution and to accurately calculate the attenuation angle θsp.

In the measuring method and apparatus of the sixteenth and eighteenth aspects of the present invention, since the outputs of a plurality of photodetector elements are averaged and the averages are differentiated, detection of the attenuation angle θsp is less apt to be affected by noise and the attenuation angle θsp can be accurately detected even if each photodetector element is small in size and the amount of light received by each photodetector element is small. Further since the same number of averages as the number of the photodetector elements can be calculated, the attenuation angle θsp can be obtained in high resolution and the beam profile can be obtained in high resolution.

The methods and apparatuses in accordance with the present invention may be variously combined. For example, in accordance with a nineteenth aspect of the present invention, there is provided a measuring method for analyzing a sample by the use of a measuring apparatus comprising a measuring chip consisting of a dielectric block, a film layer formed on one face of the dielectric block and a sample holding system which holds the sample on the surface of the film layer, a light source which emits a light beam, an optical system which causes the light beam to enter the dielectric block at an angle of incidence such that total internal reflection conditions are satisfied at the interface of the dielectric block and the film layer, and a photodetector means which comprises a plurality of photodetector elements and detects the intensity of the light beam reflected in total internal reflection at the interface, wherein the improvement comprises the steps of while causing said light beam to intermittently impinge upon the dielectric block, moving the optical system and the dielectric block relatively to each other so that the position in which the light beam impinges upon the interface changes, measuring the intensity of the light beam reflected in total internal reflection in each position of the interface a plurality of times in a time series by dividing the plurality of photodetector elements into a plurality of groups and differentiating the sums of the outputs of the photodetector elements in adjacent two groups in the direction in which the photodetector elements are arranged, smoothing a plurality of pieces of measured data obtained for each position of the interface thereby obtaining a piece of smoothed data for each position, statistically processing a plurality of pieces of smoothed data for different positions of the interface and obtaining data representative of the intensities of the light beam reflected at the interface.

In accordance with a twentieth aspect of the present invention, there is provided a measuring method for analyzing a sample by the use of a measuring apparatus comprising a measuring chip consisting of a dielectric block, a film layer formed on one face of the dielectric block and a sample holding system which holds the sample on the surface of the film layer, a light source which emits a light beam, an optical system which causes the light beam to enter the dielectric block at an angle of incidence such that total internal reflection conditions are satisfied at the interface of the dielectric block and the film layer, and a photodetector means which comprises a plurality of photodetector elements and detects the intensity of the light beam reflected in total internal reflection at the interface, wherein the improvement comprises the steps of while causing said light beam to intermittently impinge upon the dielectric block, moving the optical system and the dielectric block relatively to each other so that the position in which the light beam impinges upon the interface changes, measuring the intensity of the light beam reflected in total internal reflection in each position of the interface a plurality of times in a time series by calculating averages of outputs of a predetermined number of adjacent photodetector elements in sequence in the direction in which the photodetector elements are arranged and differentiating the averages in the direction in which the photodetector elements are arranged, smoothing a plurality of pieces of measured data obtained for each position of the interface thereby obtaining a piece of smoothed data for each position, statistically processing a plurality of pieces of smoothed data for different positions of the interface and obtaining data representative of the intensities of the light beam reflected at the interface.

In accordance with a twenty-first aspect of the present invention, there is provided a measuring method for analyzing a sample by the use of a measuring apparatus comprising a measuring chip consisting of a dielectric block, a film layer formed on one face of the dielectric block and a sample holding system which holds the sample on the surface of the film layer, a light source which emits a light beam, an optical system which causes the light beam to enter the dielectric block at an angle of incidence such that total internal reflection conditions are satisfied at the interface of the dielectric block and the film layer, and a photodetector means which comprises a plurality of photodetector elements and detects the intensity of the light beam reflected in total internal reflection at the interface, wherein the improvement comprises the steps of while causing said light beam to intermittently impinge upon the dielectric block, arranging the optical system to be able to cause the light beam to impinge upon the interface in a plurality of different positions, measuring the intensity of the light beam reflected in total internal reflection in each position of the interface a plurality of times in a time series by dividing the plurality of photodetector elements into a plurality of groups and differentiating the sums of the outputs of the photodetector elements in adjacent two groups in the direction in which the photodetector elements are arranged, smoothing a plurality of pieces of measured data obtained for each position of the interface thereby obtaining a piece of smoothed data for each position, statistically processing a plurality of pieces of smoothed data for different positions of the interface and obtaining data representative of the intensities of the light beam reflected at the interface.

In accordance with a twenty-second aspect of the present invention, there is provided a measuring method for analyzing a sample by the use of a measuring apparatus comprising a measuring chip consisting of a dielectric block, a film layer formed on one face of the dielectric block and a sample holding system which holds the sample on the surface of the film layer, a light source which emits a light beam, an optical system which causes the light beam to enter the dielectric block at an angle of incidence such that total internal reflection conditions are satisfied at the interface of the dielectric block and the film layer, and a photodetector means which comprises a plurality of photodetector elements and detects the intensity of the light beam reflected in total internal reflection at the interface, wherein the improvement comprises the steps of while causing said light beam to intermittently impinge upon the dielectric block, arranging the optical system to be able to cause the light beam to impinge upon the interface in a plurality of different positions, measuring the intensity of the light beam reflected in total internal reflection in each position of the interface a plurality of times in a time series by calculating averages of outputs of a predetermined number of adjacent photodetector elements in sequence in the direction in which the photodetector elements are arranged and differentiating the averages in the direction in which the photodetector elements are arranged, smoothing a plurality of pieces of measured data obtained for each position of the interface thereby obtaining a piece of smoothed data for each position, statistically processing a plurality of pieces of smoothed data for different positions of the interface and obtaining data representative of the intensities of the light beam reflected at the interface.

In accordance with a twenty-third aspect of the present invention, there is provided a measuring apparatus utilizing the phenomenon of attenuation in total internal reflection comprising a measuring chip consisting of a dielectric block, a film layer formed on one face of the dielectric block and a sample holding system which holds the sample on the surface of the film layer, a light source which emits a light beam, an optical system which causes the light beam to enter the dielectric block at an angle of incidence such that total internal reflection conditions are satisfied at the interface of the dielectric block and the film layer, a photodetector means which comprises a plurality of photodetector elements and detects the intensity of the light beam reflected in total internal reflection at the interface, an intermittent light beam projecting means which causes said light beam to intermittently impinge upon the dielectric block, a relative movement means which moves the optical system and the dielectric block relatively to each other so that the position in which the light beam impinges upon the interface changes, and an operation means which measures the intensity of the light beam reflected in total internal reflection in each position of the interface a plurality of times in a time series by dividing the plurality of photodetector elements into a plurality of groups and differentiating the sums of the outputs of the photodetector elements in adjacent two groups in the direction in which the photodetector elements are arranged, smoothes a plurality of pieces of measured data obtained for each position of the interface thereby obtaining a piece of smoothed data for each position, statistically processes a plurality of pieces of smoothed data for different positions of the interface and obtains data representative of the intensities of the light beam reflected at the interface.

In accordance with a twenty-fourth aspect of the present invention, there is provided a measuring apparatus utilizing the phenomenon of attenuation in total internal reflection comprising a measuring chip consisting of a dielectric block, a film layer formed on one face of the dielectric block and a sample holding system which holds the sample on the surface of the film layer, a light source which emits a light beam, an optical system which causes the light beam to enter the dielectric block at an angle of incidence such that total internal reflection conditions are satisfied at the interface of the dielectric block and the film layer, a photodetector means which comprises a plurality of photodetector elements and detects the intensity of the light beam reflected in total internal reflection at the interface, an intermittent light beam projecting means which causes said light beam to intermittently impinge upon the dielectric block, a relative movement means which moves the optical system and the dielectric block relatively to each other so that the position in which the light beam impinges upon the interface changes, and an operation means which measures the intensity of the light beam reflected in total internal reflection in each position of the interface a plurality of times in a time series by calculating averages of outputs of a predetermined number of adjacent photodetector elements in sequence in the direction in which the photodetector elements are arranged and differentiating the averages in the direction in which the photodetector elements are arranged, smoothes a plurality of pieces of measured data obtained for each position of the interface thereby obtaining a piece of smoothed data for each position, statistically processes a plurality of pieces of smoothed data for different positions of the interface and obtains data representative of the intensities of the light beam reflected at the interface.

In accordance with a twenty-fifth aspect of the present invention, there is provided a measuring apparatus utilizing the phenomenon of attenuation in total internal reflection comprising a measuring chip consisting of a dielectric block, a film layer formed on one face of the dielectric block and a sample holding system which holds the sample on the surface of the film layer, a light source which emits a light beam, an optical system which causes the light beam to enter the dielectric block at an angle of incidence such that total internal reflection conditions are satisfied at the interface of the dielectric block and the film layer, and is arranged to be able to cause the light beam to impinge upon the interface in a plurality of different positions, a photodetector means which comprises a plurality of photodetector elements and detects the intensity of the light beam reflected in total internal reflection at the interface, an intermittent light beam projecting means which causes said light beam to intermittently impinge upon the dielectric block, and an operation means which measures the intensity of the light beam reflected in total internal reflection in each position of the interface a plurality of times in a time series by dividing the plurality of photodetector elements into a plurality of groups and differentiating the sums of the outputs of the photodetector elements in adjacent two groups in the direction in which the photodetector elements are arranged, smoothes a plurality of pieces of measured data obtained for each position of the interface thereby obtaining a piece of smoothed data for each position, statistically processes a plurality of pieces of smoothed data for different positions of the interface and obtains data representative of the intensities of the light beam reflected at the interface.

In accordance with a twenty-sixth aspect of the present invention, there is provided a measuring apparatus utilizing the phenomenon of attenuation in total internal reflection comprising a measuring chip consisting of a dielectric block, a film layer formed on one face of the dielectric block and a sample holding system which holds the sample on the surface of the film layer, a light source which emits a light beam, an optical system which causes the light beam to enter the dielectric block at an angle of incidence such that total internal reflection conditions are satisfied at the interface of the dielectric block and the film layer, and is arranged to be able to cause the light beam to impinge upon the interface in a plurality of different positions, a photodetector means which comprises a plurality of photodetector elements and detects the intensity of the light beam reflected in total internal reflection at the interface, an intermittent light beam projecting means which causes said light beam to intermittently impinge upon the dielectric block, and an operation means which measures the intensity of the light beam reflected in total internal reflection in each position of the interface a plurality of times in a time series by calculating averages of outputs of a predetermined number of adjacent photodetector elements in sequence in the direction in which the photodetector elements are arranged and differentiating the averages in the direction in which the photodetector elements are arranged, smoothes a plurality of pieces of measured data obtained for each position of the interface thereby obtaining a piece of smoothed data for each position, statistically processes a plurality of pieces of smoothed data for different positions of the interface and obtains data representative of the intensities of the light beam reflected at the interface.

BRIEF DESCRIPTION OF THE DRAWINGS

FIG. 1 is a side view of a surface plasmon resonance sensor in accordance with a first embodiment of the present invention, FIG. 3 is a block diagram showing the electrical arrangement of the surface plasmon resonance sensor of the first embodiment, FIG. 5 is a side view of a surface plasmon resonance sensor in accordance with a second embodiment of the present invention, FIG. 21 is a block diagram showing the electrical arrangement of the surface plasmon resonance sensor of the twelfth embodiment.

DESCRIPTION OF THE PREFERRED EMBODIMENTS

Figure 2A:
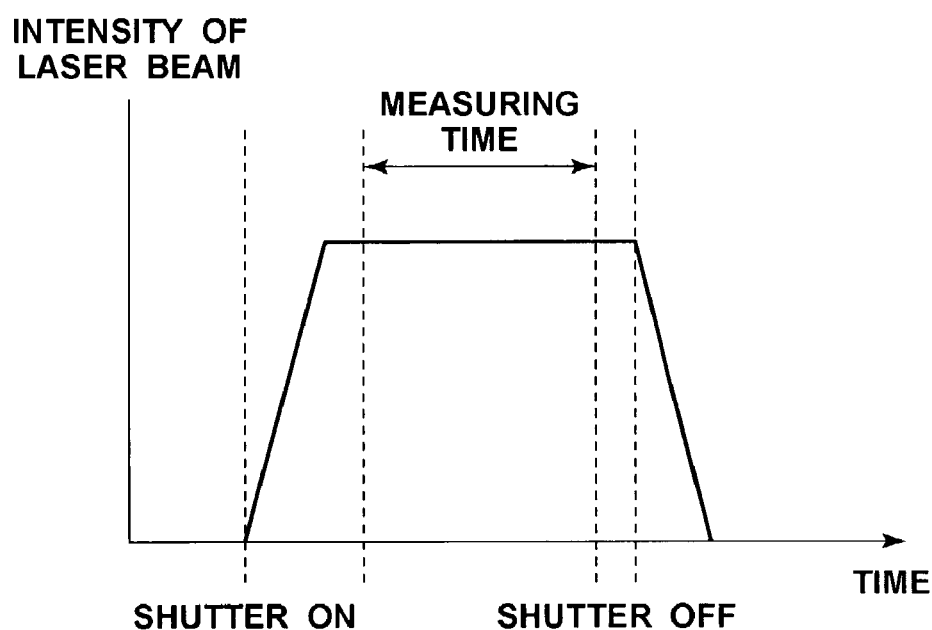
FIG. 2A is a view showing change with time in intensity of the laser beam on the interface when the shutter intermittently opens and closes the optical path.

In FIG. 1, a measuring apparatus (a surface plasmon resonance sensor) in accordance with a first embodiment of the present invention comprises a plurality of disposable measuring chips each comprising a dielectric block 10 which is like a truncated pyramid in shape and a metal film 12 of gold, silver, copper, aluminum or the like is formed on one face of the dielectric block 10.

The dielectric block 10 is formed, for instance, of transparent synthetic resin and the metal film 12 is provided on the bottom of a recessed portion 10a, which functions as a sample holding well for holding a sample liquid 11. In this particular embodiment, a sensing medium 30, which will be described later, is fixed on the metal film 12.

The disposable measuring chips are fixed in chip holding holes 31a provided in a turn table 31. A desired number of disposable measuring chips are fixed in the chip holding holes 31a provided in the turn table 31 and then the turn table 31 is intermittently rotated at regular angular intervals. A sample liquid 11 is spotted into the sample holding well 10a of the measuring chip stopped in a predetermined sample spotting position. Thereafter the turn table 31 is further rotated to bring a measuring chip provided with the sample liquid 11 to a measuring position shown in FIG. 1.

The surface plasmon resonance sensor of this embodiment further comprises a semiconductor laser 14 emitting a single laser beam 13, an incident optical system 15 which causes the laser beam 13 to enter the dielectric block 10 so that total internal reflection conditions are satisfied at the interface 10b of the dielectric block and the metal film 12 and various angles of incidence of the light beam to the interface of the dielectric block 10 and the metal film 12 can be obtained, a collimator lens 16 which converts the laser beam 13 reflected in total internal reflection at the interface 10b into a parallel laser beam, a photodetector means 17 which detects the parallel laser beam 13, a differential amplifier array 18 connected to the photodetector means 17, a driver 19, a signal processing section (CPU) 20 which may comprise, for instance, a computer system, and a shutter 50 which intermittently opens and closes the optical path between the laser 14 and the dielectric block 10.

The incident optical system 15 comprises a collimator lens 15a which converts the laser beam 13, emitted from the laser 14 as a divergent light beam, into a parallel laser beam, and a condenser lens 15b which converges the collimated laser beam 13 on the interface 10b.

Since converged by the condenser lens 15b as described above, the laser beam 13 includes components impinging upon the interface at various angles of incidence θ. The laser 14 and the incident optical system 15 are arranged so that the angles of incidence θ are all not smaller than the angle of total internal reflection. Accordingly, the laser beam 13 is reflected in total internal reflection at the interface 10b and the reflected laser beam 13 includes components reflected at the interface 10b at various angles of reflection. The incident optical system 15 may be arranged to cause the laser beam 13 to impinge upon the interface 10b in a defocused state. This arrangement averages errors in detecting states of surface plasmon resonance and improves measuring accuracy.

The laser beam 13 is caused to impinge upon the interface 10b in a p-polarized state. This can be realized by positioning the laser 14 so that the laser beam 13 impinges upon the interface 10b in a p-polarized state. Otherwise, the direction of polarization of the laser beam 13 may be controlled by a wavelength plate.

Figure 2B:
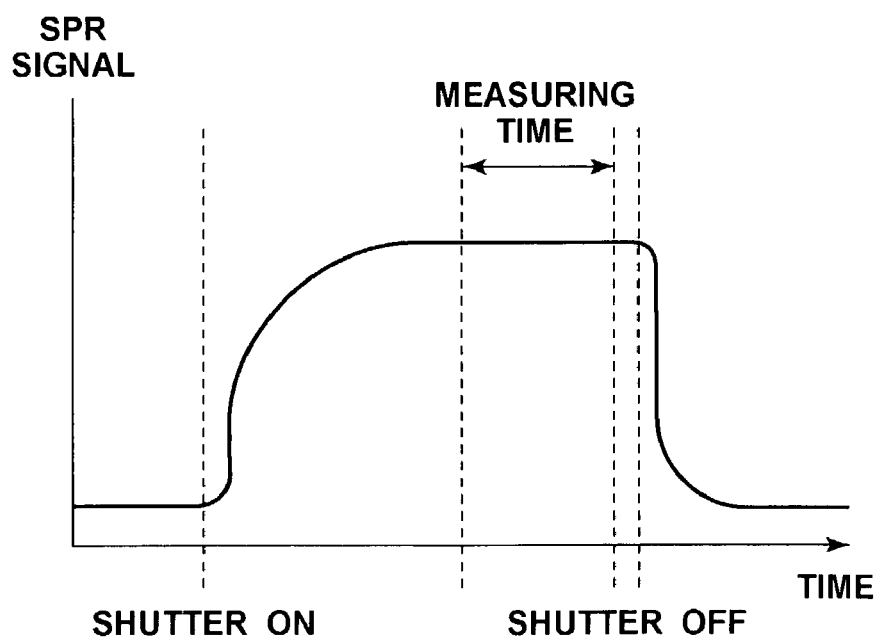
FIG. 2B is a view showing change with time in level of the output signal of the photodetector means when the shutter intermittently opens and closes the optical path.

The shutter 50 is provided with a driver (not shown) which controls opening and closing of the shutter 50 under the control of the signal processing section 20. FIG. 2A shows change in intensity of the laser beam 13 on the interface 10b when the shutter 50 intermittently opens and closes the optical path. As can be seen from FIG. 2A, the intensity of the laser beam 13 on the interface 10b is not stabilized during opening closing of the shutter 50. Accordingly, it is preferred that measurement be done after the shutter 50 is completely opened and before the shutter 50 begins to be closed. The output signal of the photodetector means 17 exhibits transient response characteristics such as shown in FIG. 2B. Accordingly, it is preferred that measurement be done after the lapse of transient response time and before the shutter 50 begins to be closed. It is preferred that the shutter 50 be driven to cause the laser beam 13 to impinge upon the dielectric block 10 so that change of the temperature of the sample liquid 11 and change of the temperature of the dielectric block 10 which affects the liquid sample 11 are suppressed to not larger than 0.5° C. When change of the temperature of the sample liquid 11 and change of the temperature of the dielectric block 10 are suppressed to not larger than 0.1° C., measurement can be done more accurately.

Analysis of a sample by the surface plasmon resonance sensor of this embodiment will be described, hereinbelow.

The shutter 50 is first opened under the control of a signal from the signal processing section 20 and the laser beam 13 is allowed to enter the incident optical system 15. As shown in FIG. 1, the laser beam 13 emitted from the laser 14 as a divergent light beam is converged on the interface 10b of the dielectric block 10 and the metal film 12. As described above, the laser beam 13 includes components impinging upon the interface at various angles of incidence θ. Accordingly, the laser beam 13 is reflected in total internal reflection at the interface 10b and the reflected laser beam 13 includes components reflected at the interface 10b at various angles of reflection.

The laser beam 13 reflected in total internal reflection at the interface 10b is detected by the photodetector means 17 after collimated by the collimator lens 16. In this particular embodiment, the intensity of the reflected laser beam 13 is measured at a timing at which the intensity of the reflected laser beam 13 on the light receiving surface of the photodetector means 17 is maximized. In this particular embodiment, the photodetector means 17 is a photodiode array in which a plurality of photodiodes 17a, 17b, 17c . . . are arranged in a row in a direction substantially normal to the direction of travel of the collimated laser beam 13 in a plane of FIG. 1. That is, the components of the reflected laser beam 13 impinge upon different photodiodes 17a, 17b, 17c . . . .

FIG. 3 is a block diagram showing the electrical arrangement of the surface plasmon resonance sensor of this embodiment. As shown in FIG. 3, the driver 19 comprises sample hold circuits 22a, 22b, 22c . . . which sample-hold the outputs of the respective differential amplifiers 18a, 18b, 18c . . . of the differential amplifier array 18, a multiplexer 23 into which the outputs of the sample hold circuits 22a, 22b, 22c . . . are input, an A/D convertor 24 which digitizes the outputs of the multiplexer 23 and inputs them into the signal processing section 20, a drive circuit 25 which drives the multiplexer 23 and the sample hold circuits 22a, 22b, 22c . . . , and a controller 26 which controls the drive circuit 25 under the control of the signal processing section 20. The signal processing section 20 controls the controller 26 and the shutter 50 in synchronization with each other. The outputs of adjacent pairs of the photodiodes 17a, 17b, 17c . . . are respectively input into the differential amplifiers 18a, 18b, 18c . . . of the differential amplifier array 18. Accordingly, the outputs of the differential amplifiers 18a, 18b, 18c . . . of the differential amplifier array 18 represents differentials of the outputs of the photodiodes 17a, 17b, 17c . . . (representing the intensities of light which they detect) in the direction in which the photodiodes 17a, 17b, 17c . . . are arranged.

The outputs of the differential amplifiers 18a, 18b, 18c . . . are sample-held at predetermined timings by the respective sample hold circuits 22a, 22b, 22c . . . and input into the multiplexer 23. The multiplexer 23 inputs the outputs of the respective sample hold circuits 22a, 22b, 22c . . . into the A/D convertor 24 in a predetermined order. The A/D convertor 24 digitizes the outputs of the respective sample hold circuits 22a, 22b, 22c . . . and inputs them into the signal processing section 20.

Figure 4A:
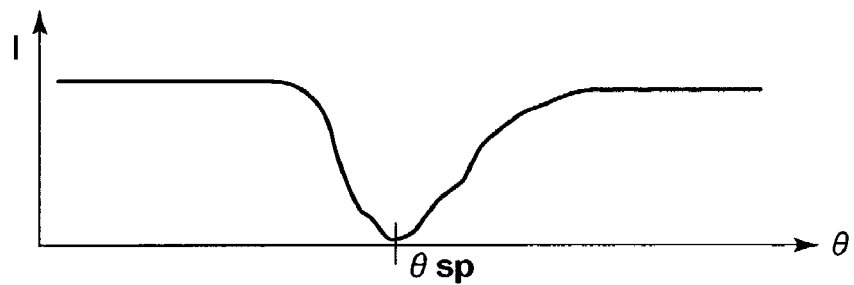
FIG. 4A is a view showing an example of the relation between the intensity I of the component of the laser beam reflected in total internal reflection at the interface and the angle of incidence θ of the component.

FIG. 4A shows an example of the relation between the intensity I of the component of the laser beam 13 reflected in total internal reflection at the interface 10b and the angle of incidence θ of the component.

A component of the laser beam 13 impinging upon the interface 10b at a particular angle of incidence θsp excites surface plasmon in the interface 10b between the metal film 12 and the sample liquid 11 and the intensity I of the component reflected in total internal reflection at the interface 10b sharply drops. That is, the particular angle of incidence is the attenuation angle θsp and the intensity I of the reflected laser beam 13 is minimized at the attenuation angle θsp. The sharp drop of the reflected laser beam 13 is observed as a dark line as indicated at D in FIG. 1.

Figure 4B:
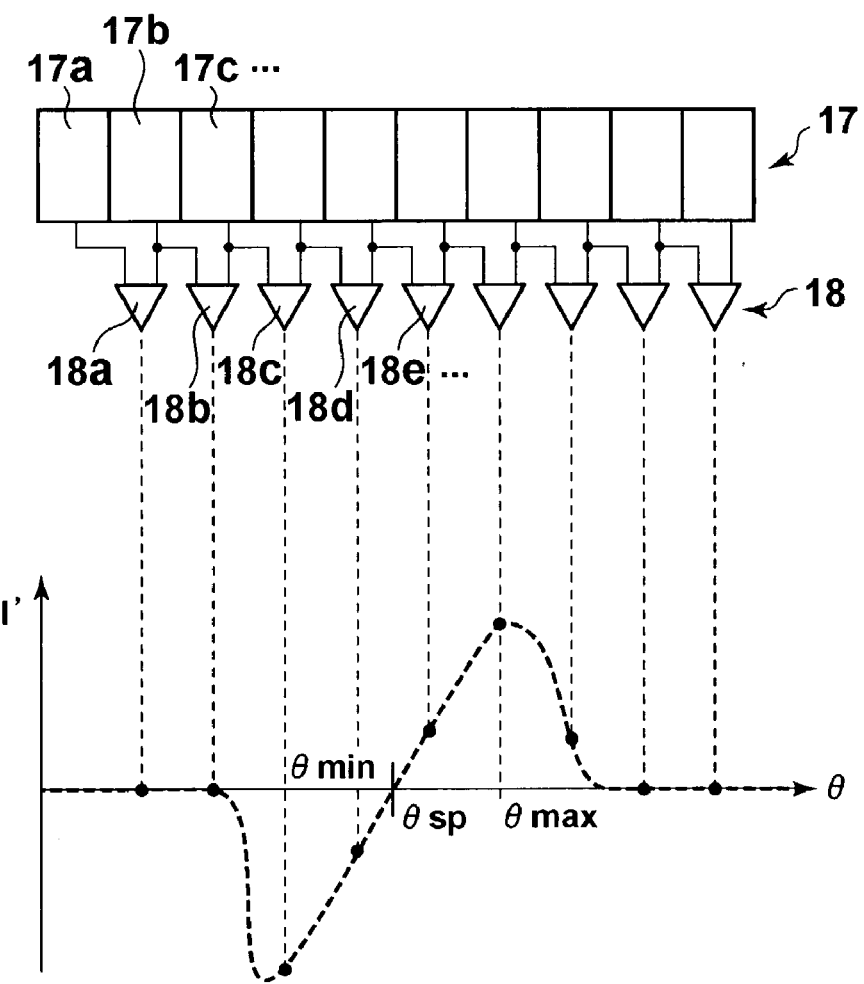
FIG. 4B is a view showing the relation between the output I' of the differential amplifier and the angle of incidence θsp.

As shown in FIG. 4B, the positions of the photodiodes 17a, 17b, 17c . . . in the direction in which they are arranged are one-to-one correspondence with the angle of incidence θsp. FIG. 4B also shows the relation between the output I' of the differential amplifier (the differential of the intensities I of the reflected laser beam 13) and the position of the photodiode 17a, 17b, 17c . . . in the direction in which the photodiodes are arranged (or the angle of incidence θsp).

The signal processing section 20 selects one of the differential amplifiers 18a, 18b, 18c . . . whose output I' is the closest to 0 corresponding to the attenuation angle θsp on the basis of the differentials I' input into the A/D convertor 24 (the differential amplifier 18d in the particular example shown in FIG. 4B) and carries out a predetermined correction on the output I' of the selected differential amplifier. Then the signal processing section 20 causes a display 21 to display the corrected value of the output I' of the selected differential amplifier. Sometimes there is a differential amplifier whose output I' is just 0. Naturally, the differential amplifier is selected in this case.

Thereafter, each time a predetermined time lapses, the corrected value of the output I' of the selected differential amplifier (18d) is displayed. The output I' increases and decreases with left and right movement of the curve shown in FIG. 4A which takes place with change of the dielectric constant or the refractive index of the material in contact with the metal film 12 of the measuring chip. Accordingly, when the output I' is kept measured, change with time of the properties (refractive index) of the material in contact with the metal film 12 can be detected.

In this particular embodiment, since a sensing medium 30 which combines with a particular material in the sample liquid 11 is fixed on the metal film 12 and the refractive index of the sensing medium 30 changes depending on the state of combination of the sensing medium 30 and the particular material, change of the state of combination of the sensing medium 30 and the particular material can be detected by keeping measuring the differential value I'. In this case, both the sample liquid 11 and the sensing medium 30 are the object of analysis. As combinations of such a specific material and a sensing material, for instance, combinations of an antigen and an antibody have been known.

As can be understood from the description above, in this embodiment where a photodiode array consisting of a plurality of photodiodes 17a, 17b, 17c . . . arranged in a row is employed as the photodetector means 17a, the dark line can be detected even if the curve shown in FIG. 4A is largely moved left and right. That is, by using a photodetector means 17 in the form of an array, a wide dynamic range of measurement can be ensured.

Instead of employing a differential amplifier array 18 comprising a plurality of differential amplifiers 18a, 18b, 18c . . . , a single differential amplifier may be employed. In this case, the outputs of the photodiodes 17a, 17b, 17c . . . are switched by a multiplexer so that outputs of adjacent pairs of photodiodes 17a, 17b, 17c . . . are input into the single differential amplifier in sequence.

In order to display change with time of the state of combination of the particular material in the sample liquid 11 and the sensing medium 30, the difference ΔI' between the initial differential value I' and the differential value I' at that time may be displayed instead of displaying the differential value I' at that time.

After the lapse of a predetermined time, the signal processing section 20 closes the shutter 50 so that the laser beam 13 emitted from the laser 14 cannot impinge upon the dielectric block 10.

In the surface plasmon resonance sensor of this embodiment, since the time for which the dielectric block 10 is exposed to the laser beam 13 is shortened by virtue of the shutter 50, change of temperature of the sample liquid 11 and change of temperature of the dielectric block 10 which affects the sample liquid 11 are suppressed and accordingly, drift of the detecting signal is prevented.

A surface plasmon resonance sensor in accordance with a second embodiment of the present invention will be described with reference to FIG. 5, hereinbelow. In FIG. 5, the elements analogous to those shown in FIG. 1 are given the same reference numerals and will not be described here.

The surface plasmon resonance sensor of this embodiment differs from that of the first embodiment in the structure of the intermittent light beam projecting means.

That is, the surface plasmon resonance sensor of this embodiment is provided with a driver 51 which intermittently drives the laser 14 in place of the shutter 50 which intermittently opens and closes the optical path between the laser 14 and the dielectric block 10.

The surface plasmon resonance sensor of the second embodiment is substantially the same in operation as the surface plasmon resonance sensor of the first embodiment.

In the second embodiment, since intermittently driven by the driver 51, the laser 14 is preferably provided with an oscillation wavelength stabilizing means, which is disclosed, for instance, in Japanese Unexamined Patent Publication No. 2000-155093.

Also in this embodiment, change in intensity of the laser beam 13 on the interface 10b when the laser 14 is turned on off is substantially as shown in FIG. 2A and the output signal of the photodetector means 17 exhibits transient response characteristics such as shown in FIG. 2B. Accordingly, it is preferred that measurement be done after the lapse of transient response time and before the laser 14 is turned off. It is preferred that the driver 51 drives the laser 14 to cause the laser beam 13 to impinge upon the dielectric block 10 so that change of the temperature of the sample liquid 11 and change of the temperature of the dielectric block 10 which affects the liquid sample 11 are suppressed to not larger than 0.5° C. When change of the temperature of the sample liquid 11 and change of the temperature of the dielectric block 10 are suppressed to not larger than 0.1° C., measurement can be done more accurately.

Figure 6:
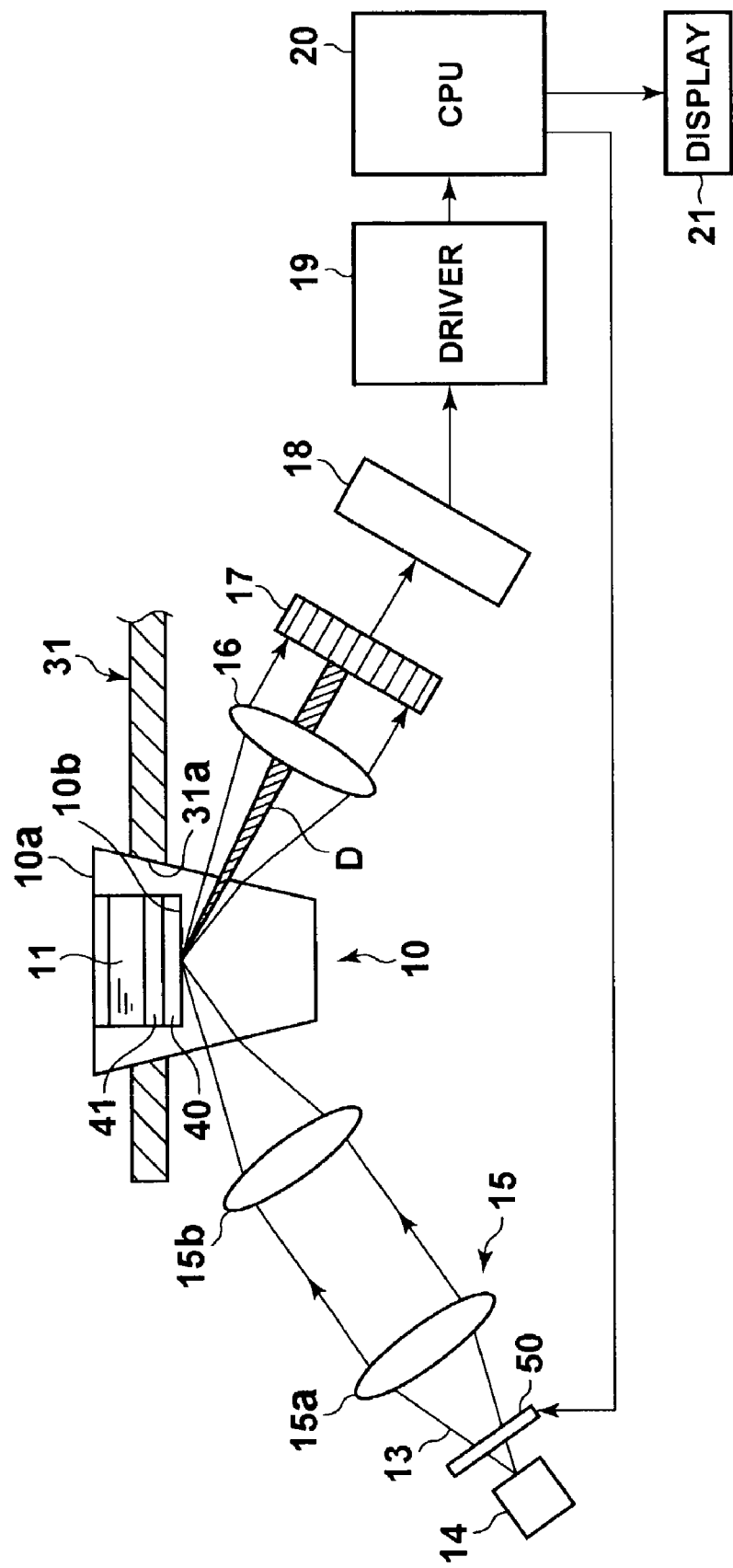
FIG. 6 is a side view of a leaky mode sensor in accordance with a third embodiment of the present invention.

A third embodiment of the present invention will be described with reference to FIG. 6, hereinbelow. In FIG. 6, the elements analogous to those shown in FIG. 1 are given the same reference numerals and will not be described here.

The measuring apparatus of the third embodiment is substantially the same as that of the first embodiment except that the former is a leaky mode sensor and the latter is a surface plasmon resonance sensor. That is, in the leaky mode sensor of the third embodiment, the dielectric block 10 is formed of synthetic resin or optical glass (e.g., BK7), and a clad layer 40 is formed on one face of the dielectric block 10 and an optical waveguide layer 41 is formed on the clad layer 40.

The clad layer 40 is in the form of film of dielectric material or metal (e.g., gold) which is lower in refractive index than the dielectric block 10. The optical waveguide layer 41 is in the form of film of dielectric material which is higher in refractive index than the clad layer 40 (e.g., PMMA). For example, the clad layer 40 is 36.5 nm in thickness when it is in the form of a metal film and the optical waveguide layer 41 is 700 nm in thickness when it is formed of PMMA.

In the leaky mode sensor with this arrangement, when the laser beam 13 emitted from the laser 14 is caused to impinge upon the clad layer 40 through the dielectric block 10 at an angle not smaller than an angle of total internal reflection, only light having a particular wave number and impinging upon the optical waveguide layer 41 at a particular angle of incidence comes to propagate through the optical waveguide layer 41 in a waveguide mode after passing through the clad layer 40. When the waveguide mode is thus excited, almost all the incident light is taken in the optical waveguide layer 41 and accordingly, the intensity of light reflected in total internal reflection at the interface of the dielectric block 10 and the clad layer 40 sharply drops. That is, attenuation in total internal reflection occurs.

Since the wave number of light to be propagated through the optical waveguide layer 41 in a waveguide mode depends upon the refractive index of the sample liquid 11 on the optical waveguide layer 41, the refractive index and/or the properties of the sample liquid 11 related to the refractive index can be detected on the basis of the angle of incidence at which the attenuation in total internal reflection occurs.

Figure 7:
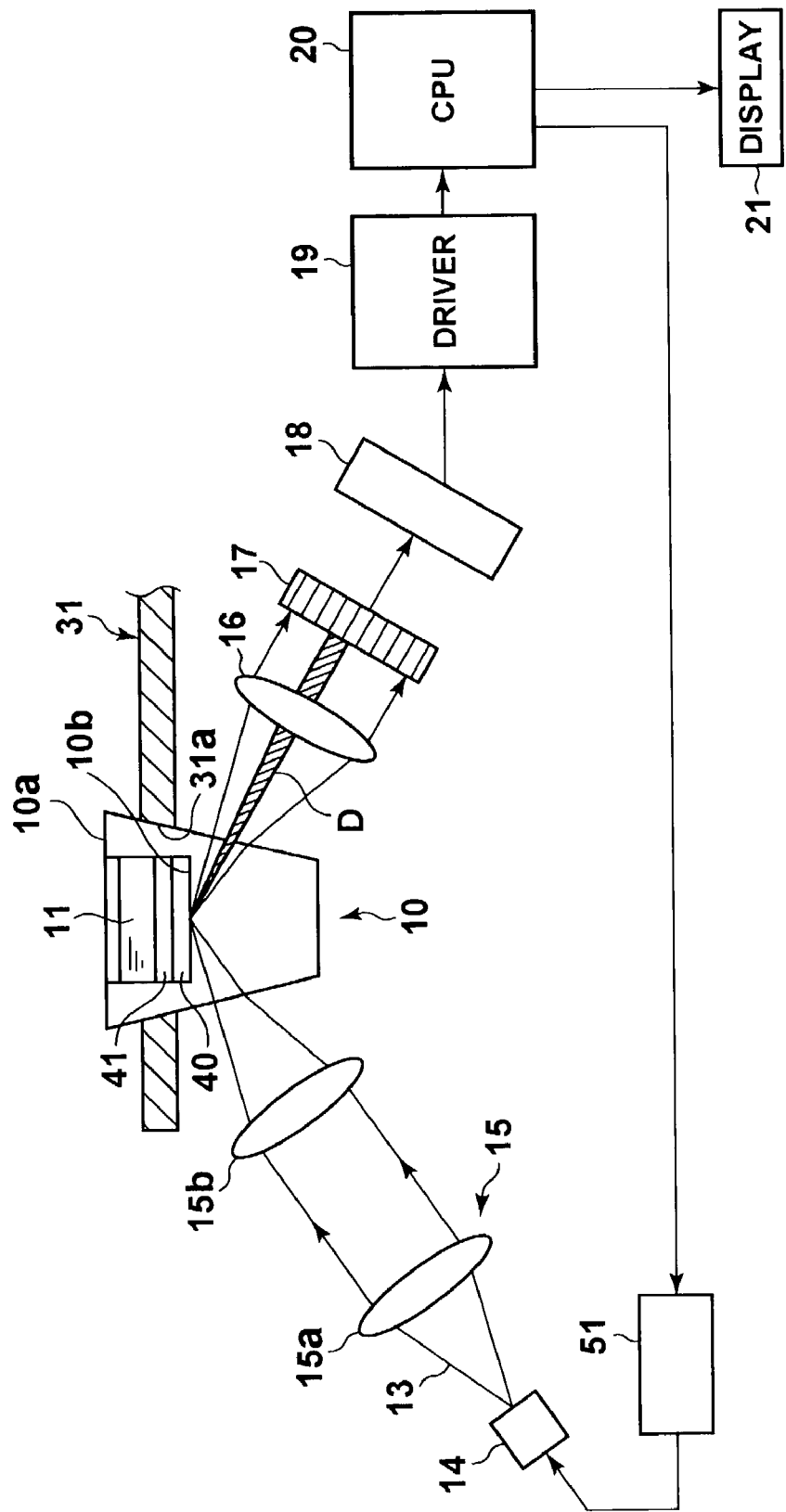
FIG. 7 is a side view of a leaky mode sensor in accordance with a fourth embodiment of the present invention.

A leaky mode sensor in accordance with a fourth embodiment of the present invention will be described with reference to FIG. 7, hereinbelow. In FIG. 7, the elements analogous to those shown in FIG. 6 are given the same reference numerals and will not be described here.

The leaky mode sensor of this embodiment differs from that of the third embodiment in the structure of the intermittent light beam projecting means.

That is, the leaky mode sensor of this embodiment is provided with a driver 51 which intermittently drives the laser 14 in place of the shutter 50 which intermittently opens and closes the optical path between the laser 14 and the dielectric block 10.

A measuring apparatus (a surface plasmon resonance sensor) in accordance with a fifth embodiment of the present invention will be described with reference to FIG. 8, hereinbelow.

Figure 8:
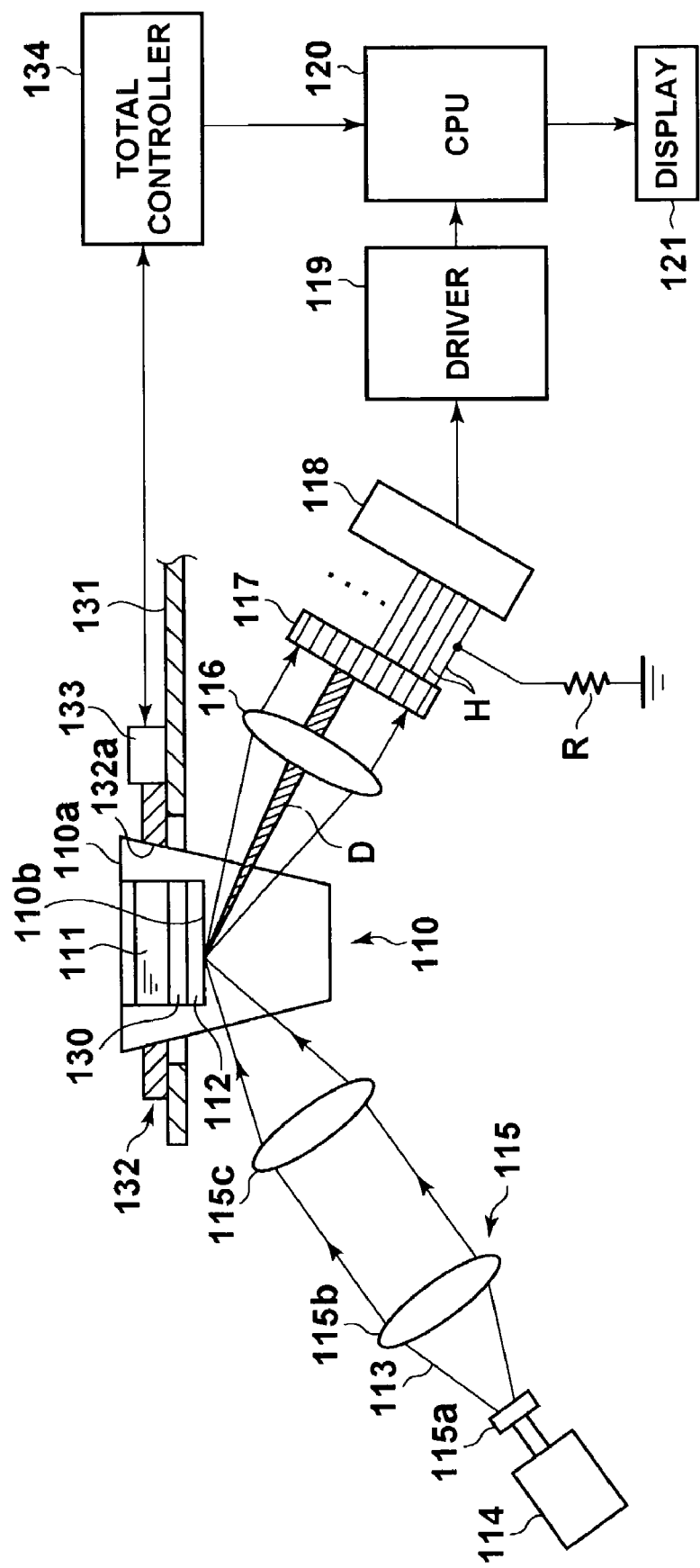
FIG. 8 is a side view of a surface plasmon resonance sensor in accordance with a fifth embodiment of the present invention.

In FIG. 8, the surface plasmon resonance sensor in accordance with the fifth embodiment of the present invention comprises a plurality of disposable measuring chips each comprising a dielectric block 110 which is like a truncated pyramid in shape and a metal film 112 of gold, silver, copper, aluminum or the like is formed on one face of the dielectric block 110.

The dielectric block 110 is formed, for instance, of transparent synthetic resin or optical glass such as BK7 and the metal film 112 is provided on the bottom of a recessed portion 110a, which functions as a sample holding well for holding a sample liquid 111. In this particular embodiment, a sensing medium 130, which will be described later, is fixed on the metal film 112.

The disposable measuring chips are fixed in chip holding holes 132a of a movable table 132 provided in a turn table 131. The movable table 132 is moved by an actuator 1313 in the direction normal to the plane of FIG. 8 relatively to the turn table 131.

A desired number of disposable measuring chips are fixed in the chip holding holes 132a and then the turn table 131 is intermittently rotated at regular angular intervals. A sample liquid 111 is spotted into the sample holding well 110a of the measuring chip stopped in a predetermined sample spotting position. Thereafter the turn table 131 is further rotated to bring a measuring chip provided with the sample liquid 11 to a measuring position shown in FIG. 8.

The surface plasmon resonance sensor of this embodiment further comprises a semiconductor laser 14 emitting a single laser beam 113, an incident optical system 115 which causes the laser beam 113 to enter the dielectric block 110 so that total internal reflection conditions are satisfied at the interface 110b of the dielectric block 110 and the metal film 112 and various angles of incidence of the light beam to the interface of the dielectric block 110 and the metal film 112 can be obtained, a cylindrical lens 116 which converts the laser beam 113 reflected in total internal reflection at the interface 110b into a parallel laser beam only in the plane of FIG. 8, a photodetector means 117 which detects the parallel laser beam 113, a driver 119 connected to the photodetector means 117, a signal processing section (CPU) 120 which may comprise, for instance, a computer system, and a display 121 connected to the signal processing section 120.

The incident optical system 115 comprises a cylindrical lens 115a which diverges the laser beam 113 emitted from the laser 114 as a thin parallel light beam only in the plane of FIG. 8, a cylindrical lens 115b which converts the divergent laser beam 113 into a laser beam parallel only in the plane of FIG. 8, and a cylindrical lens 115c which converges the parallel laser beam 113 only in the plane of FIG. 8.

Figure 10:
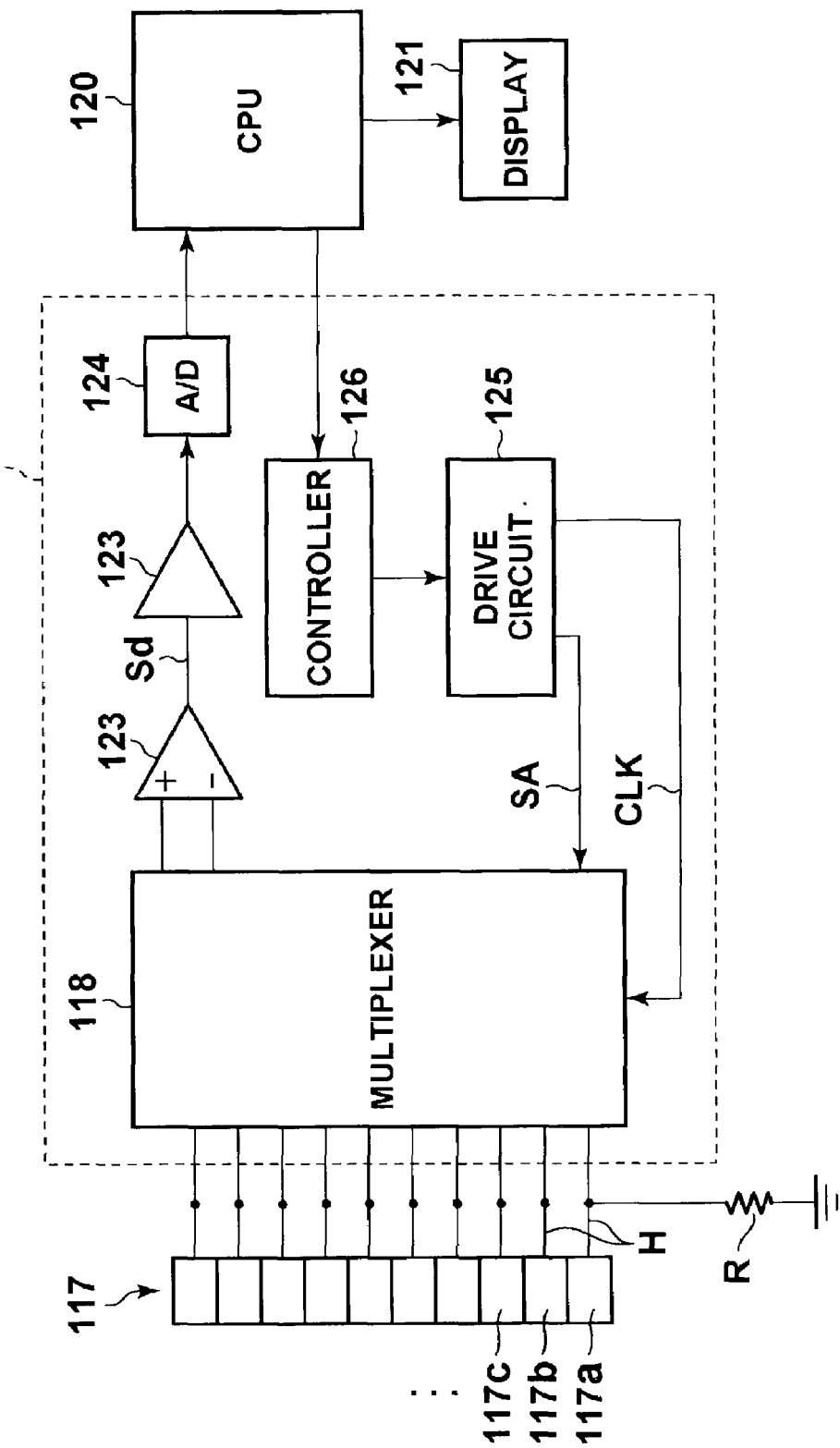
FIG. 10 is a block diagram showing the electrical arrangement of the surface plasmon resonance sensor of the fifth embodiment.

FIG. 10 is a block diagram showing the electrical arrangement of the surface plasmon resonance sensor of this embodiment. The photodetector means 117 is a photodiode array in which a plurality of photodiodes 117a, 117b, 117c . . . are arranged in a row. The photodiodes 117a, 117b, 117c . . . are connected to a multiplexer 118 of the driver 119 by way of signal lines H.

Each signal line H is grounded by way of a resistor R. Though, in FIGS. 8 and 10, only one of the signal lines H is grounded, all the signal lines H are grounded in the same manner.

The driver 119 comprises a differential amplifier 122 connected to a pair of output terminals of the multiplexer 118, an amplifier 123 which amplifies the output of the differential amplifier 122, an A/D convertor 124 which digitizes the outputs of the amplifier 123 and inputs them into the signal processing section 120, a drive circuit 125 which inputs clocks CLK and address signals SA into the multiplexer 118 and drives the multiplexer 118 and a controller 126 which controls the drive circuit 125 under the control of the signal processing section 120.

Figure 9:
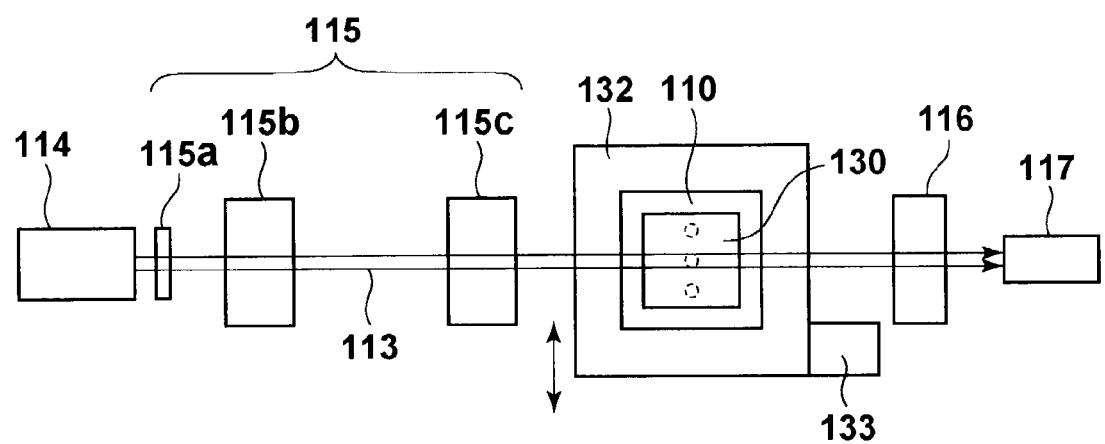
FIG. 9 is a plan view showing the optical system of the surface plasmon resonance sensor of the fifth embodiment.

The laser beam 113 emitted from the laser 114 as a thin parallel light beam travels as it is in the plane of FIG. 9. Whereas, in the plane of FIG. 8, the laser beam 113 is diverged by the cylindrical lens 115a, converted into a parallel light beam by the cylindrical lens 115b and converged on the interface 110b of the dielectric block 110 and the metal film 112 by the cylindrical lens 115c. Accordingly, the laser beam 113 includes components impinging upon the interface 110b at various angles of incidence θ. The laser 114 and the incident optical system 115 are arranged so that the angles of incidence θ are all not smaller than the angle of total internal reflection and in the range where surface plasmon is excited. Accordingly, the laser beam 113 is reflected in total internal reflection at the interface 110b and the reflected laser beam 113 includes components reflected at the interface 110b at various angles of reflection.

The laser beam 113 is caused to impinge upon the interface 110b in a p-polarized state. This can be realized by positioning the laser 114 so that the laser beam 113 impinges upon the interface 110b in a p-polarized state. Otherwise, the direction of polarization of the laser beam 113 may be controlled by a wavelength plate.

The laser beam 113 which is reflected in total internal reflection at the interface 110b and paralleled in the plane of FIG. 8 by the cylindrical lens 116 is detected by the photodetector means 117. The photodetector means 117 is oriented so that the direction in which the photodiodes 117a, 117b, 117c are arranged is substantially normal to the direction of travel of the parallel laser beam 113 in a plane of FIG. 8. That is, the components of the reflected laser beam 113 impinge upon different photodiodes 117a, 117b, 117c . . . .

The outputs of the photodiodes 117a, 117b, 117c . . . are input into the multiplexer 118. The multiplexer 118 is controlled by the drive circuit 125 and inputs outputs of adjacent pairs of photodiodes 117a, 117b, 117c . . . into the differential amplifier 122 in sequence. The differential amplifier 122 outputs the difference between outputs of respective adjacent pairs of photodiodes 117a, 117b, 117c . . . and accordingly, the differential signals Sd output from the differential amplifier 122 represent differentials of the outputs of the photodiodes 117a, 117b, 117c . . . in the direction in which they are arranged.

The differential signals Sd output from the differential amplifier 122 in sequence are amplified by the amplifier 123 and then input into the A/D convertor 124. The A/D convertor 124 digitizes the differential signals Sd and inputs them into the signal processing section 120.

Figure 11A:
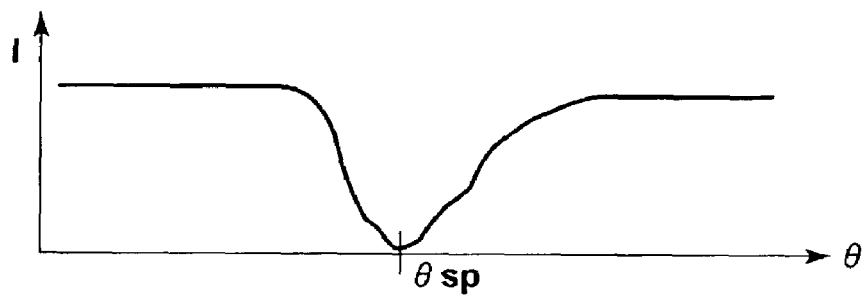
FIG. 11A shows an example of the relation between the intensity I of the component of the laser beam reflected in total internal reflection at the interface and the angle of incidence θ of the component.

FIG. 11A shows an example of the relation between the intensity I of the component of the laser beam 113 reflected in total internal reflection at the interface 110b and the angle of incidence θ of the component.

A component of the laser beam 113 impinging upon the interface 110b at a particular angle of incidence θsp excites surface plasmon in the interface 110b between the metal film 112 and the sample liquid 11 and the intensity I of the component reflected in total internal reflection at the interface 110b sharply drops. That is, the particular angle of incidence is the attenuation angle θsp and the intensity I of the reflected laser beam 113 is minimized at the attenuation angle θsp. The sharp drop of the reflected laser beam 113 is observed as a dark line as indicated at D in FIG. 8.

Figure 11B:
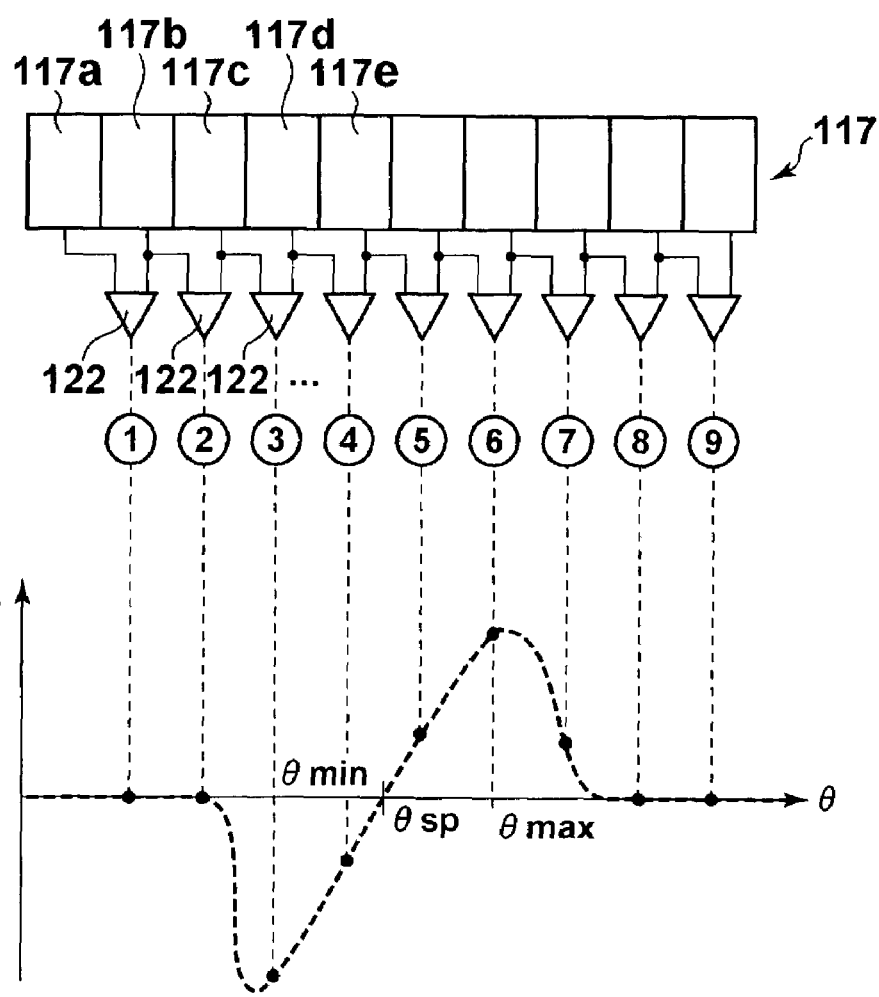
FIG. 11B is a view showing the relation between the differentials I' of the intensities I of the reflected laser beam represented by the differential signals Sd out put from the differential amplifier in the fifth embodiment and the angle of incidence θsp.

As shown in FIG. 11B, the positions of the photodiodes 117a, 117b, 117c . . . in the direction in which they are arranged are one-to-one correspondence with the angle of incidence θsp. FIG. 11B also shows the relation between the differentials I' of the intensities I of the reflected laser beam represented by the differential signals Sd out put from the differential amplifier in this embodiment and the angle of incidence θsp (or the position of the photodiode 117a, 117b, 117c . . . in the direction in which the photodiodes are arranged (or the angle of incidence θsp). Though, in FIG. 11B, pairs of adjacent photodiodes are connected to differential amplifiers 122 for the purpose of simplification, actually pairs of adjacent photodiodes are connected to a single differential amplifier 122 in sequence.

The signal processing section 20 selects a combination of photodiodes corresponding to a differential I' is closest to 0 corresponding to the attenuation angle θsp on the basis of the differentials I' output from the A/D convertor 124 (the photodiodes 117d and 117e in the particular example shown in FIGS. 11A and 11B) and causes the display 121 to display the differential I'. Sometimes there is a combination of the photodiodes whose differential I' is just 0. Naturally, the differential I' (=0) is displayed in this case.

Thereafter, each time a predetermined time lapses, the value of the differential I' of the selected combination of the photodiodes 117d and 117e is displayed. The differential I' increases and decreases with left and right movement of the curve shown in FIG. 11A which takes place with change of the dielectric constant or the refractive index of the material in contact with the metal film 112 of the measuring chip. Accordingly, when the differential I' is kept measured, change with time of the properties (refractive index) of the material in contact with the metal film 112 can be detected.

In this particular embodiment, since a sensing medium 130 which combines with a particular material in the sample liquid 111 is fixed on the metal film 112 and the refractive index of the sensing medium 130 changes depending on the state of combination of the sensing medium 130 and the particular material, change of the state of combination of the sensing medium 130 and the particular material can be detected by keeping measuring the differential value I'. In this case, both the sample liquid 111 and the sensing medium 130 are the object of analysis. As combinations of such a specific material and a sensing material 130, for instance, combinations of an antigen and an antibody have been known.

As can be understood from the description above, in this embodiment where a photodiode array consisting of a plurality of photodiodes 117a, 117b, 117c . . . arranged in a row is employed as the photodetector means 117, the dark line can be detected even if the curve shown in FIG. 11A is largely moved left and right. That is, by using a photodetector means 117 in the form of an array, a wide dynamic range of measurement can be ensured.

In this particular embodiment, since each of the signal lines H connected to the photodiodes 117a, 117b, 117c . . . is grounded, accumulation of charge in the multiplexer 118 during measurement of intensity I of the reflected laser beam 113 is prevented. Accordingly, there is no accumulated charge in the multiplexer 118 which can be added to the outputs of the photodiodes 117a, 117b, 117c . . . upon the next measurement, whereby generation of charge noise due to accumulated charge can be prevented and detecting signals can be high in S/N.

In order to display change with time of the state of combination of the particular material in the sample liquid 111 and the sensing medium 130, the difference ΔI' between the initial differential value I' and the differential value I' at that time may be displayed instead of displaying the differential value I' at that time.

In the surface plasmon resonance sensor of this embodiment, fluctuation in the result of measurement due to non-uniformity of the thickness of the metal film 112 and/or the reactivity of the sensing material 130 and/or due to dust adhering to the metal film 112 is prevented in the following manner.

That is, the actuator 133 drives the movable table 132 a plurality of times for each measurement to stop the measuring chip in N (N stands for a plural number) different positions. In this case, the laser beam 113 impinges upon the interface 110b in N different positions. That is, N results of measurement are obtained for each measurement.

N differentials I' are input into the signal processing section 120 from the A/D convertor 124 for each of nine positions of the photodiodes (① to ⑨ in FIG. 11B) and the signal processing section 120 takes a median of the N differentials I' as the representative differential I' for the position. On the basis of such representative differentials I', the state of combination of the particular material in the sample liquid 111 and the sensing medium 130 is detected.

The actuator 133 is controlled by a total controller 134 and a timing signal is input into the CPPPPU 120 from the total controller 134 each time the movable table 132 is stopped. The signal processing section 120 takes in the differentials I' from the A/D convertor 124 each time the timing signal is input.

The representative differential I' thus obtained can be less affected by non-uniformity of the thickness of the metal film 112 and/or the reactivity of the sensing material 130 and external disturbance such as dust adhering to the sensing material 130. Accordingly, the surface plasmon resonance sensor of this embodiment can suppress fluctuation of the result of measurement due to non-uniformity of the thickness of the metal film 112 and/or the reactivity of the sensing material 130 and external disturbance such as dust adhering to the sensing material 130.

Further since the laser beam 113 is focused on the interface 110, the range of angle of incidence of the light beam at which the attenuation in total internal reflection is observed is not widened and the measuring sensitivity does not deteriorate.

Further, in this embodiment, since fluctuation of the result of measurement can be prevented by the use of only a single measuring chip comprising a dielectric block 110 and a metal film 112, the time required to supply the sample and carry out the measuring process can be shortened and measurement can be done more efficiently as compared with the case where measurement on one sample is done by the use of a plurality of measuring chips.

Though, in the fifth embodiment, a median of the N differentials I' is taken as the representative differential I' for the position, an average of the differentials I' included in a range of a predetermined width including the median may be taken as the representative differential I' for the position. Further, an average of the N differentials I' minus the maximum value and the minimum value may be taken as the representative differential I' for the position.

Figure 12:
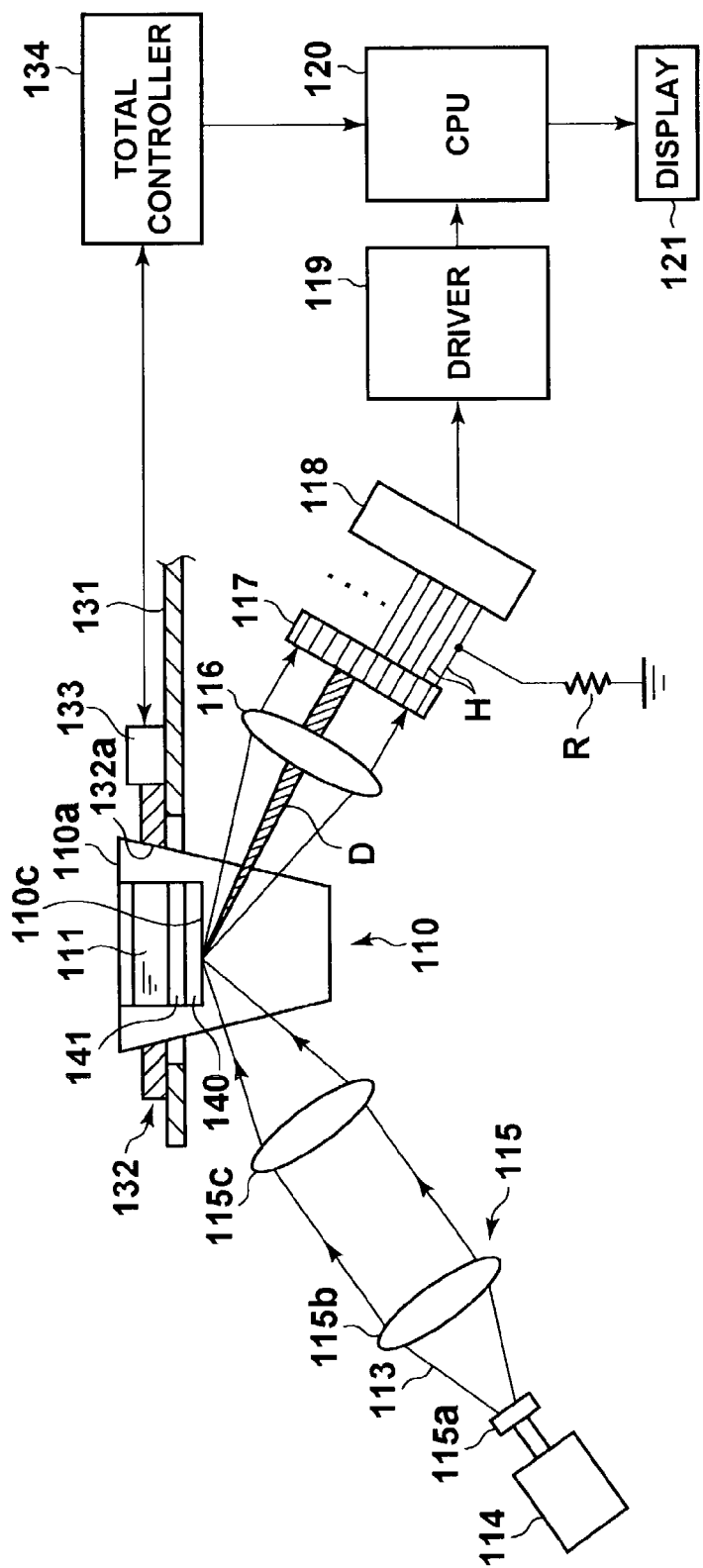
FIG. 12 is a side view of a leaky mode sensor in accordance with a sixth embodiment of the present invention.

A sixth embodiment of the present invention will be described with reference to FIG. 12, hereinbelow. In FIG. 12, the elements analogous to those shown in FIG. 8 are given the same reference numerals and will not be described here.

The measuring apparatus of the sixth embodiment is substantially the same as that of the fifth embodiment except that the former is a leaky mode sensor and the latter is a surface plasmon resonance sensor. That is, in the leaky mode sensor of the sixth embodiment, the dielectric block 110 is formed of synthetic resin or optical glass (e.g., BK7), and a clad layer 140 is formed on one face of the dielectric block 110 and an optical waveguide layer 141 is formed on the clad layer 140.

The clad layer 140 is in the form of film of dielectric material or metal (e.g., gold) which is lower in refractive index than the dielectric block 110. The optical waveguide layer 141 is in the form of film of dielectric material which is higher in refractive index than the clad layer 140 (e.g., PMMA). For example, the clad layer 140 is 36.5 nm in thickness when it is in the form of a metal film and the optical waveguide layer 141 is 700 nm in thickness when it is formed of PMMA.

The position in which the light beam impinges upon the interface may be changed by other mechanism than those employed in the fifth and sixth embodiments described above where the dielectric block 110 is moved relatively to the laser beam 113. Measuring apparatuses in accordance with seventh to tenth embodiments of the present invention where the light beam is caused to impinge upon the interface in a plurality of different positions by different mechanisms will be described, hereinbelow. Though the measuring apparatuses of the seventh to ninth embodiments are surface plasmon resonance sensors, the mechanism for causing the light beam to impinge upon the interface in a plurality of different positions may be applied also to the leaky mode sensor.

Figure 13:
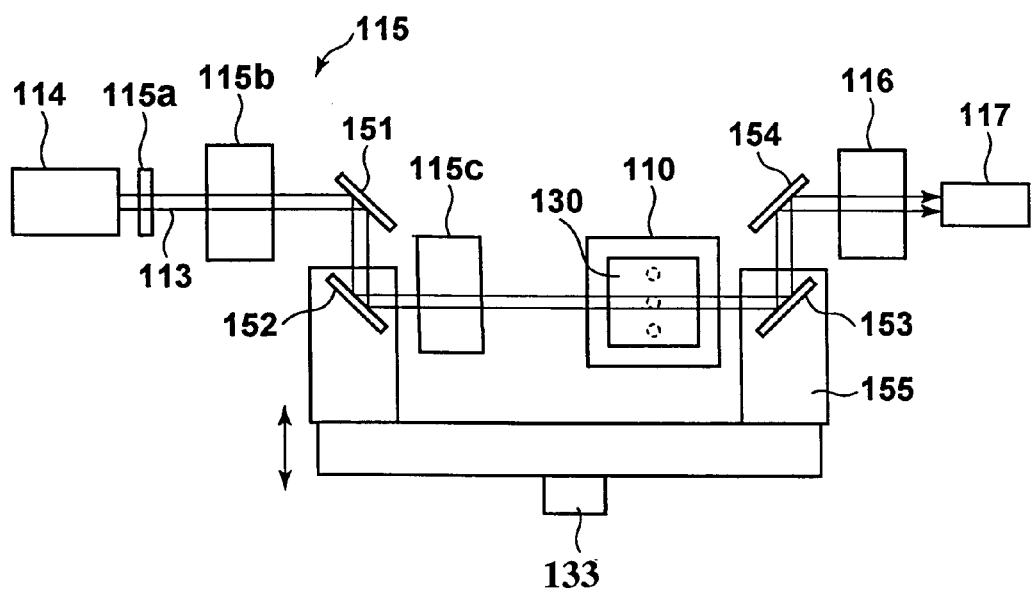
FIG. 13 is a plan view showing the optical system of the surface plasmon resonance sensor of the seventh embodiment.

FIG. 13 shows the optical system employed in a surface plasmon resonance sensor in accordance with the seventh embodiment of the present invention. In FIG. 13, the elements analogous to those shown in FIG. 9 are given the same reference numerals and will not be described here.

In the seventh embodiment, a pair of mirrors 151 and 152 are inserted between the cylindrical lenses 115b and 115c so that the optical path of the laser beam 113 to the dielectric block 110 is bent twice by 90° as seen in plan and the optical path of the laser beam 113 from the dielectric block 110 to the photodetector means 117 is bent twice by 90° as seen in plan by a pair of mirrors 153 and 154. The mirror 152 which reflects the laser beam 113 toward the dielectric block 110 and the mirror 153 which reflects the laser beam 113 reflected at the interface 110b are mounted on a movable table 155 which is moved up and down by an actuator 133.

In this embodiment, by moving the mirrors 152 and 153 with the measuring chip kept stationary in the measuring position, the position in which the laser beam 113 impinges upon the interface 110b can be changed.

Figure 14:
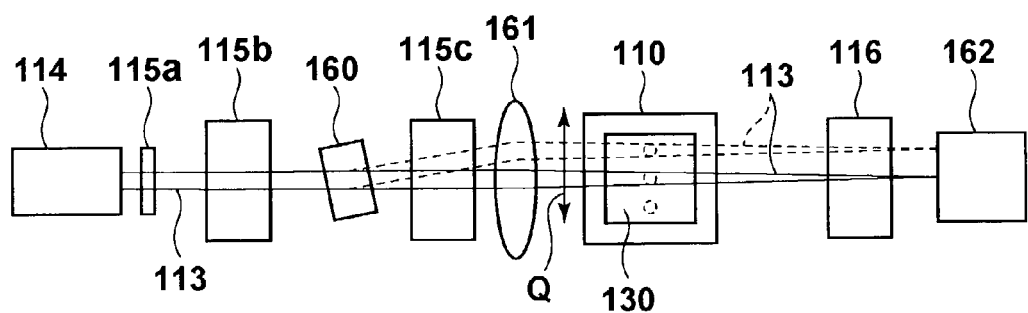
FIG. 14 is a plan view showing the optical system of the surface plasmon resonance sensor of the eighth embodiment.

FIG. 14 shows the optical system employed in a surface plasmon resonance sensor in accordance with the eighth embodiment of the present invention. In FIG. 14, the elements analogous to those shown in FIG. 9 are given the same reference numerals and will not be described here.

In the eighth embodiment, an AOD (acousto-optic deflector) 160 is inserted between the cylindrical lens 115b and 115c and another cylindrical lens 161 having a refracting power only in the plane of FIG. 14 is inserted between the cylindrical lens 115c and the dielectric block 110. When the AOD 160 is driven, the laser beam 113 is deflected in the direction of arrow Q.

In this embodiment, by driving the AOD 160 to deflect the laser beam 113 with the measuring chip kept stationary in the measuring position, the position in which the laser beam 113 impinges upon the interface 110b can be changed.

In this embodiment, when the position in which the laser beam 113 impinges upon the interface 110b changes, the laser beam 113 is reflected at the interface 110b in a different direction. In order to deal with change of the direction in which the reflected laser beam 113 travels, a photodetector means 162 having photodetector elements which can receive the laser beam 113 traveling in the deflected direction (upward or downward in FIG. 14) is employed. For example, the photodetector means 162 may be a two-dimensional CCD.

Figure 15:
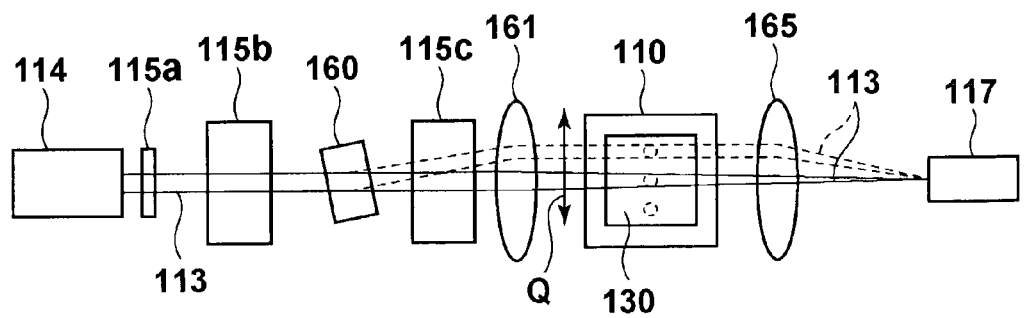
FIG. 15 is a plan view showing the optical system of the surface plasmon resonance sensor of the ninth embodiment.

FIG. 15 shows the optical system employed in a surface plasmon resonance sensor in accordance with the ninth embodiment of the present invention. In FIG. 15, the elements analogous to those shown in FIG. 9 are given the same reference numerals and will not be described here.

The optical system of the ninth embodiment differs from that of the eighth embodiment shown in FIG. 14 in that a condenser lens 165 in the form a circular lens having a refracting power also in the plane of FIG. 15 is employed in place of the cylindrical lens 116 and a photodetector means 117 having a linear array of photodetector elements is employed in place of the photodetector means 162 like a two-dimensional CCD.

In this embodiment, the laser beam 113 reflected at the interface 110b is converged by the condenser lens 165 and led to the thin photodetector means 117 irrespective of the position in which the laser beam 113 is reflected.

Figure 16:
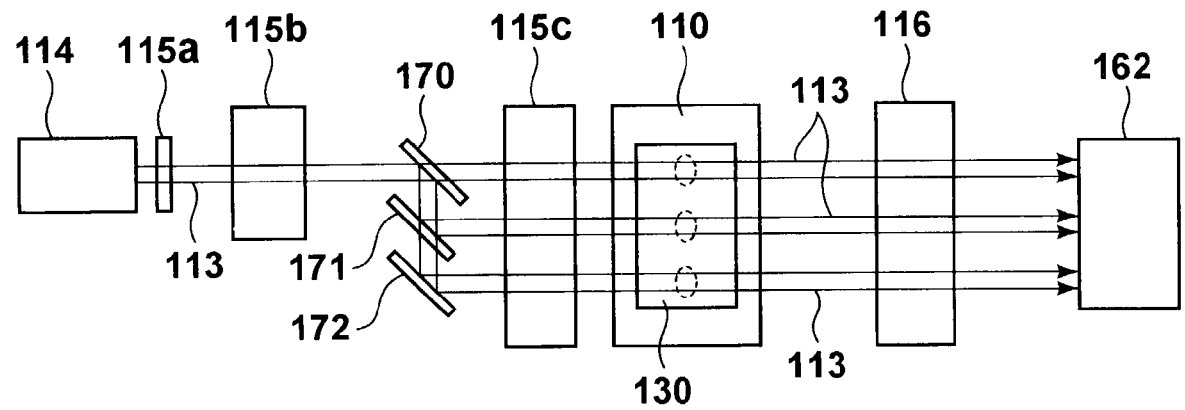
FIG. 16 is a plan view showing the optical system of the surface plasmon resonance sensor of the tenth embodiment.

FIG. 16 shows the optical system employed in a surface plasmon resonance sensor in accordance with the tenth embodiment of the present invention. In FIG. 16, the elements analogous to those shown in FIG. 9 are given the same reference numerals and will not be described here.

In the tenth embodiment, the laser beam 113 passing through the cylindrical lens 115b is split into three beams traveling in parallel to each other by three half-silvered mirrors 170, 171 and 172. The three laser beams simultaneously impinge upon the interface 110b in different positions.

In this embodiment, three laser beam 113 reflected at the interface 110b in three different positions are simultaneously radiated from the measuring chip. In order to deal with this situation, a photodetector means 162 having photodetector elements which are arranged also in the direction in which the three laser beams 113 is arranged (in the vertical direction in FIG. 16) is employed. For example, the photodetector means 162 may be a two-dimensional CCD.

Figure 17:
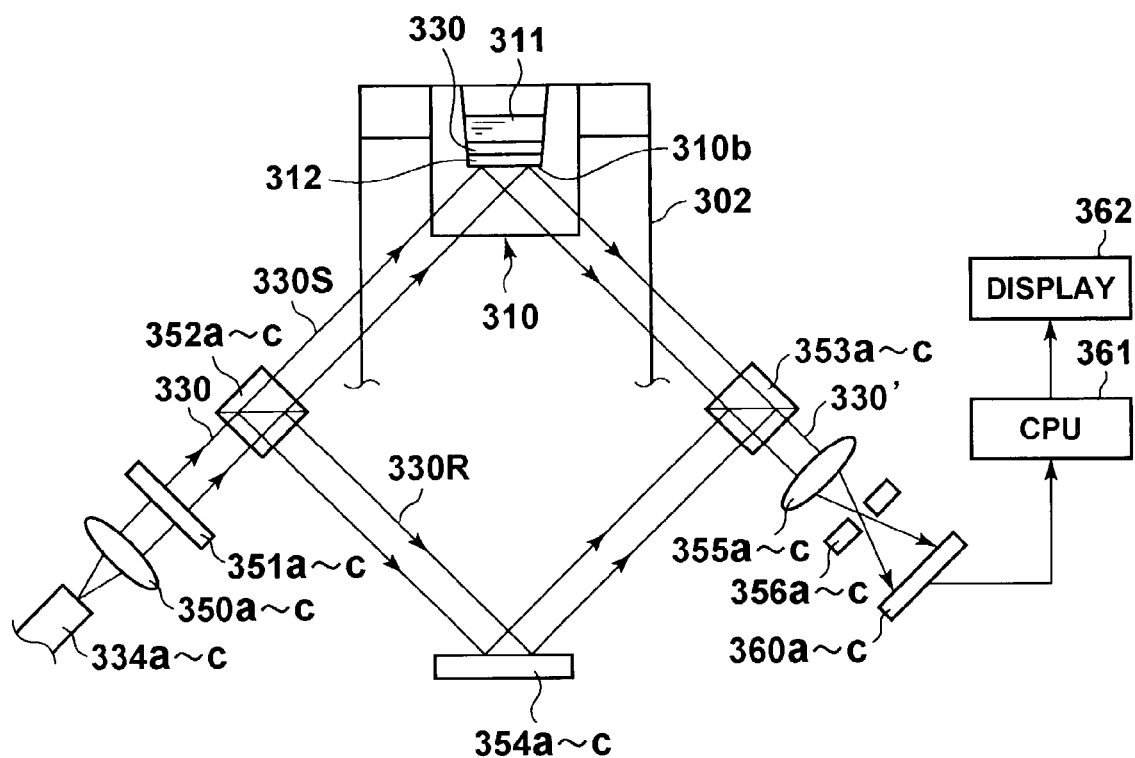
FIG. 17 is a side view of a surface plasmon resonance sensor in accordance with an eleventh embodiment of the present invention.

FIG. 17 shows a surface plasmon resonance sensor in accordance with an eleventh embodiment of the present invention.

In this embodiment, three optical fibers 334a, 334b and 334c are disposed on one side of a block 302 holding a dielectric block 310 and three CCDs 360a, 360b and 360c are disposed on the other side of the block 302. A collimator lens 350a, an interference optical system, a condenser lens 355a and an aperture 356a are disposed between the optical fiber 334a and the CCD 360a. The interference optical system consists of a polarizing filter 351a, a half-silvered mirror 352a, a half-silvered mirror 353a and a mirror 354a. A collimator lens 350b, an interference optical system, a condenser lens 355b and an aperture 356b are disposed between the optical fiber 334b and the CCD 360b. The interference optical system consists of a polarizing filter 351b, a half-silvered mirror 352b, a half-silvered mirror 353b and a mirror 354b. A collimator lens 350c, an interference optical system, a condenser lens 355c and an aperture 356c are disposed between the optical fiber 334c and the CCD 360c. The interference optical system consists of a polarizing filter 351c, a half-silvered mirror 352c, a half-silvered mirror 353c and a mirror 354c. The CCDs 360a to 360c are connected to a signal processing section 361 and the signal processing section 361 is connected to a display 362.

Measurement through the system from the optical fiber 334a to the CCD 360a will be described by way of example, hereinbelow.

The rear end of the optical fiber 334a is coupled to a laser (not shown) equivalent to the laser 14 shown in FIG. 1, and a laser beam 330 is radiated from the front end of the optical fiver as a divergent beam. The laser beam 330 is collimated by the collimator lens 350a and impinges upon the polarizing filter 351a. The laser beam 330 is linearly polarized by the polarizing filter 351a so that it impinges upon the interface 310b between the metal film 312 and the dielectric block 310 in a p-polarized state is split into a measuring beam 330S and a reference beam 330R by the half-silvered mirror 352a. The measuring beam 330S passing through the half-silvered mirror 352a impinges upon the interface 310b.

The measuring beam 330S reflected in total internal reflection at the interface 310b impinges upon the half-silvered mirror 353a and is combined with the reference beam 330R reflected at the mirror 354a into a combined beam 330'. The combined beam 330' is condensed by the condenser lens 355a and impinges upon the CCD 360a through the aperture 356a. At this time, interference fringes are generated in the combined beam 330' according to the state of interference between the measuring beam 330S and the reference beam 330R and the interference fringes are detected by the CCD 360a.

The sensing medium 330 fixed on the surface of the metal film 312 combines with a particular material in the sample liquid 311. As combinations of such a specific material and a sensing material, for instance, combinations of an antigen and an antibody have been known. Whether an antigen-antibody reaction occurs can be detected by detecting change of the interference fringes by the CCD 360a. That is, as the refractive index of the sensing material 330 changes with the state of combination of the particular material and the sensing material 330, the interference between the measuring beam 330S reflected in total internal reflection at the interface 310b and the reference beam 330R changes. In this case, both the sample liquid 311 and the sensing medium 330 are the object of analysis.

The signal processing section 361 detects whether a reaction takes place on the basis of the principle and causes the display 362 to display the result of the detection. At this time, the outputs of the other CCDs 360b and 360c are input into the signal processing section 361 in addition to the output of the CCD 360a, and the signal processing section 361 takes as a representative of the state of interference fringes, for instance, the average of the outputs of the CCDs 360a, 360b and 360c and detects whether a reaction takes place on the basis of the representative data.

Figure 18:
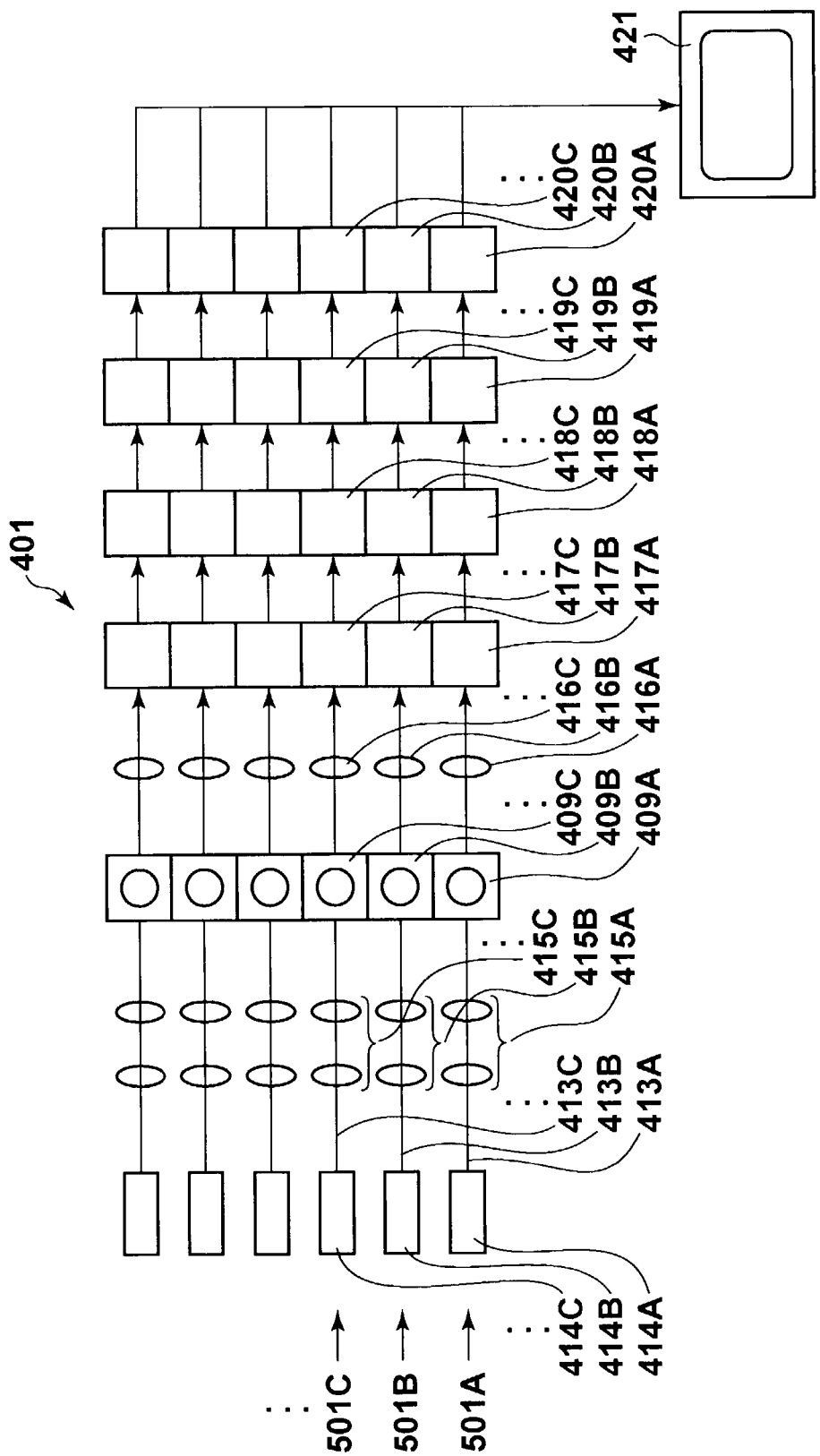
FIG. 18 is a plan view showing a surface plasmon resonance sensor in accordance with a twelfth embodiment of the present invention.

FIG. 18 shows a surface plasmon resonance sensor in accordance with a twelfth embodiment of the present invention. The surface plasmon resonance sensor 401 is a provided with a plurality of measuring units 501A, 501B, 501C . . . of the same structure and can analyze a plurality of samples at one time.

The measuring units will be described, hereinbelow, with the suffixed alphabet (e.g., A, B, C) removed from the reference numerals of the respective elements. Each measuring unit 501 comprises a measuring chip 409, a laser source 414 which emits a laser beam 413, an incident optical system 415 which causes the laser beam 413 to impinge upon an interface 410b between a dielectric block 412 (to be described later) and a metal film 412 (to be described later), a collimator lens 416 which converts the laser beam 413 reflected in total internal reflection at the interface 410b into a parallel laser beam, a photodetector means 417 which detects the intensity of the parallel laser beam 413, a differential amplifier array 418 connected to the photodetector means 417, a driver 419 connected to the differential amplifier array 418, and a signal processing section (CPU) 420 which may comprise, for instance, a computer system and is connected to the driver 419. The signal processing section 420 carries out smoothing to be described later.

Figure 20:
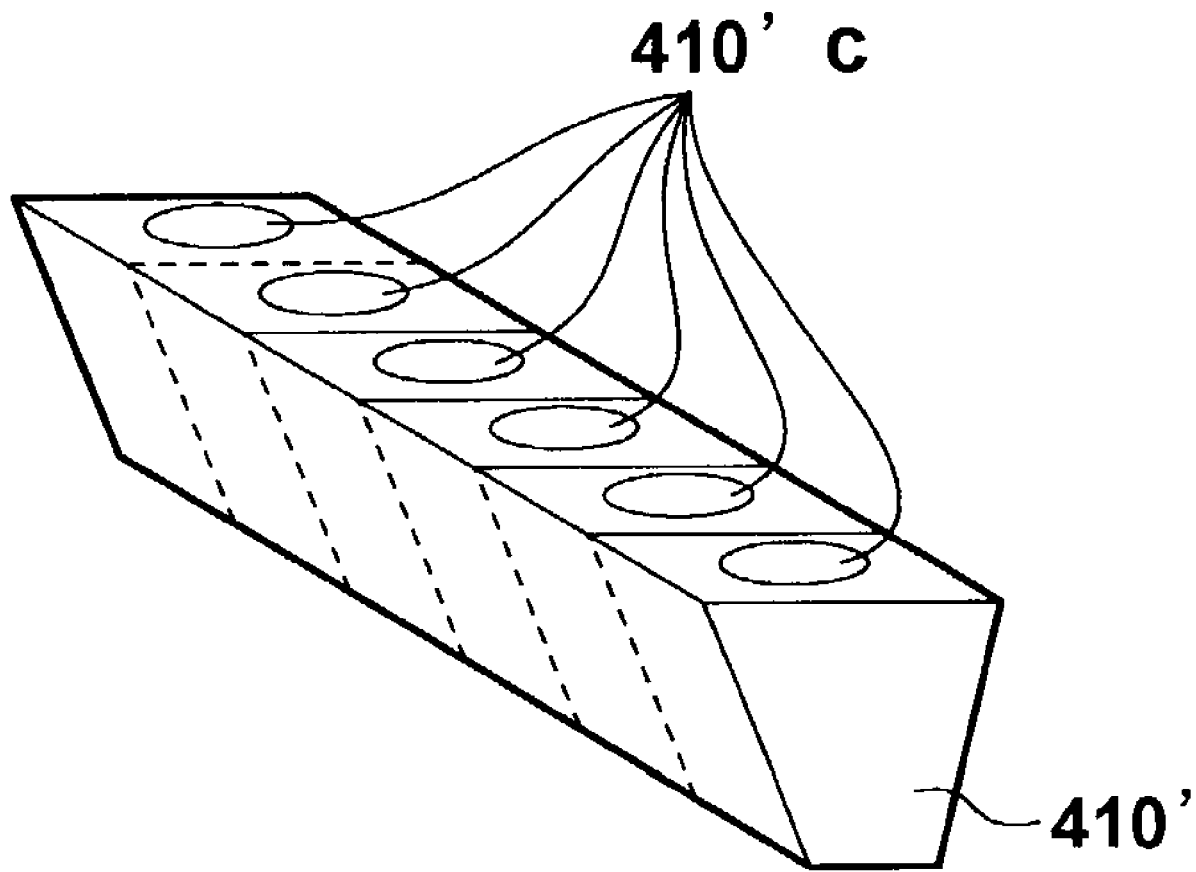
FIG. 20 is a modification of the measuring chip employed in the surface plasmon resonance sensor of the twelfth embodiment.

The measuring chip 409 comprises a dielectric block 410 which is like a truncated pyramid in shape and a metal film 412 of gold, silver, copper, aluminum or the like is formed on one face of the dielectric block 410. The dielectric block 410 is formed, for instance, of transparent synthetic resin and the metal film 412 is provided on the bottom of a recessed portion 410a, which functions as a sample holding well for holding a sample liquid 411. A sensing medium 430, which will be described later, may be fixed on the metal film 412. The dielectric blocks of measuring chips of a plurality of measuring units may be integrated as a modification shown in FIG. 20. In FIG. 20, reference numeral 410' denotes a dielectric block and reference numeral 410'c denotes a recessed portion of the modification.

The incident optical system 415 comprises a collimator lens 415a which converts the laser beam 413, emitted from the laser 414 as a divergent light beam, into a parallel laser beam, and a condenser lens 415b which converges the collimated laser beam 413 on the interface 410b.

Since converged by the condenser lens 415b as described above, the laser beam 413 includes components impinging upon the interface at various angles of incidence θ. The laser 414 and the incident optical system 415 are arranged so that the angles of incidence θ are all not smaller than the angle of total internal reflection. Accordingly, the laser beam 413 is reflected in total internal reflection at the interface 410b and the reflected laser beam 413 includes components reflected at the interface 410b at various angles of reflection. The incident optical system 415 may be arranged to cause the laser beam 413 to impinge upon the interface 410b in a defocused state. This arrangement causes the laser beam 413 to be reflected at the interface 410b over a wider area thereof and averages errors in detecting states of surface plasmon resonance and improves measuring accuracy.

The laser beam 413 is caused to impinge upon the interface 410b in a p-polarized state. This can be realized by positioning the laser 414 so that the laser beam 413 impinges upon the interface 410b in a p-polarized state. Otherwise, the direction of polarization of the laser beam 413 may be controlled by a wavelength plate.

The surface plasmon resonance sensor 401 of this embodiment further comprises a display 421 connected to the signal processing sections 420A, 420B, 420C . . . of the measuring units.

Analysis of a sample by the surface plasmon resonance sensor of this embodiment will be described, hereinbelow.

Figure 19:
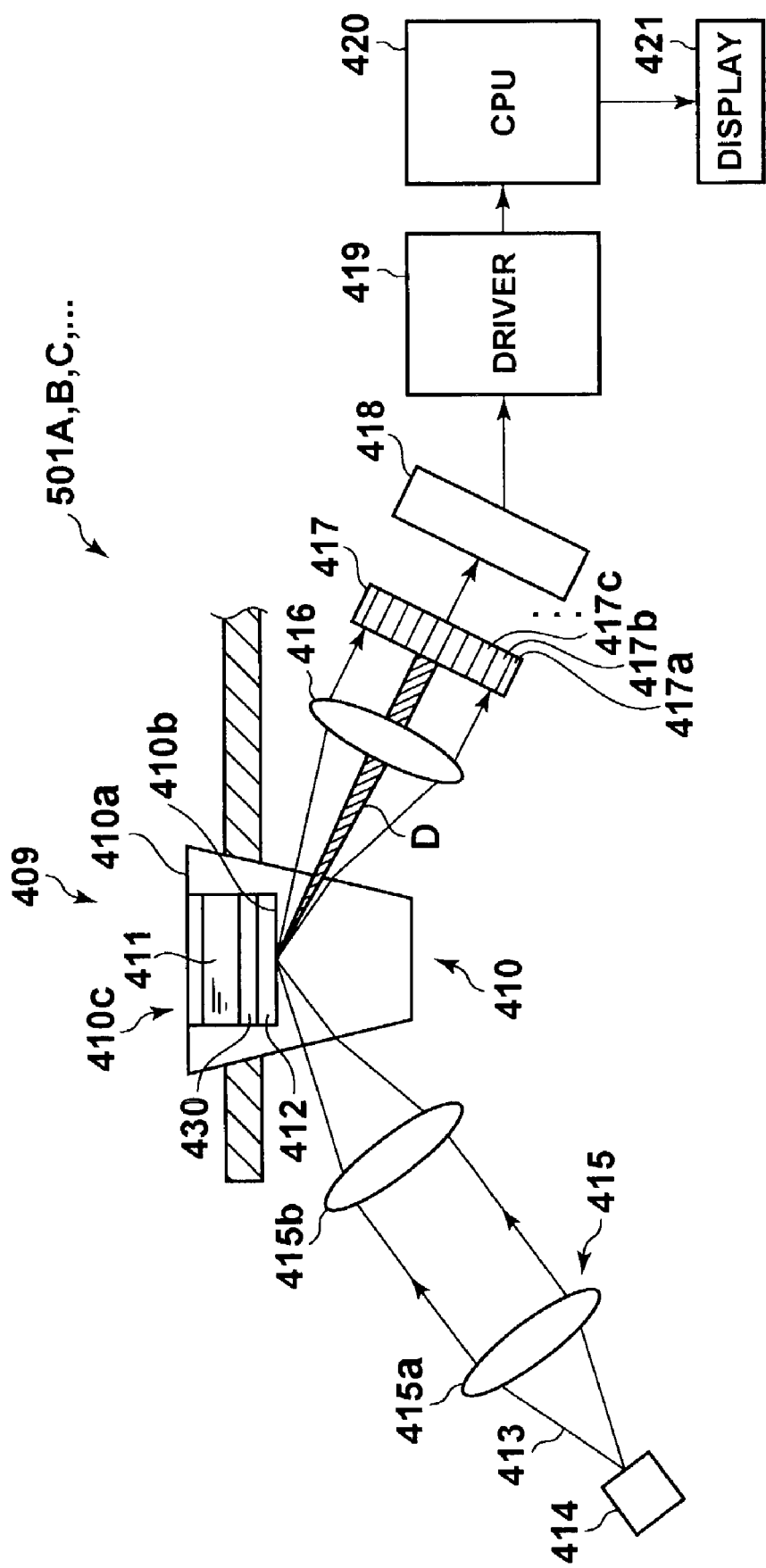
FIG. 19 is a side view of the surface plasmon resonance sensor of the twelfth embodiment.

As shown in FIG. 19, the laser beam 413 emitted from the laser 414 as a divergent light beam is converged on the interface 410b of the dielectric block 410 and the metal film 412 by the incident optical system 415.

The laser beam 413 reflected in total internal reflection at the interface 410b is detected by the photodetector means 417 after collimated by the collimator lens 416. In this particular embodiment, the photodetector means 417 is a photodiode array in which a plurality of photodiodes 417a, 417b, 417c . . . are arranged in a row in a direction substantially normal to the direction of travel of the collimated laser beam 413 in a plane of FIG. 18. That is, the components of the reflected laser beam 413 impinge upon different photodiodes 417a, 417b, 417c . . . .

A component of the laser beam 413 impinging upon the interface 410b at a particular angle of incidence θsp excites surface plasmon in the interface 410b between the metal film 412 and a material in contact with the metal film 412 and the intensity I of the component reflected in total internal reflection at the interface 410b sharply drops. That is, the particular angle of incidence is the attenuation angle θsp and the intensity I of the reflected laser beam 413 is minimized at the attenuation angle θsp. The sharp drop of the reflected laser beam 413 is observed as a dark line as indicated at D in FIG. 19.

Processing of signals output from the photodetector means 417 which represents the intensity distribution of the reflected laser beam 413 will be described in detail, hereinbelow.

FIG. 21 is a block diagram showing the electrical arrangement of the surface plasmon resonance sensor of this embodiment. As shown in FIG. 21, the driver 419 comprises sample hold circuits 422a, 422b, 422c . . . which sample-hold the outputs of the respective differential amplifiers 418a, 418b, 418c . . . of the differential amplifier array 418, a multiplexer 423 into which the outputs of the sample hold circuits 422a, 422b, 422c . . . are input, an A/D convertor 424 which digitizes the outputs of the multiplexer 423 and inputs them into the signal processing section 420, a drive circuit 425 which drives the multiplexer 423 and the sample hold circuits 422a, 422b, 422c . . . , and a controller 426 which controls the drive circuit 425 under the control of the signal processing section 420.

The outputs of adjacent pairs of the photodiodes 417a, 417b, 417c . . . are respectively input into the differential amplifiers 418a, 418b, 418c . . . of the differential amplifier array 418. Accordingly, the outputs of the differential amplifiers 418a, 418b, 418c . . . of the differential amplifier array 418 represent differentials of the outputs of the photodiodes 417a, 417b, 417c . . . (representing the intensities of light which they detect) in the direction in which the photodiodes 417a, 417b, 417c . . . are arranged.

The outputs of the differential amplifiers 418a, 418b, 418c . . . are sample-held at predetermined timings by the respective sample hold circuits 422a, 422b, 422c . . . and input into the multiplexer 423. The multiplexer 423 inputs the outputs of the respective sample hold circuits 422a, 422b, 422c . . . into the A/D convertor 424 in a predetermined order. The A/D convertor 424 digitizes the outputs of the respective sample hold circuits 422a, 422b, 422c . . . and inputs them into the signal processing section 420.

Figure 22A:
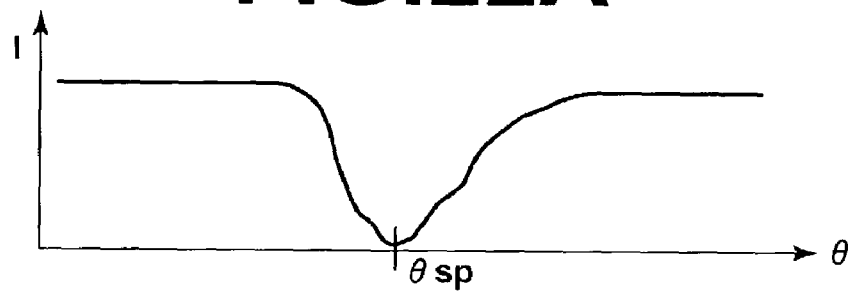
FIG. 22A is a view showing an example of the relation between the intensity I of the component of the laser beam reflected in total internal reflection at the interface and the angle of incidence θ of the component.

FIG. 22A shows an example of the relation between the intensity I of the component of the laser beam 413 reflected in total internal reflection at the interface 410b and the angle of incidence θ of the component.

Figure 22B:
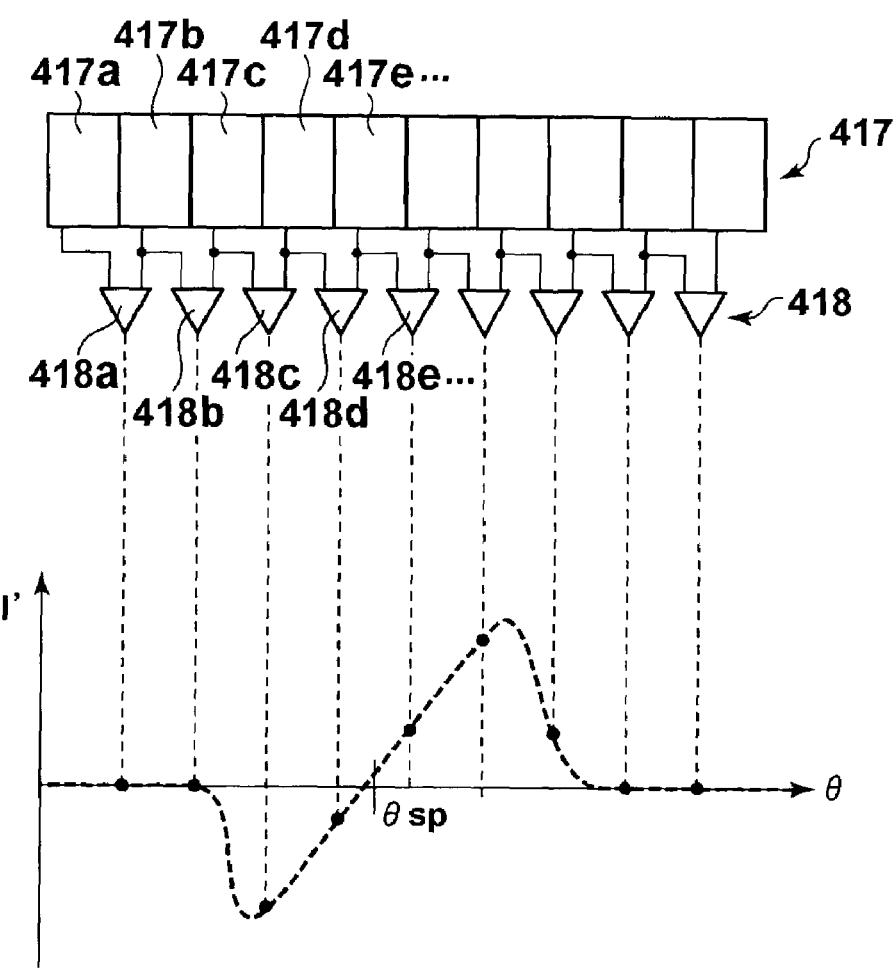
FIG. 22B is a view showing the relation between the output I' of the differential amplifier and the angle of incidence θsp.

As shown in FIG. 22B, the positions of the photodiodes 417a, 417b, 417c . . . in the direction in which they are arranged are one-to-one correspondence with the angle of incidence θsp. FIG. 22B also shows the relation between the output I' of the differential amplifier (the differential of the intensities I of the reflected laser beam 413) and the position of the photodiode 417a, 417b, 417c . . . in the direction in which the photodiodes are arranged (or the angle of incidence θsp).

The signal processing section 420 selects one of the differential amplifiers 418a, 418b, 418c . . . whose output I' is positive and the closest to 0 corresponding to the attenuation angle θsp (the differential amplifier 418e in the particular example shown in FIG. 22B) and one of the differential amplifiers 418a, 418b, 418c . . . whose output I' is negative and the closest to 0 corresponding to the attenuation angle θsp (the differential amplifier 18d in the particular example shown in FIG. 22B) on the basis of the differentials I' input into the A/D convertor 424. Then the signal processing section 420 calculates the attenuation angle θsp on the basis of the differential amplifiers. Sometimes there is a differential amplifier whose output I' is just 0. Naturally, the differential amplifier is selected in this case. Each time a predetermined time lapses, the signal processing section 420 repeatedly calculates the attenuation angle θsp and causes the display 421 to display the amount of change of the attenuation angle θsp from the initiation of the measurement.

Since the attenuation angle θsp changes with change of the dielectric constant or the refractive index of the material in contact with the metal film 412 of the measuring chip, change with time of the refractive index of the material in contact with the metal film 412 can be detected by detecting change of the attenuation angle θsp.

Figure 23A:
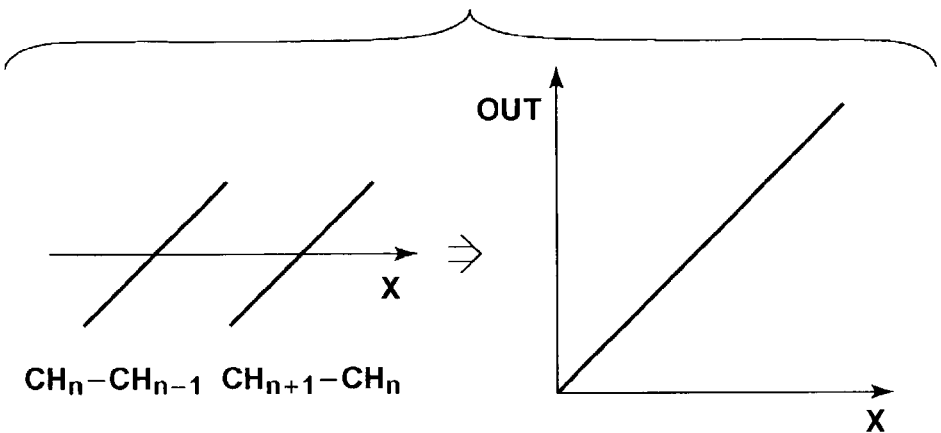
FIGS. 23A to 23C are views showing the relation between the sensitivities of the photodiodes and the outputs of the signal processing section for illustrating a problem in a measuring apparatus not in accordance with the present invention.
Figure 23B:
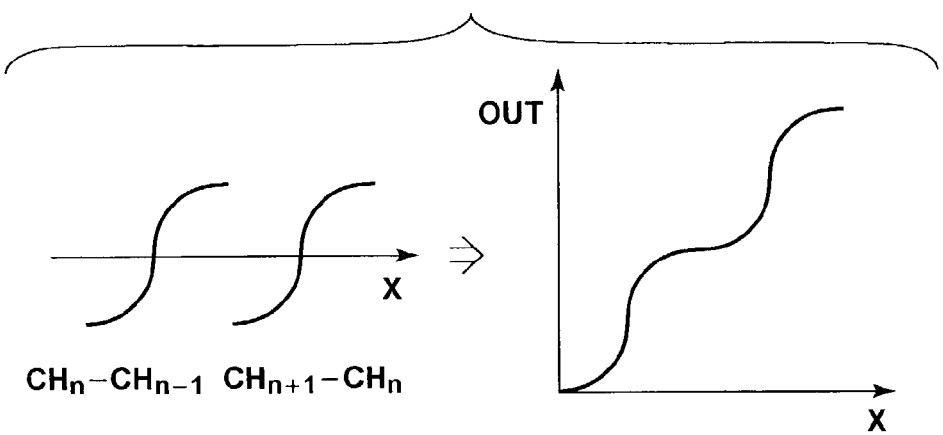
Figure 23C:
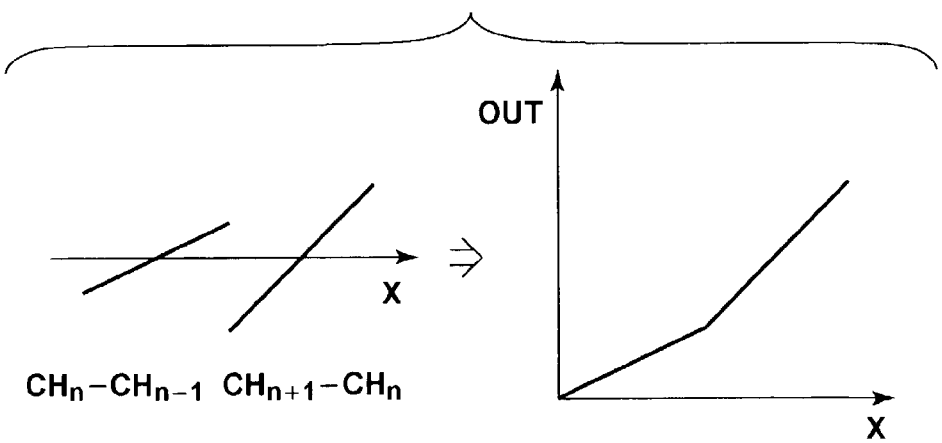

When the photodiodes 417a, 417b, 417c . . . of the photodetector means 417 are all linear and uniform in sensitivity characteristics as shown in the left part of FIG. 23A, the relation between the real position of the dark line and the position of the dark line calculated is an optimal linear as shown in the right part of FIG. 23A. Whereas, when the photodiodes 417a, 417b, 417c . . . of the photodetector means 417 are non-linear in sensitivity characteristics as shown in the left part of FIG. 23B, the relation between the real position of the dark line and the position of the dark line calculated waves as shown in the right part of FIG. 23B, and when the photodiodes 417a, 417b, 417c . . . of the photodetector means 417 are non-uniform in sensitivity characteristics as shown in the left part of FIG. 23C, the relation between the real position of the dark line and the position of the dark line calculated is non-linear as shown in the right part of FIG. 23C.

Figure 24:
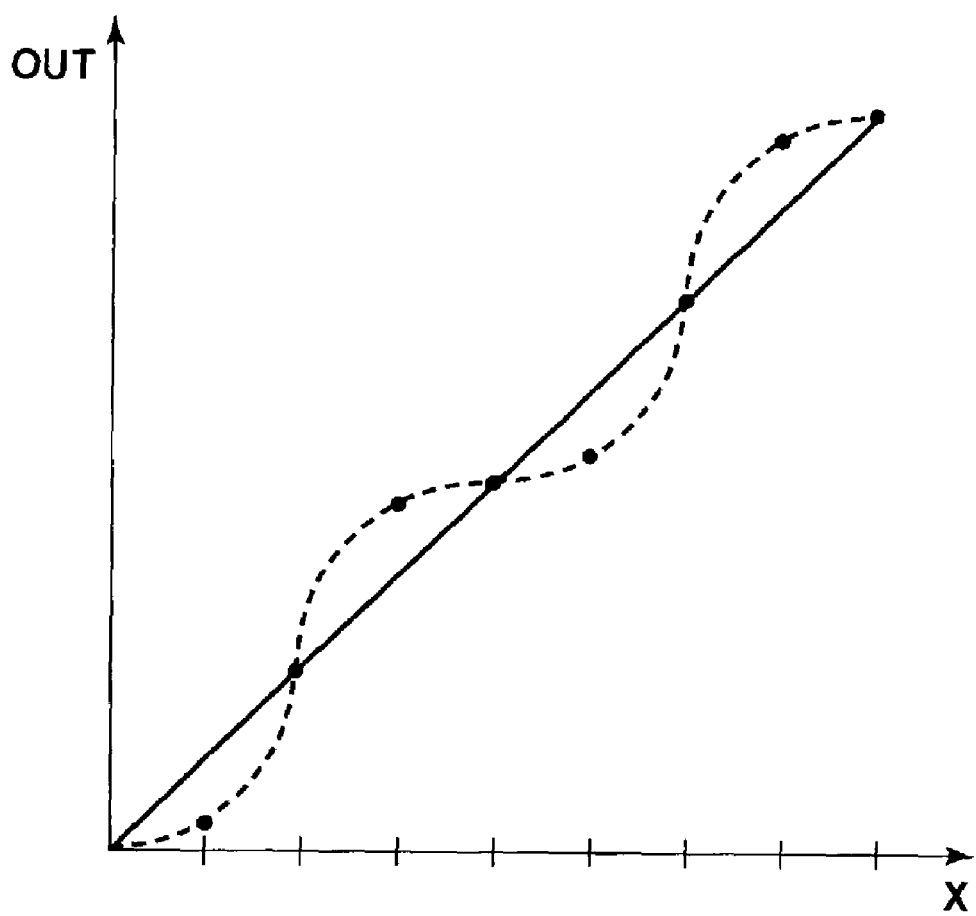
FIG. 24 is a view for illustrating smoothing of the output characteristics of the signal processing section in accordance with the present invention.

In the surface plasmon resonance sensor of this embodiment, the intensities of the laser beam 413 reflected in total internal reflection at the interface 410 are measured a plurality of times in a time series, a plurality of pieces of measured data obtained are stored in a memory (not shown) of the signal processing section 420, the plurality of pieces of measured data are smoothed by least square method as shown in FIG. 24 and the sample is analyzed on the basis of the smoothed pieces of measured data. The plurality of pieces of measured data may be smoothed by any method other than least square method.

By setting a proper threshold value to the output of the differential amplifier connected to each photodetector elements according to the sensitivity properties of the photodetector element and by switching to the next channel before the output characteristics of the differential amplifier exceeds its linear range, that is, by using only the range where the output characteristics of the differential amplifier is linear, the measuring errors due to the sensitivity characteristics of the photodetector elements can be suppressed.

When a sensing medium 430 which combines with a particular material in the sample liquid 411 is fixed on the metal film 412, the refractive index of the sensing medium 430 changes depending on the state of combination of the sensing medium 430 and the particular material, change of the state of combination of the sensing medium 430 and the particular material can be detected by keeping measuring the differential value I'. In this case, both the sample liquid 411 and the sensing medium 430 are the object of analysis. As combinations of such a specific material and a sensing material, for instance, combinations of an antigen and an antibody have been known.

The surface plasmon resonance sensor of this embodiment can be modified to a leaky mode sensor by changing a part thereof.

Figure 25:
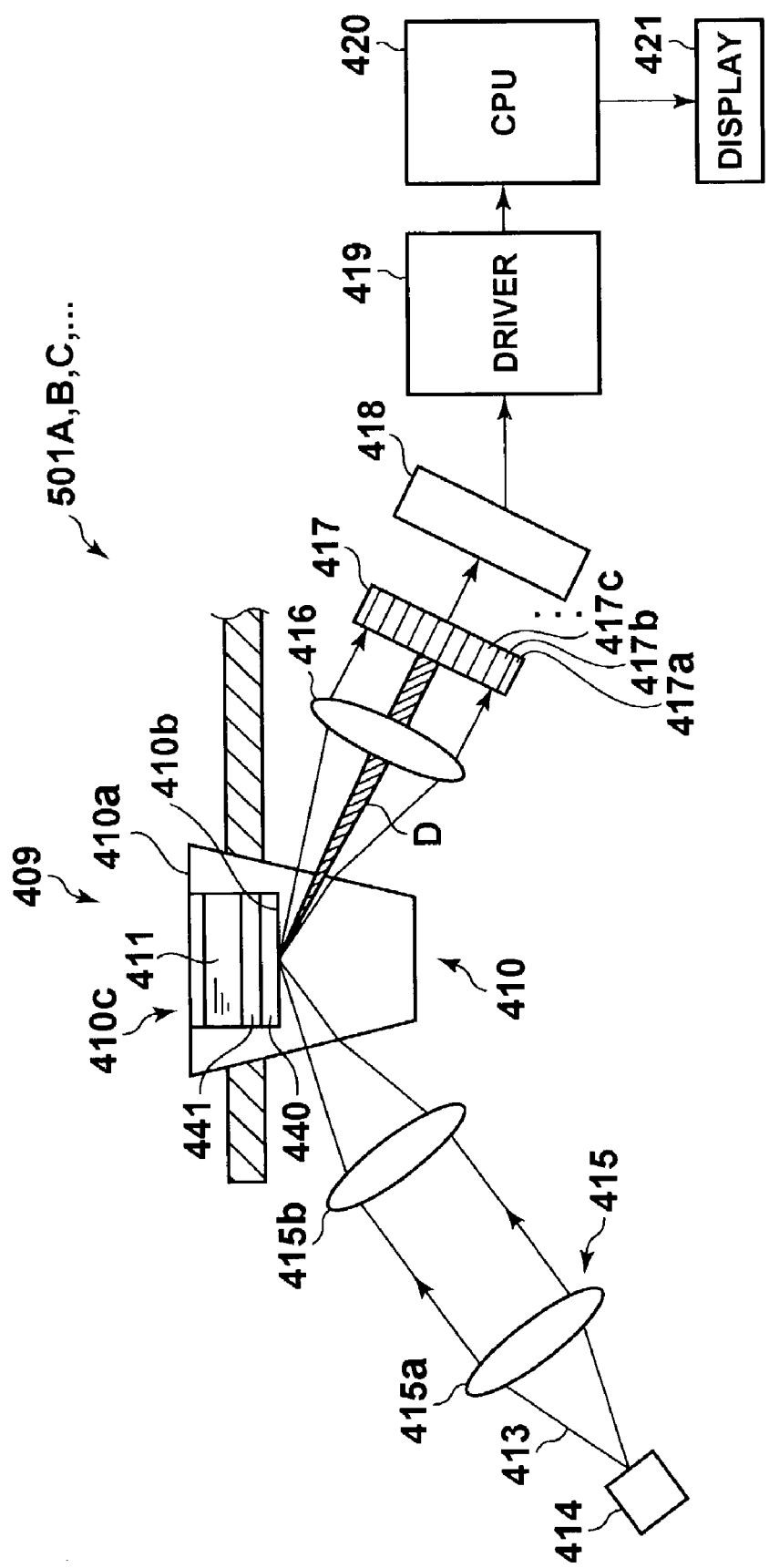
FIG. 25 is a side view of a leaky mode resonance sensor in accordance with a thirteenth embodiment of the present invention.

FIG. 25 shows a leaky mode sensor in accordance with a thirteenth embodiment of the present invention. In FIG. 25, elements analogous to those shown in FIG. 19 are given the same reference numerals and will not be described here unless otherwise necessary.

The measuring apparatus of the thirteenth embodiment is substantially the same as that of the twelfth embodiment except that the former is a leaky mode sensor and the latter is a surface plasmon resonance sensor. That is, in the leaky mode sensor of the thirteenth embodiment, the dielectric block 410 is formed of synthetic resin or optical glass (e.g., BK7), and a clad layer 440 is formed on one face of the dielectric block 410 and an optical waveguide layer 441 is formed on the clad layer 440.

The clad layer 440 is in the form of film of dielectric material or metal (e.g., gold) which is lower in refractive index than the dielectric block 410. The optical waveguide layer 441 is in the form of film of dielectric material which is higher in refractive index than the clad layer 440 (e.g., PMMA). For example, the clad layer 440 is 36.5 nm in thickness when it is in the form of a metal film and the optical waveguide layer 441 is 700 nm in thickness when it is formed of PMMA.

In the leaky mode sensor with this arrangement, when the laser beam 413 emitted from the laser 414 is caused to impinge upon the clad layer 440 through the dielectric block 410 at an angle not smaller than an angle of total internal reflection, only light having a particular wave number and impinging upon the optical waveguide layer 441 at a particular angle of incidence comes to propagate through the optical waveguide layer 441 in a waveguide mode after passing through the clad layer 440. When the waveguide mode is thus excited, almost all the incident light is taken in the optical waveguide layer 441 and accordingly, the intensity of light reflected in total internal reflection at the interface 410 of the dielectric block 410 and the clad layer 440 sharply drops. That is, attenuation in total internal reflection occurs.

Since the wave number of light to be propagated through the optical waveguide layer 441 in a waveguide mode depends upon the refractive index of the sample liquid 411 on the optical waveguide layer 441, the refractive index and/or the properties of the sample liquid 411 related to the refractive index can be detected on the basis of the angle of incidence at which the attenuation in total internal reflection occurs.

Figure 26:
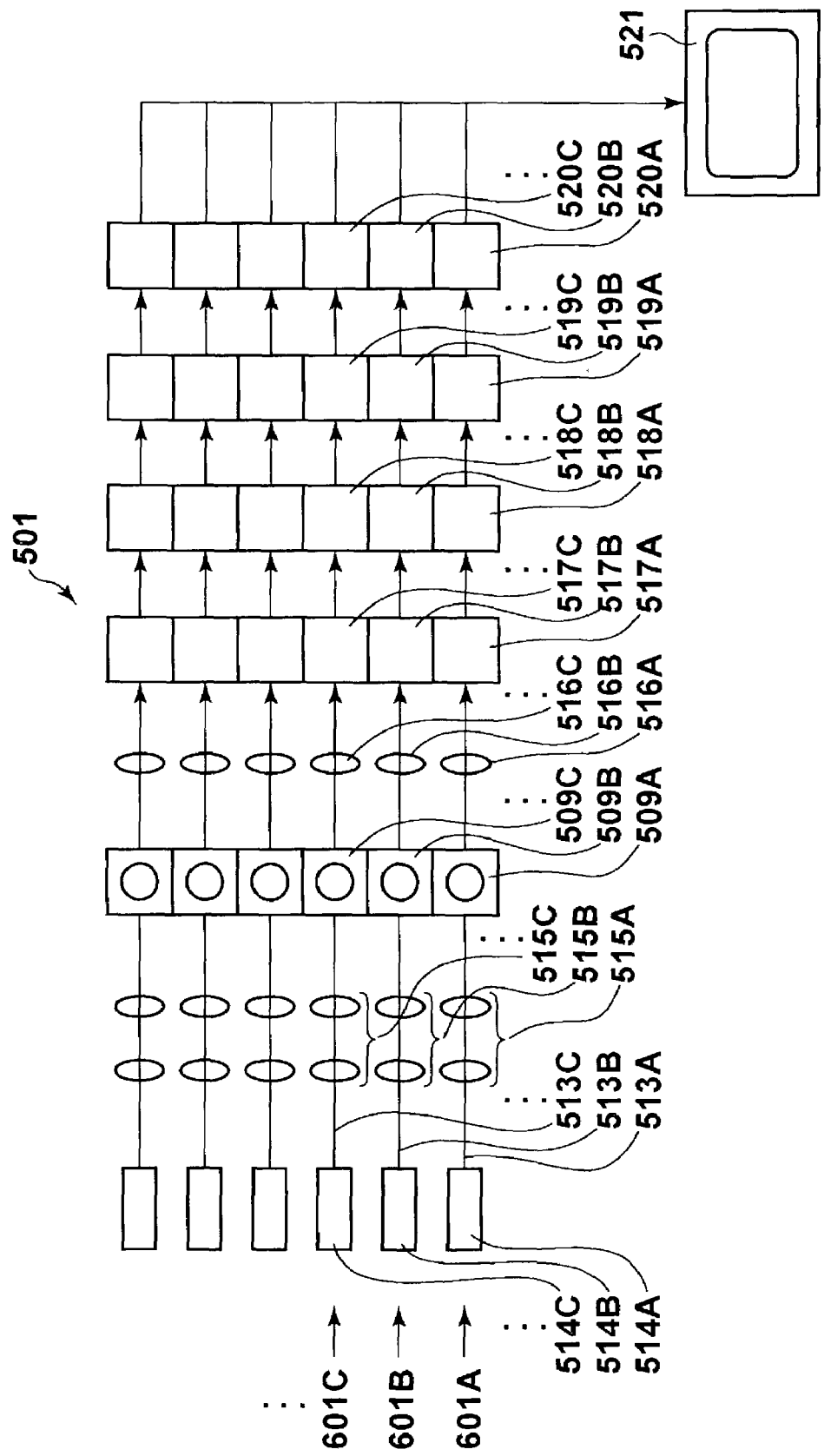
FIG. 26 is a plan view showing a surface plasmon resonance sensor in accordance with a fourteenth embodiment of the present invention.

FIG. 26 shows a surface plasmon resonance sensor in accordance with a twelfth embodiment of the present invention. The surface plasmon resonance sensor 501 is provided with a plurality of measuring units 601A, 601B, 601C . . . of the same structure and can analyze a plurality of samples at one time.

The measuring units will be described, hereinbelow, with the suffixed alphabet (e.g., A, B, C) removed from the reference numerals of the respective elements. Each measuring unit 601 comprises a measuring chip 509, a laser source 514 which emits a laser beam 513, an incident optical system 515 which causes the laser beam 513 to impinge upon an interface 510b between a dielectric block 512 (to be described later) and a metal film 512 (to be described later), a collimator lens 516 which converts the laser beam 513 reflected in total internal reflection at the interface 510b into a parallel laser beam, a photodetector means 517 which detects the intensity of the parallel laser beam 513, a differential amplifier array 518 connected to the photodetector means 517, a driver 519 connected to the differential amplifier array 518, a signal processing section (CPU) 520 which may comprise, for instance, a computer system and is connected to the driver 519 and an A/D convertor 527 which digitizes the output signals from the photodetector means 517 and inputs them to the signal processing section 520. The differential amplifier array 518, the driver 519 and the signal processing section 520 form the operation means.

Figure 28:
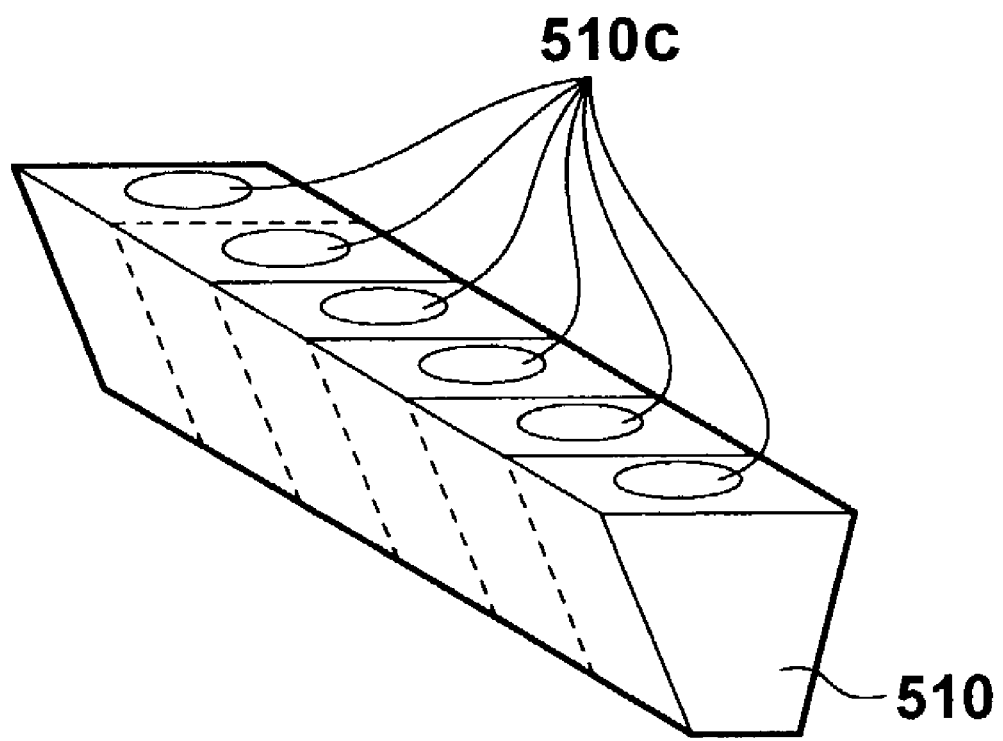
FIG. 28 is a view showing in detail the measuring chips employed in the surface plasmon resonance sensor of the fourteenth embodiment.

The measuring chip 509 comprises a dielectric block 510 which is like a truncated pyramid in shape and a metal film 512 of gold, silver, copper, aluminum or the like is formed on one face of the dielectric block 510. The dielectric block 510 is formed, for instance, of transparent synthetic resin and the metal film 512 is provided on the bottom of a recessed portion 510a, which functions as a sample holding well for holding a sample liquid 511. A sensing medium 530 may be fixed on the metal film 512. The dielectric blocks 510 of measuring chips of a plurality of measuring units are integrated as shown in FIG. 28.

The incident optical system 515 comprises a collimator lens 515a which converts the laser beam 513, emitted from the laser 514 as a divergent light beam, into a parallel laser beam, and a condenser lens 515b which converges the collimated laser beam 513 on the interface 510b.

Since converged by the condenser lens 515b as described above, the laser beam 513 includes components impinging upon the interface at various angles of incidence θ. The laser 514 and the incident optical system 515 are arranged so that the angles of incidence θ are all not smaller than the angle of total internal reflection. Accordingly, the laser beam 513 is reflected in total internal reflection at the interface 510b and the reflected laser beam 513 includes components reflected at the interface 510b at various angles of reflection. The incident optical system 515 may be arranged to cause the laser beam 513 to impinge upon the interface 510b in a defocused state. This arrangement causes the laser beam 513 to be reflected at the interface 510b over a wider area thereof and averages errors in detecting states of surface plasmon resonance and improves measuring accuracy.

The laser beam 513 is caused to impinge upon the interface 510b in a p-polarized state. This can be realized by positioning the laser 514 so that the laser beam 513 impinges upon the interface 510b in a p-polarized state. Otherwise, the direction of polarization of the laser beam 513 may be controlled by a wavelength plate. The surface plasmon resonance sensor 501 of this embodiment further comprises a display 521 connected to the signal processing sections 520A, 520B, 520C . . . of the measuring units.

Figure 27:
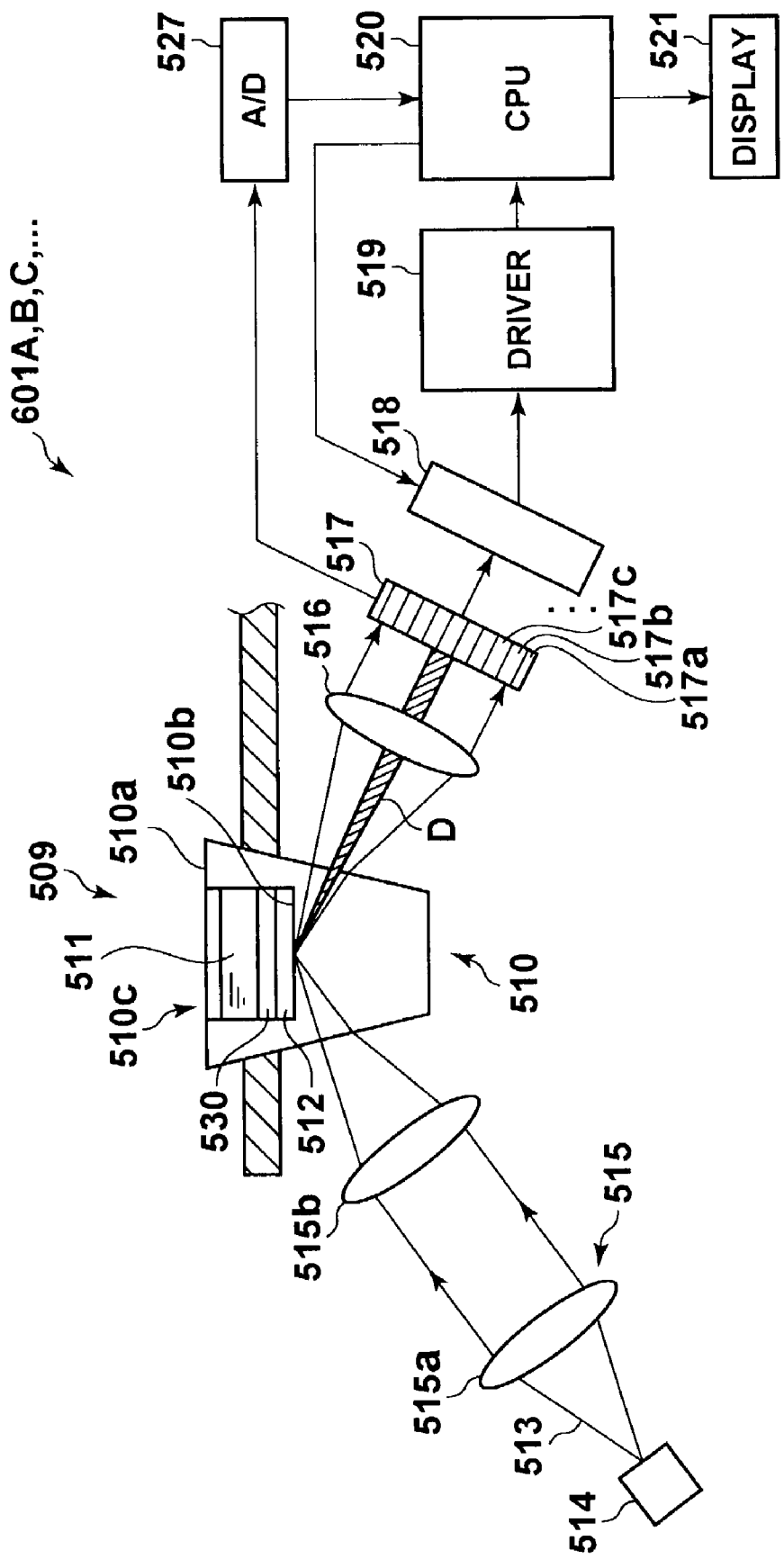
FIG. 27 is a side view of the surface plasmon resonance sensor of the fourteenth embodiment.

Analysis of a sample by the surface plasmon resonance sensor of this embodiment will be described, hereinbelow. As shown in FIG. 27, the laser beam 513 emitted from the laser 514 as a divergent light beam is converged on the interface 510b of the dielectric block 510 and the metal film 512 by the incident optical system 515.

The laser beam 513 reflected in total internal reflection at the interface 510b is detected by the photodetector means 517 after collimated by the collimator lens 516. The photo detector means 517 is a photodiode array in which a plurality of photodiodes 517a, 517b, 517c . . . are arranged in a row in a direction substantially normal to the direction of travel of the collimated laser beam 513 in a plane substantially parallel to that of FIG. 27. That is, the components of the reflected laser beam 513 impinge upon different photodiodes 517a, 517b, 517c . . . . The photodetector means 517 outputs a signal representing the intensity distribution of the reflected laser beam 513 as detected by the photodiodes 517a, 517b, 517c . . . to the differential amplifier array 518 and the A/D convertor 527. The A/D convertor 527 digitizes the signal and inputs the digitized signal into the signal processing section 520.

A component of the laser beam 513 impinging upon the interface 510b at a particular angle of incidence θsp excites surface plasmon in the interface 510b between the metal film 512 and a material in contact with the metal film 512 and the intensity I of the component reflected in total internal reflection at the interface 510b sharply drops. That is, the particular angle of incidence is the attenuation angle θsp and the intensity I of the reflected laser beam 513 is minimized at the attenuation angle θsp. The sharp drop of the reflected laser beam 513 is observed as a dark line as indicated at D in FIG. 27.

Figure 29:
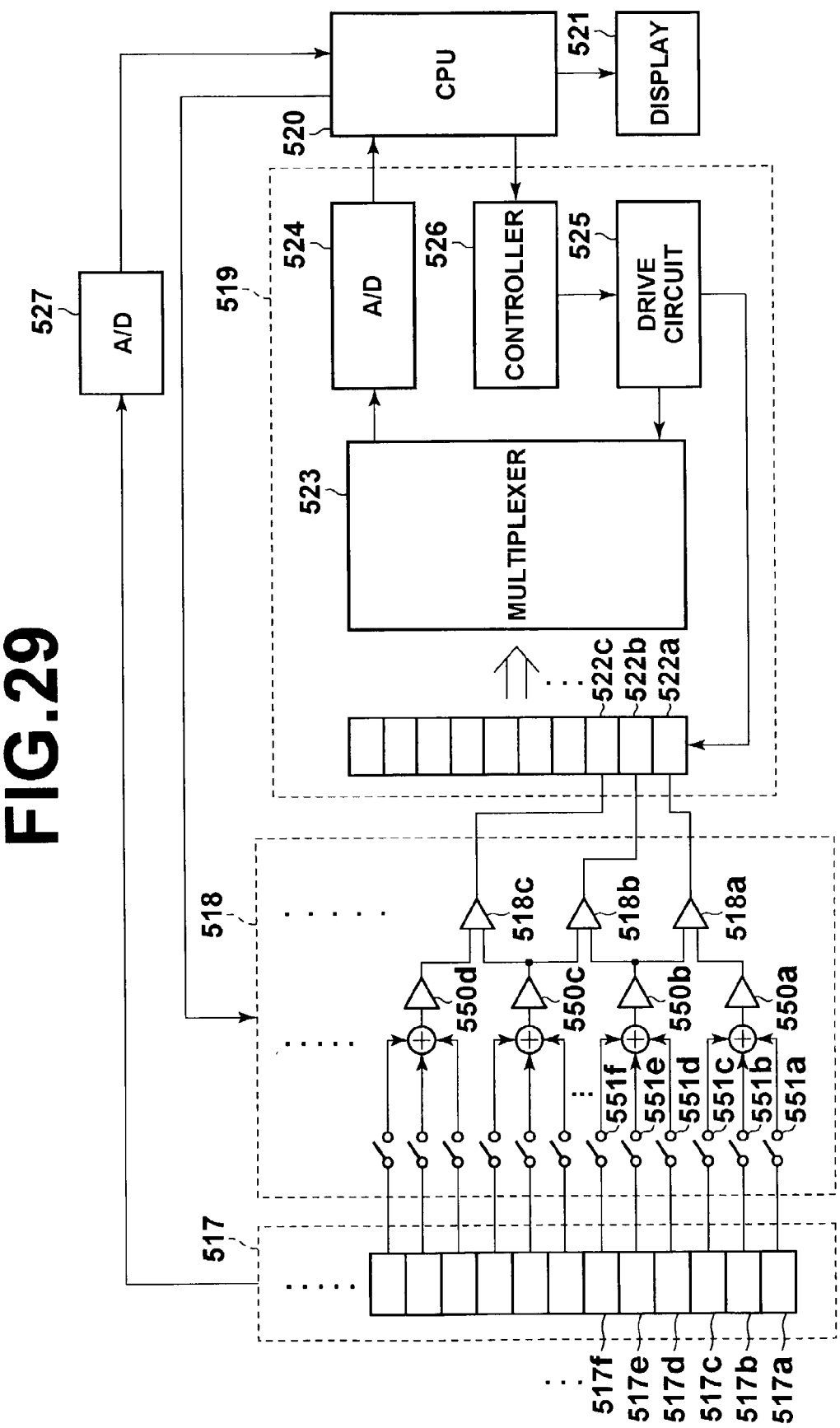
FIG. 29 is a block diagram showing the electrical arrangement of the surface plasmon resonance sensor of the fourteenth embodiment.

Processing of signals output from the photodetector means 517 which represents the intensity distribution of the reflected laser beam 513 will be described in detail, hereinbelow. FIG. 29 is a block diagram showing the electrical arrangement of the surface plasmon resonance sensor of this embodiment. As shown in FIG. 29, the differential amplifier array 518 comprises a plurality of switches 551a, 551b, 551c . . . respectively connected to the photodiodes 517a, 517b, 517c . . . , a plurality of adders 550a, 550b, 550c . . . each of which is connected to the outputs of adjacent three switches, and a plurality of differential amplifiers 518a, 518b, 518c . . . each of which is connected to the outputs of adjacent two adders. That is, in this particular embodiment, three photodiodes form one photodiode group. The switches 551a, 551b, 551c . . . are opened and closed under the control of the signal processing section 520.

Further, the driver 519 comprises sample hold circuit 522a, 522b, 522c . . . which sample-hold the outputs of the respective differential amplifiers 518a, 518b, 518c . . . of the differential amplifier array 518, a multiplexer 523 into which the outputs of the sample hold circuits 522a, 522b, 522c . . . are input, an A/D convertor 524 which digitizes the outputs of the multiplexer 523 and inputs them into the signal processing section 520, a drive circuit 525 which drives the multiplexer 523 and the sample hold circuits 522a, 522b, 522c . . . , and a controller 526 which controls the drive circuit 525 under the control of the signal processing section 520.

The outputs of adjacent three the photodiodes 517a, 517b, 517c . . . are added by the respective adders 550a, 550b, 550c . . . and the outputs of adjacent two adders are respectively input into the differential amplifiers 518a, 518b, 518c . . . of the differential amplifier array 518. Accordingly, the outputs of the differential amplifiers 518a, 518b, 518c . . . of the differential amplifier array 518 represent differentials of the outputs of the photodiodes 517a, 517b, 517c . . . (representing the intensities of light which they detect) in the direction in which the photodiodes 517a, 517b, 517c . . . are arranged.

The outputs of the differential amplifiers 518a, 518b, 518c . . . are sample-held at predetermined timings by the respective sample hold circuits 522a, 522b, 522c . . . and input into the multiplexer 523. The multiplexer 523 inputs the outputs of the respective sample hold circuits 522a, 522b, 522c . . . into the A/D convertor 524 in a predetermined order. The A/D convertor 524 digitizes the outputs of the respective sample hold circuits 522a, 522b, 522c . . . and inputs them into the signal processing section 520.

Figure 30A:
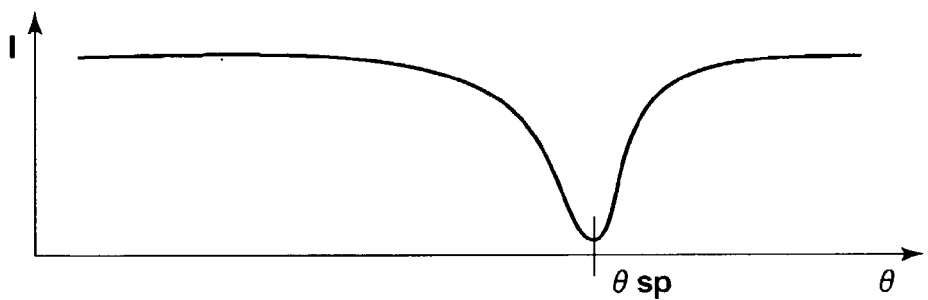
FIG. 30A is a view showing an example of the relation between the intensity I of the component of the laser beam reflected in total internal reflection at the interface and the angle of incidence θ of the component.

FIG. 30A shows an example of the relation between the intensity I of the component of the laser beam 513 reflected in total internal reflection at the interface 510b and the angle of incidence θ of the component.

Figure 30B:
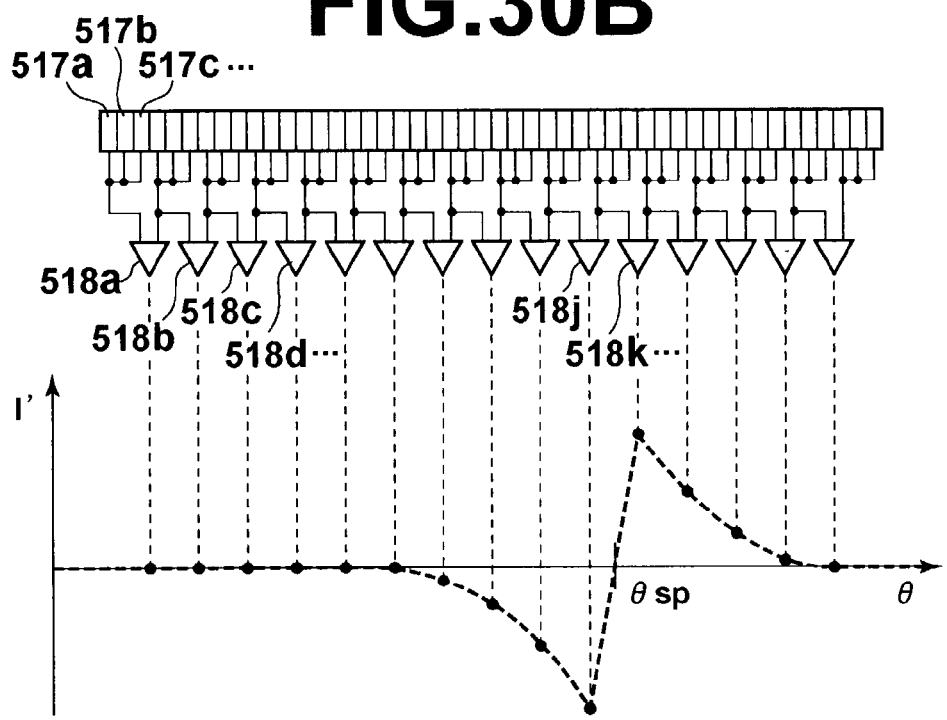
FIG. 30B is a view showing the relation between the output I' of the differential amplifier and the angle of incidence θsp.

As shown in FIG. 30B, the positions of the photodiodes 517a, 517b, 517c . . . in the direction in which they are arranged are one-to-one correspondence with the angle of incidence θsp. FIG. 30B also shows the relation between the output I' of the differential amplifier (the differential of the intensities I of the reflected laser beam 513) and the position of the photodiode 517a, 517b, 517c . . . in the direction in which the photodiodes are arranged (or the angle of incidence θsp).

Figure 30C:
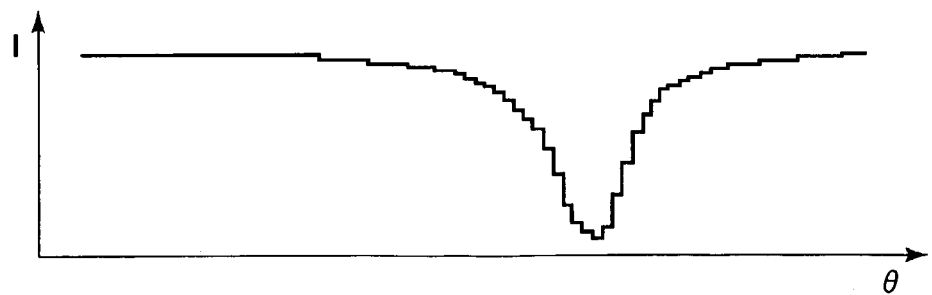
FIG. 30C is a view showing a beam profile represented by output signals of the photodiodes which are digitized by the A/D convertor and then input into the signal processing section.

FIG. 30C is a view showing a beam profile represented by output signals of the photodiodes 517a, 517b, 517c . . . which are digitized by the A/D convertor 527 and then input into the signal processing section 520.

The signal processing section 520 selects one of the differential amplifiers 518a, 518b, 518c . . . whose output I' is positive and the closest to 0 corresponding to the attenuation angle θsp (the differential amplifier 518 k in the particular example shown in FIG. 30B) and one of the differential amplifiers 518a, 518b, 518c . . . whose output I' is negative and the closest to 0 corresponding to the attenuation angle θsp (the differential amplifier 518j in the particular example shown in FIG. 30B) on the basis of the differentials I' input into the A/D convertor 524. Then the signal processing section 520 calculates the attenuation angle θsp on the basis of the differential amplifiers. Sometimes there is a differential amplifier whose output I' is just 0. Naturally, the differential amplifier is selected in this case. Each time a predetermined time lapses, the signal processing section 520 repeatedly calculates the attenuation angle θsp and causes the display 521 to display the amount of change of the attenuation angle θsp from the initiation of the measurement.

The signal processing section 520 calculates a beam profile such as shown in FIG. 30C on the signals input into the signal processing section 520 from the photodiodes 517a, 517b, 517c . . . by way of the A/D convertor 527 and causes the display 521 to display the beam profile together with the attenuation angle θsp. Since the signal processing section 520 generates the beam profile on the basis the outputs of the photodiodes 517a, 517b, 517c . . . , the beam profile can be generated at a resolution higher than that at which the attenuation angle θsp is calculated.

Though, in the embodiment described above, when the attenuation angle θsp is calculated, the outputs of all the photodiodes in each photodiode group are added, the attenuation angle θsp may be calculated on the basis of the outputs of one or two photodiodes in each photodiode group, for instance, by selectively opening and closing the switches 551a, 551b, 551c . . . .

Each photodiode group need not be of three photodiodes but may be of two photodiodes or four or more photodiodes.

Figure 31:
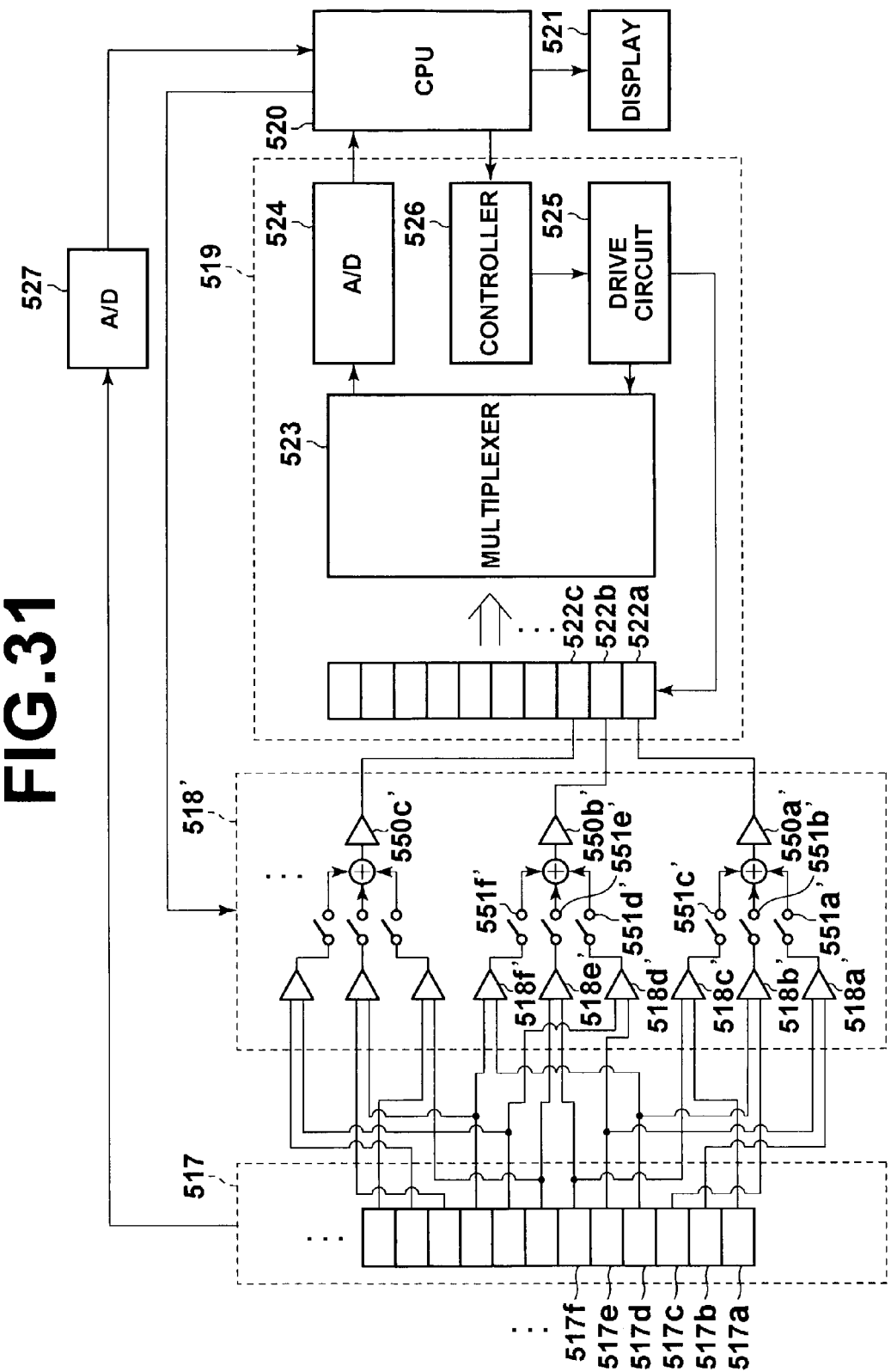
FIG. 31 is a block diagram showing a modification of the electrical arrangement of the surface plasmon resonance sensor of the fourteenth embodiment.

FIG. 31 shows a modification of the electrical arrangement of the surface plasmon resonance sensor of this embodiment. In FIG. 31, the elements analogous to those shown in FIG. 29 are given the same reference numerals and will not described here. Since the modification shown in FIG. 31 mainly differs from the electrical arrangement shown in FIG. 29 only in the structure of the differential amplifier array and connection to the photodetector means 517 thereof, only the differential amplifier array 518' will be described, hereinbelow.

The differential amplifier array 518' of this modification comprises a plurality of differential amplifiers 518a', 518b', 518c' . . . each connected to two of the photodiodes 517a, 517b, 517c . . . , a plurality of switches 551a', 551b', 551c' . . . each connected to one of the differential amplifiers 518a', 518b', 518c' . . . and a plurality of adders 550a', 550b', 550c' . . . each connected to three of the switches 551a', 551b', 551c' . . . .

The two photodiodes, one in one of two adjacent groups the other in the other group and the two photodiodes being at the largest distance from each other in the two adjacent groups (e.g., the photodiodes 517a and 517f), are connected to the differential amplifier 518c', the two photodiodes, one in one of two adjacent groups the other in the other group and the two photodiodes being at the intermediate distance from each other in the two adjacent groups (e.g., the photodiodes 517b and 517e), are connected to the differential amplifier 518b', and the two photodiodes, one in one of two adjacent groups the other in the other group and the two photodiodes being at the smallest distance from each other in the two adjacent groups (e.g., the photodiodes 517c and 517d), are connected to the differential amplifier 518a'.

That is, in the electrical arrangement shown in FIG. 29, the sum of the outputs of photodiodes in each of adjacent two photodiode groups is first taken and the difference between the sums of the adjacent two photodiode groups is taken as the differential for the two adjacent photodiode groups, whereas, in the electrical arrangement shown in FIG. 31, the difference between the outputs of two photodiodes in each of adjacent two photodiode groups is first taken and the sum of the differences is taken as the differential for the two adjacent photodiode groups.

Similarly to the case where the differential amplifier array 518 shown in FIG. 28 is employed, the attenuation angle θsp may be calculated on the basis of the outputs of one or two photodiodes in each photodiode group, for instance, by selectively opening and closing the switches 551a', 551b', 551c'.... For example, in the case where the amount of light detected by each of the photodiodes is sufficient or in the case where the dark line generated in the reflected laser beam 513 is small in width, the attenuation angle θsp may be calculated on the basis of only the difference between the outputs of a pair of photodiodes in adjacent two photodiode groups, whereas in the case where the amount of light detected by each of the photodiodes is insufficient or in the case where the dark line generated in the reflected laser beam 513 is large in width, it is preferred that the attenuation angle θsp be calculated on the basis of the differences between the outputs of all the photodiodes in adjacent two photodiode groups. With this arrangement, the attenuation angle θsp can be calculated more accurately. Further when the differentials are obtained by the use of an analog circuit such as a differential amplifier array 518 or 518', generation of sampling noise due to digital adding can be suppressed.

Since the attenuation angle θsp changes with change of the dielectric constant or the refractive index of the material in contact with the metal film 512 of the measuring chip, change with time of the refractive index of the material in contact with the metal film 512 can be detected by detecting change of the attenuation angle θsp.

When the sensing medium 530 which combines with a particular material in the sample liquid 511 is fixed on the metal film 512, the refractive index of the sensing medium 530 changes depending on the state of combination of the sensing medium 530 and the particular material, change of the state of combination of the sensing medium 530 and the particular material can be detected by keeping measuring the differential value I'. In this case, both the sample liquid 511 and the sensing medium 530 are the object of analysis. As combinations of such a specific material and a sensing material, for instance, combinations of an antigen and an antibody have been known.

Figure 32:
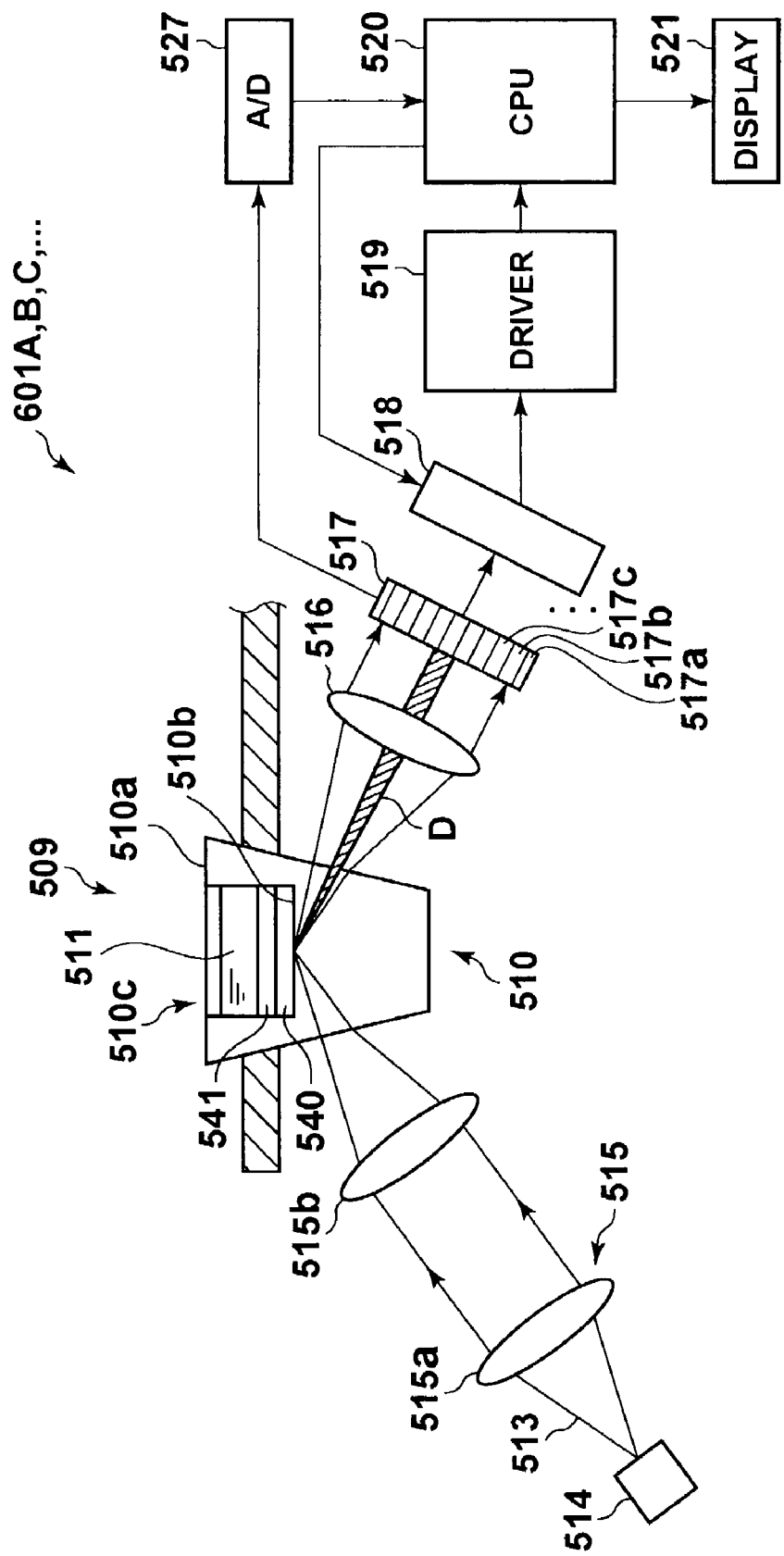
FIG. 32 is a side view of the leaky mode sensor in accordance with a fifteenth embodiment of the present invention.

The surface plasmon resonance sensor of this embodiment can be modified to a leaky mode sensor by changing a part thereof. FIG. 32 shows a leaky mode sensor in accordance with a fifteenth embodiment of the present invention. In FIG. 32, elements analogous to those shown in FIG. 27 are given the same reference numerals and will not be described here unless otherwise necessary.

The measuring apparatus of the fifteenth embodiment is substantially the same as that of the fourteenth embodiment except that the former is a leaky mode sensor and the latter is a surface plasmon resonance sensor. That is, in the leaky mode sensor of the fifteenth embodiment, the dielectric block 510 is formed of synthetic resin or optical glass (e.g., BK7), and a clad layer 540 is formed on one face of the dielectric block 510 and an optical waveguide layer 541 is formed on the clad layer 540.

The clad layer 540 is in the form of film of dielectric material or metal (e.g., gold) which is lower in refractive index than the dielectric block 510. The optical waveguide layer 541 is in the form of film of dielectric material which is higher in refractive index than the clad layer 540 (e.g., PMMA). For example, the clad layer 540 is 36.5 nm in thickness when it is in the form of a metal film and the optical waveguide layer 541 is 700 nm in thickness when it is formed of PMMA.

In the leaky mode sensor with this arrangement, when the laser beam 513 emitted from the laser 514 is caused to impinge upon the clad layer 540 through the dielectric block 510 at an angle not smaller than an angle of total internal reflection, only light having a particular wave number and impinging upon the optical waveguide layer 541 at a particular angle of incidence comes to propagate through the optical waveguide layer 541 in a waveguide mode after passing through the clad layer 540. When the waveguide mode is thus excited, almost all the incident light is taken in the optical waveguide layer 541 and accordingly, the intensity of light reflected in total internal reflection at the interface 510 of the dielectric block 510 and the clad layer 540 sharply drops. That is, attenuation in total internal reflection occurs.

Since the wave number of light to be propagated through the optical waveguide layer 541 in a waveguide mode depends upon the refractive index of the sample liquid 511 on the optical waveguide layer 541, the refractive index and/or the properties of the sample liquid 511 related to the refractive index can be detected on the basis of the angle of incidence at which the attenuation in total internal reflection occurs.

Figure 33:
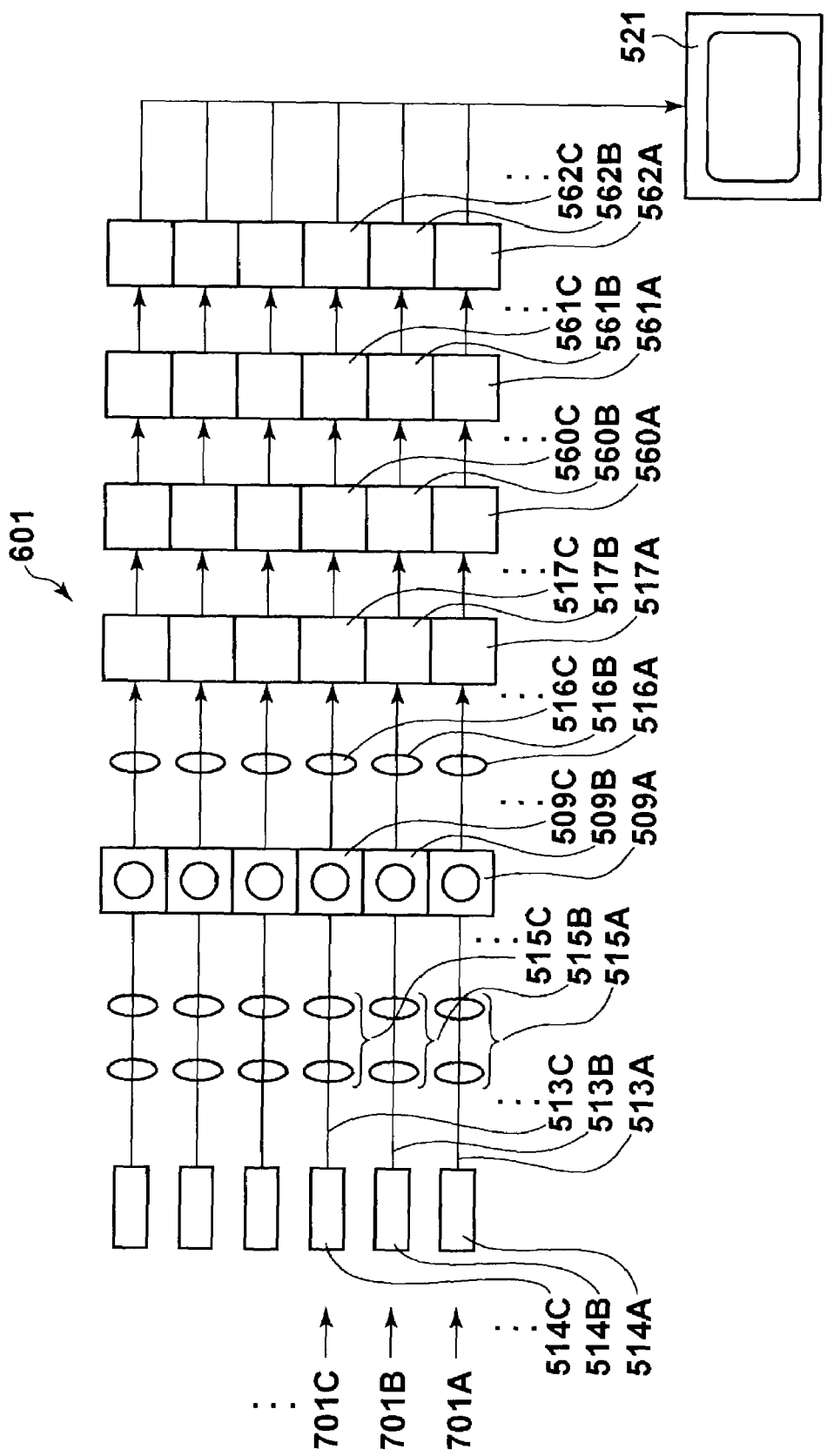
FIG. 33 is a plan view showing a surface plasmon resonance sensor in accordance with a sixteenth embodiment of the present invention.
Figure 34:
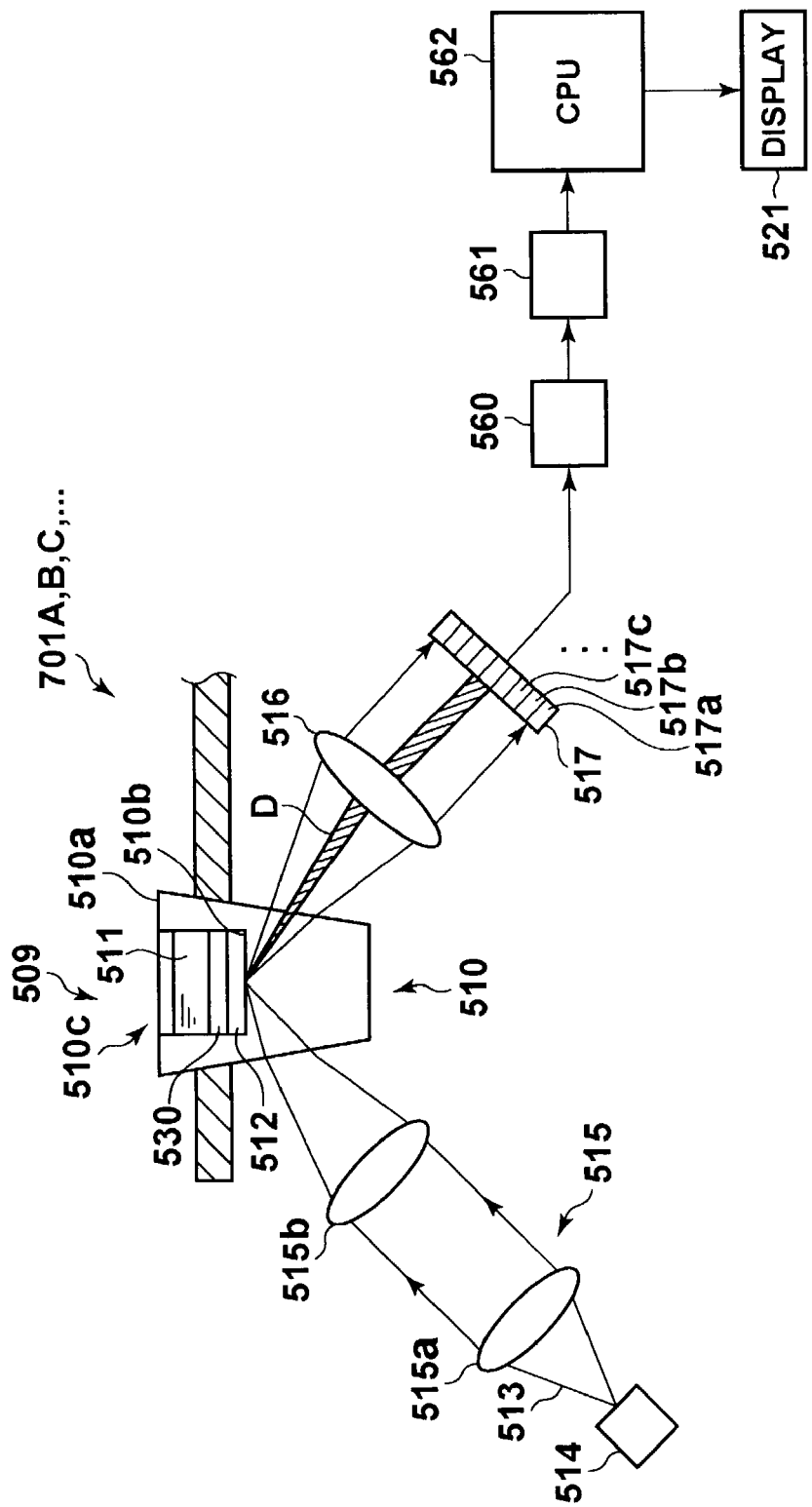
FIG. 34 is a side view of the surface plasmon resonance sensor of the sixteenth embodiment.

FIGS. 33 and 34 show a surface plasmon resonance sensor in accordance with a sixteenth embodiment of the present invention. In FIGS. 33 and 34, elements analogous to those shown in FIGS. 26 and 27 are given the same reference numerals and will not be described here unless otherwise necessary. The surface plasmon resonance sensor 601 pf this embodiment is provided with a plurality of measuring units 701A, 701B, 701C . . . of the same structure and can analyze a plurality of samples at one time.

The measuring units will be described, hereinbelow, with the suffixed alphabet (e.g., A, B, C) removed from the reference numerals of the respective elements. Each measuring unit 701 comprises a measuring chip 509, a laser source 514 which emits a laser beam 513, an incident optical system 515, a collimator lens 516, a photodetector means 517, an A/D convertor 560, an operating section 561, a signal processing section (CPU) 520 which may comprise, for instance, a computer system. The operating section 561 and the signal processing section 520 form the operation means. Operation of the operating section 561 and the signal processing section 520 will be described later. The surface plasmon resonance sensor 601 of this embodiment further comprises a display 521 connected to the signal processing sections 520A, 520B, 520C . . . of the measuring units.

Analysis of a sample by the surface plasmon resonance sensor of this embodiment will be described, hereinbelow. As shown in FIG. 34, the laser beam 513 emitted from the laser 514 is converged on the interface 510b of the dielectric block 510 and the metal film 512 by the incident optical system 515. The laser beam 513 reflected in total internal reflection at the interface 510b is detected by the photodetector means 517 after collimated by the collimator lens 516. The components of the reflected laser beam 513 impinge upon different photodiodes 517a, 517b, 517c . . . of the photodetector means 517. The photodetector means 517 outputs a signal representing the intensity distribution of the reflected laser beam 513 as detected by the photodiodes 517a, 517b, 517c . . . to the A/D convertor 560. The A/D convertor 560 digitizes the signal and inputs the digitized signal into the operating section 561. In order to increase resolution, the photodetector means 517 is at a greater distance from the interface 510b in this embodiment as compared with in the fourteenth embodiment.

The operating section 561 takes averages of the outputs of three adjacent photodiodes while shifting three adjacent photodiodes by one photodiode, and then calculates differences between two averages adjacent to each other, and inputs the differences into the signal processing section 562. That is, for instance, the average of the outputs of the photodiodes 517a, 517b and 517c, the average of the outputs of the photodiodes 517b, 517c and 517d, the average of the outputs of the photodiodes 517c, 517d and 517e are first taken, and then the differences between the average of the outputs of the photodiodes 517a, 517b and 517c and the average of the photodiodes 517b, 517c and 517d, and between the average of the outputs of the photodiodes 517b, 517c and 517d and the average of the photodiodes 517c, 517d and 517e are calculated, and then the differences between the averages are input into the signal processing section 562. The differences between the averages mat be taken as differentials I' obtained by differentiating the averages of the outputs of three adjacent photodiodes in the direction in which the photodiodes are arranged.

Figure 35A:
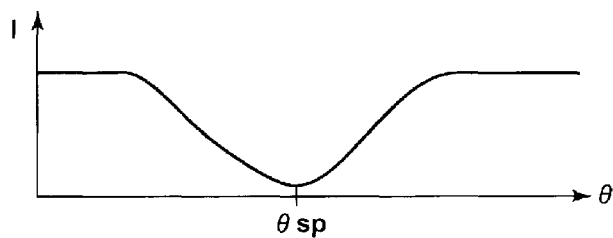
FIG. 35A is a view showing an example of the relation between the intensity I of the component of the laser beam reflected in total internal reflection at the interface and the angle of incidence θ of the component.
Figure 35B:
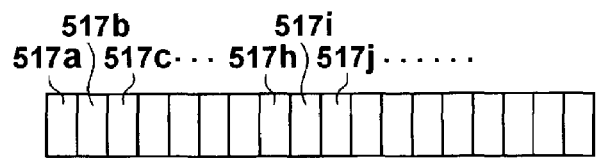
FIG. 35B is a view showing an example of the arrangement of the photodiodes.
Figure 35C:
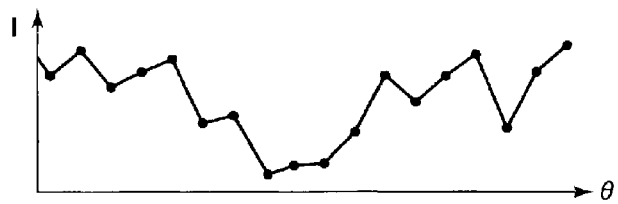
FIG. 35C is a view showing the outputs of the photodiodes when the photodiodes are arranged as shown in FIG. 35B and the relation between the intensity I of the component of the laser beam reflected in total internal reflection at the interface and the angle of incidence θ of the component is as shown in FIG. 35A.
Figure 35D:
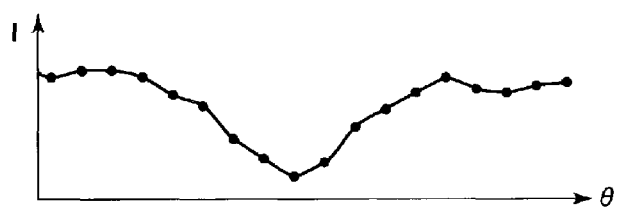
FIG. 35D is a view showing averages of outputs of three adjacent photodiodes.
Figure 35E:
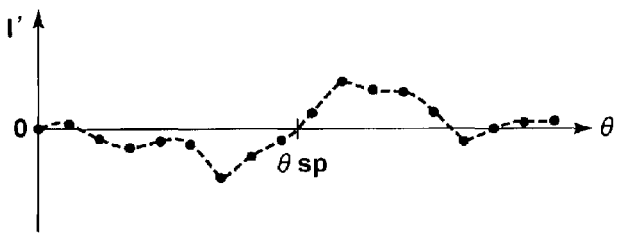
FIG. 35E is a view showing differences of the averages.

FIGS. 35A to 35E are views for illustrating signals processed in the operating section 561. That is, assuming that the relation between the intensity I of the component of the laser beam reflected in total internal reflection at the interface and the angle of incidence θ of the component is as shown in FIG. 35A and the arrangement of the photodiodes 517a, 517b, 517c . . . is as shown in FIG. 35B, the outputs of the photodiodes 517a, 517b, 517c . . . are as shown in FIG. 35C. That is, FIG. 35C shows the signals input into the operating section 561. FIG. 35C shows an example of outputs of the photodiodes 517a, 517b, 517c . . . in the case where the pitches at which the photodiodes 517a, 517b, 517c . . . are arranged is small relatively to the beam profile and the level of signal output from each of the photodiodes 517a, 517b, 517c . . . is low. In such a case, the outputs of the photodiodes 517a, 517b, 517c . . . are apt to be affected by noise and exhibit large fluctuation. FIG. 35D shows averages of the outputs of three adjacent photodiodes while shifting three adjacent photodiodes by one photodiode. In FIG. 35D, the curve is more smooth as compared with that in FIG. 35C since the noise is compensated and resembles the curve in FIG. 35A representing the relation between the intensity I of the component of the laser beam reflected in total internal reflection at the interface and the angle of incidence θ of the component. FIG. 35E shows the differences of the averages, that is, the differentials I' output from the operating section 561.

The signal processing section 562 selects one of the photodiode group whose output I' is the closest to 0 corresponding to the attenuation angle θsp on the basis of the differentials I' input from the operating section 562 (the photodiodes 17h, 17i and 17j in the particular example shown in FIG. 35B), thereby detecting the attenuation angle θsp. Each time a predetermined time lapses, the signal processing section 562 repeatedly calculates the attenuation angle θsp and causes the display 521 to display the amount of change of the attenuation angle θsp from the initiation of the measurement. When the sensing medium 530 which combines with a particular material in the sample liquid 511 is fixed on the metal film 512, the refractive index of the sensing medium 530 changes depending on the state of combination of the sensing medium 530 and the particular material, change of the state of combination of the sensing medium 530 and the particular material can be detected by detecting the amount of change of the attenuation angle θsp.

Though, in the embodiment described above, the attenuation angle θsp is calculated on the basis of differentials I' obtained from averages of the outputs of three photodiodes, the attenuation angle θsp maybe calculated on the basis of differentials I' obtained from averages of the outputs of two adjacent photodiodes or four or more adjacent photodiodes.

In this embodiment, since the attenuation angle θsp is detected on the basis of differentials obtained in the manner described above, in the case where the amount of light detected by each of the photodiodes is insufficient or in the case where small photodetector elements are employed, the attenuation angle θsp can be calculated more accurately at a higher resolution less affected by noise. In place of averages of the outputs of respective photodiodes, sums of the outputs of respective photodiodes may be employed. With this arrangement, levels of signals for differentiation can be enlarged. Further, values obtained by dividing sums of the outputs of respective photodiodes by a certain value or by multiplying the same by a certain value may be employed in place of averages of the outputs of respective photodiodes.

Further, when the operating section 561 outputs averages of three adjacent photodiodes in addition to the differentials and the signal processing section 562 generates a beam profile on the basis of the averages of three adjacent photodiodes, a beam profile can be generated at a high resolution less affected by noise. Also the surface plasmon resonance sensor of the sixteenth embodiment can be modified to a leaky mode sensor by changing a part thereof.

Though, several embodiments of the present invention have been described above, it will be apparent to those skilled in the art that all of or some of the above-described embodiments may be combined in any combination.

What is claimed is:

1. A measuring method utilizing the phenomenon of attenuation in total internal reflection in which a light beam is caused to enter a dielectric block provided on one face thereof with a film layer to be brought into contact with a sample so that total internal reflection conditions are satisfied at the interface of the dielectric block and the film layer and various angles of incidence of the light beam to the interface of the dielectric block and the film layer can be obtained, and the intensity of the light beam reflected in total internal reflection at the interface is detected thereby detecting a state of attenuation in total internal reflection, wherein the improvement comprises the step of causing said light beam to intermittently impinge upon the dielectric block, thereby preventing temperature fluctuation of the dielectric block.

2. A measuring method as defined in claim 1 in which the measurement is started after a lapse of a transient response time from initiation of the light beam impinging upon the dielectric block.

3. A measuring method utilizing the phenomenon of attenuation in total internal reflection in which a light beam is caused to enter a dielectric block provided on its face with a metal film to be brought into contact with a sample so that total internal reflection conditions are satisfied at the interface of the dielectric block and the metal film and various angles of incidence of the light beam to the interface of the dielectric block and the metal film can be obtained, and the intensity of the light beam reflected in total internal reflection at the interface is detected thereby detecting a state of attenuation in total internal reflection involved by surface plasmon resonance, wherein the improvement comprises the step of causing said light beam to intermittently impinge upon the dielectric block, thereby preventing temperature fluctuation of the dielectric block.

4. A measuring method as defined in claim 3 in which the measurement is started after a lapse of a transient response time from initiation of the light beam impinging upon the dielectric block.

5. A measuring method utilizing the phenomenon of attenuation in total internal reflection in which a light beam is caused to enter a dielectric block provided on its face with a clad layer and on the clad layer with an optical waveguide layer to be brought into contact with a sample so that total internal reflection conditions are satisfied at the interface of the dielectric block and the clad layer and various angles of incidence of the light beam to the interface of the dielectric block and the clad layer can be obtained, and the intensity of the light beam reflected in total internal reflection at the interface is detected thereby detecting a state of attenuation in total internal reflection involved by waveguide mode excitation on the optical waveguide layer, wherein the improvement comprises the step of causing said light beam to intermittently impinge upon the dielectric block, thereby preventing temperature fluctuation of the dielectric block.

6. A measuring method as defined in claim 5 in which the measurement is started after a lapse of a transient response time from initiation of the light beam impinging upon the dielectric block.

7. A measuring apparatus utilizing the phenomenon of attenuation in total internal reflection comprising a dielectric block, a film layer which is formed on one face of the dielectric block and is brought into contact with a sample, a light source which emits a light beam, an optical system which causes the light beam to enter the dielectric block so that total internal reflection conditions are satisfied at the interface of the dielectric block and the film layer and various angles of incidence of the light beam to the interface of the dielectric block and the film layer can be obtained, and a photodetector means which detects the intensity of the light beam reflected in total internal reflection at the interface, thereby detecting a state of attenuation in total internal reflection, wherein the improvement comprises an intermittent light beam projecting means which causes said light beam to intermittently impinge upon the dielectric block in order to prevent temperature fluctuations of the dielectric block.

8. A measuring apparatus as defined in claim 7 in which the measurement is started after a lapse of a transient response time from initiation of the light beam impinging upon the dielectric block.

9. A measuring apparatus as defined in claim 7 in which the intermittent light beam projecting means comprises a shutter means which intermittently closes and opens the path of the light beam from the light source to the dielectric block.

10. A measuring apparatus as defined in claim 7 in which the intermittent light beam projecting means comprises an intermittent light source drive means which intermittently drives the light source.

11. A measuring apparatus as defined in claim 10 in which the intermittent light source drive means is provided with a wavelength stabilizing means which stabilizes the wavelength of the light beam emitted from the light source.

12. A measuring apparatus as defined in claim 7 in which the intermittent light projecting means is arranged to cause the light beam to impinge upon the dielectric block so that change of the temperature due to projection of the light beam onto the dielectric block is suppressed to not larger than 0.5° C.

13. A measuring apparatus as defined in claim 12 in which the intermittent light projecting means is arranged to cause the light beam to impinge upon the dielectric block so that change of the temperature due to projection of the light beam onto the dielectric block is suppressed and more preferably to not larger than 0.1° C.

14. A measuring apparatus utilizing the phenomenon of attenuation in total internal reflection comprising a dielectric block, a metal film which is formed on one face of the dielectric block and is brought into contact with a sample, a light source which emits a light beam, an optical system which causes the light beam to enter the dielectric block so that total internal reflection conditions are satisfied at the interface of the dielectric block and the metal film and various angles of incidence of the light beam to the interface of the dielectric block and the metal film can be obtained, and a photodetector means which detects the intensity of the light beam reflected in total internal reflection at the interface, thereby detecting a state of attenuation in total internal reflection, wherein the improvement comprises an intermittent light beam projecting means which causes said light beam to intermittently impinge upon the dielectric block in order to prevent temperature fluctuations of the dielectric block.

15. A measuring apparatus as defined in claim 14 in which the measurement is started after a lapse of a transient response time from initiation of the light beam impinging upon the dielectric block.

16. A measuring apparatus as defined in claim 14 in which the intermittent light beam projecting means comprises a shutter means which intermittently closes and opens the path of the light beam from the light source to the dielectric block.

17. A measuring apparatus as defined in claim 14 in which the intermittent light beam projecting means comprises an intermittent light source drive means which intermittently drives the light source.

18. A measuring apparatus as defined in claim 17 in which the intermittent light source drive means is provided with a wavelength stabilizing means which stabilizes the wavelength of the light beam emitted from the light source.

19. A measuring apparatus as defined in claim 14 in which the intermittent light projecting means is arranged to cause the light beam to impinge upon the dielectric block so that change of the temperature due to projection of the light beam onto the dielectric block is suppressed to not larger than 0.5° C.

20. A measuring apparatus as defined in claim 19 in which the intermittent light projecting means is arranged to cause the light beam to impinge upon the dielectric block so that change of the temperature due to projection of the light beam onto the dielectric block is suppressed and more preferably to not larger than 0.1° C.

21. A measuring apparatus utilizing the phenomenon of attenuation in total internal reflection comprising
a dielectric block,
a clad layer which is formed on one face of the dielectric block,
an optical waveguide layer which is formed on the clad layer and is brought into contact with a sample,
a light source which emits a light beam,
an optical system which causes the light beam to enter the dielectric block so that total internal reflection conditions are satisfied at the interface of the dielectric block and the clad layer and various angles of incidence of the light beam to the interface of the dielectric block and the clad layer can be obtained, and
a photodetector means which detects the intensity of the light beam reflected in total internal reflection at the interface, thereby detecting a state of attenuation in total internal reflection, wherein the improvement comprises
an intermittent light beam projecting means which causes said light beam to intermittently impinge upon the dielectric block in order to prevent temperature fluctuations of the dielectric block.

22. A measuring apparatus as defined in claim 21 in which the measurement is started after a lapse of a transient response time from initiation of the light beam impinging upon the dielectric block.

23. A measuring apparatus as defined in claim 21 in which the intermittent light beam projecting means comprises a shutter means which intermittently closes and opens the path of the light beam from the light source to the dielectric block.

24. A measuring apparatus as defined in claim 21 in which the intermittent light beam projecting means comprises an intermittent light source drive means which intermittently drives the light source.

25. A measuring apparatus as defined in claim 24 in which the intermittent light source drive means is provided with a wavelength stabilizing means which stabilizes the wavelength of the light beam emitted from the light source.

26. A measuring apparatus as defined in claim 21 in which the intermittent light projecting means is arranged to cause the light beam to impinge upon the dielectric block so that change of the temperature due to projection of the light beam onto the dielectric block is suppressed to not larger than 0.5° C.

27. A measuring apparatus as defined in claim 26 in which the intermittent light projecting means is arranged to cause the light beam to impinge upon the dielectric block so that change of the temperature due to projection of the light beam onto the dielectric block is suppressed and more preferably to not larger than 0.1° C.

28. A measuring apparatus comprising
a dielectric block,
a film layer which is formed on one face of the dielectric block and is brought into contact with a sample,
a light source which emits a light beam,
an optical system which causes the light beam to enter the dielectric block at various angles of incidence such that total internal reflection conditions are satisfied at the interface of the dielectric block and the film layer, and
a photodetector means which detects the intensity of the light beam reflected in total internal reflection at the interface, wherein the improvement comprises
a relative movement means which moves the optical system and the dielectric block relatively to each other so that the position in which the light beam impinges upon the interface changes, and
an operation means which statistically processes a plurality of pieces of data, which are output from the photodetector means when the optical system and the dielectric block are in different positions relatively to each other and represent the intensities of the light beam reflected in the different positions of the interface, and obtains data representative of the intensities of the light beam reflected at the interface.

29. A measuring apparatus as defined in claim 28 in which the operation means is a means which takes a median of the plurality of pieces of data as the data representative of the intensities of the light beam reflected at the interface.

30. A measuring apparatus as defined in claim 28 in which the operation means is a means which takes a median of the plurality of pieces of data and obtains an average of the data included in a range of a predetermined width including the median as the data representative of the intensities of the light beam reflected at the interface.

31. A measuring apparatus as defined in claim 28 in which the operation means is a means which takes an average of the plurality of pieces of data minus the maximum value and the minimum value as the data representative of the intensities of the light beam reflected at the interface.

32. A measuring apparatus comprising
a dielectric block,
a metal film which is formed on one face of the dielectric block and is brought into contact with a sample,
a light source which emits a light beam,
an optical system which causes the light beam to enter the dielectric block at various angles of incidence such that total internal reflection conditions are satisfied at the interface of the dielectric block and the metal film, and
a photodetector means which detects the intensity of the light beam reflected in total internal reflection at the interface, wherein the improvement comprises
a relative movement means which moves the optical system and the dielectric block relatively to each other so that the position in which the light beam impinges upon the interface changes, and
an operation means which statistically processes a plurality of pieces of data, which are output from the photodetector means when the optical system and the dielectric block are in different positions relatively to each other and represent the intensities of the light beam reflected in the different positions of the interface, and obtains data representative of the intensities of the light beam reflected at the interface.

33. A measuring apparatus as defined in claim 32 in which the operation means is a means which takes a median of the plurality of pieces of data as the data representative of the intensities of the light beam reflected at the interface.

34. A measuring apparatus as defined in claim 32 in which the operation means is a means which takes a median of the plurality of pieces of data and obtains an average of the data included in a range of a predetermined width including the median as the data representative of the intensities of the light beam reflected at the interface.

35. A measuring apparatus as defined in claim 32 in which the operation means is a means which takes an average of the plurality of pieces of data minus the maximum value and the minimum value as the data representative of the intensities of the light beam reflected at the interface.

36. A measuring apparatus comprising
a dielectric block,
a film layer consisting of a clad layer formed on one face of the dielectric block and an optical waveguide layer which is formed on the clad layer and is brought into contact with a sample,
a light source which emits a light beam,
an optical system which causes the light beam to enter the dielectric block at various angles of incidence such that total internal reflection conditions are satisfied at the interface of the dielectric block and the clad layer, and
a photodetector means which detects the intensity of the light beam reflected in total internal reflection at the interface, wherein the improvement comprises
a relative movement means which moves the optical system and the dielectric block relatively to each other so that the position in which the light beam impinges upon the interface changes, and
an operation means which statistically processes a plurality of pieces of data, which are output from the photodetector means when the optical system and the dielectric block are in different positions relatively to each other and represent the intensities of the light beam reflected in the different positions of the interface, and obtains data representative of the intensities of the light beam reflected at the interface.

37. A measuring apparatus as defined in claim 36 in which the operation means is a means which takes a median of the plurality of pieces of data as the data representative of the intensities of the light beam reflected at the interface.

38. A measuring apparatus as defined in claim 36 in which the operation means is a means which takes a median of the plurality of pieces of data and obtains an average of the data included in a range of a predetermined width including the median as the data representative of the intensities of the light beam reflected at the interface.

39. A measuring apparatus as defined in claim 36 in which the operation means is a means which takes an average of the plurality of pieces of data minus the maximum value and the minimum value as the data representative of the intensities of the light beam reflected at the interface.

40. A measuring apparatus comprising
a dielectric block,
a film layer which is formed on one face of the dielectric block and is brought into contact with a sample,
a light source which emits a light beam,
an optical system which causes the light beam to enter the dielectric block at various angles of incidence such that total internal reflection conditions are satisfied at the interface of the dielectric block and the film layer, and
a photodetector means which detects the intensity of the light beam reflected in total internal reflection at the interface,
wherein the improvement comprises that the optical system is arranged to be able to cause the light beam to simultaneously impinge upon the interface in a plurality of different positions, and
an operation means which statistically processes a plurality of pieces of data, which are output from the photodetector means when the optical system and the dielectric block are in different positions relatively to each other and represent the intensities of the light beam reflected in the different positions of the interface, and obtains data representative of the intensities of the light beam reflected at the interface.

41. A measuring apparatus as defined in claim 40 in which the optical system is an optical system which splits a light beam into a plurality of light beams and causes the light beams to impinge upon the interface in different positions.

42. A measuring apparatus as defined in claim 40 in which the optical system is an optical system which deflects a light beam to impinge upon the interface in different positions.

43. A measuring apparatus as defined in claim 42 in which the operation means is a means which takes a median of the plurality of pieces of data as the data representative of the intensities of the light beam reflected at the interface.

44. A measuring apparatus as defined in claim 42 in which the operation means is a means which takes a median of the plurality of pieces of data and obtains an average of the data included in a range of a predetermined width including the median as the data representative of the intensities of the light beam reflected at the interface.

45. A measuring apparatus as defined in claim 42 in which the operation means is a means which takes an average of the plurality of pieces of data minus the maximum value and the minimum value as the data representative of the intensities of the light beam reflected at the interface.

46. A measuring apparatus comprising
a dielectric block,
a metal film which is formed on one face of the dielectric block and is brought into contact with a sample,
a light source which emits a light beam,
an optical system which causes the light beam to enter the dielectric block at various angles of incidence such that total internal reflection conditions are satisfied at the interface of the dielectric block and the metal film, and
a photodetector means which detects the intensity of the light beam reflected in total internal reflection at the interface, wherein the improvement comprises that
the optical system is arranged to be able to cause the light beam to simultaneously impinge upon the interface in a plurality of different positions, and
an operation means which statistically processes a plurality of pieces of data, which are output from the photodetector means when the optical system and the dielectric block are in different positions relatively to each other and represent the intensities of the light beam reflected in the different positions of the interface, and obtains data representative of the intensities of the light beam reflected at the interface.

47. A measuring apparatus as defined in claim 46 in which the optical system is an optical system which splits a light beam into a plurality of light beams and causes the light beams to impinge upon the interface in different positions.

48. A measuring apparatus as defined in claim 46 in which the optical system is an optical system which deflects a light beam to impinge upon the interface in different positions.

49. A measuring apparatus as defined in claim 46 in which the operation means is a means which takes a median of the plurality of pieces of data as the data representative of the intensities of the light beam reflected at the interface.

50. A measuring apparatus as defined in claim 46 in which the operation means is a means which takes a median of the plurality of pieces of data and obtains an average of the data included in a range of a predetermined width including the median as the data representative of the intensities of the light beam reflected at the interface.

51. A measuring apparatus as defined in claim 46 in which the operation means is a means which takes an average of the plurality of pieces of data minus the maximum value and the minimum value as the data representative of the intensities of the light beam reflected at the interface.

52. A measuring apparatus comprising
a dielectric block,
a film layer consisting of a clad layer formed on one face of the dielectric block and an optical waveguide layer which is formed on the clad layer and is brought into contact with a sample,
a light source which emits a light beam,
an optical system which causes the light beam to enter the dielectric block at various angles of incidence such that total internal reflection conditions are satisfied at the interface of the dielectric block and the clad layer, and
a photodetector means which detects the intensity of the light beam reflected in total internal reflection at the interface, wherein the improvement comprises that
the optical system is arranged to be able to cause the light beam to simultaneously impinge upon the interface in a plurality of different positions, and
an operation means which statistically processes a plurality of pieces of data, which are output from the photodetector means when the optical system and the dielectric block are in different positions relatively to each other and represent the intensities of the light beam reflected in the different positions of the interface, and obtains data representative of the intensities of the light beam reflected at the interface.

53. A measuring apparatus as defined in claim 52 in which the optical system is an optical system which splits a light beam into a plurality of light beams and causes the light beams to impinge upon the interface in different positions.

54. A measuring apparatus as defined in claim 52 in which the optical system is an optical system which deflects a light beam to impinge upon the interface in different positions.

55. A measuring apparatus as defined in claim 52 in which the operation means is a means which takes a median of the plurality of pieces of data as the data representative of the intensities of the light beam reflected at the interface.

56. A measuring apparatus as defined in claim 52 in which the operation means is a means which takes a median of the plurality of pieces of data and obtains an average of the data included in a range of a predetermined width including the median as the data representative of the intensities of the light beam reflected at the interface.

57. A measuring apparatus as defined in claim 52 in which the operation means is a means which takes an average of the plurality of pieces of data minus the maximum value and the minimum value as the data representative of the intensities of the light beam reflected at the interface.

58. A measuring method for analyzing a sample by the use of a measuring apparatus comprising
a measuring chip consisting of a dielectric block, a film layer formed on one face of the dielectric block and a sample holding system which holds the sample on the surface of the film layer,
a light source which emits a light beam,
an optical system which causes the light beam to enter the dielectric block at an angle of incidence such that total internal reflection conditions are satisfied at the interface of the dielectric block and the film layer, and
a photodetector means which comprises a plurality of photodetector elements and detects the intensity of the light beam reflected in total internal reflection at the interface, wherein the improvement comprises the steps of
measuring the intensity of the light beam reflected in total internal reflection at the interface a plurality of times in a time series, smoothing a plurality of pieces of measured data obtained and analyzing the sample on the basis of the smoothed pieces of measured data.

59. A measuring apparatus comprising
a measuring chip consisting of a dielectric block, a film layer formed on one face of the dielectric block and a sample holding system which holds the sample on the surface of the film layer,
a light source which emits a light beam,
an optical system which causes the light beam to enter the dielectric block at an angle of incidence such that total internal reflection conditions are satisfied at the interface of the dielectric block and the film layer, and
a photodetector means which comprises a plurality of photodetector elements and detects the intensity of the light beam reflected in total internal reflection at the interface, wherein the improvement comprises
a smoothing means which smoothes a plurality of pieces of measured data obtained by measuring the intensity of the light beam reflected in total internal reflection at the interface a plurality of times in a time series.

60. A measuring method for analyzing a sample by the use of a measuring apparatus comprising
a measuring chip consisting of a dielectric block, a film layer formed on one face of the dielectric block and a sample holding system which holds the sample on the surface of the film layer,
a light source which emits a light beam,
an optical system which causes the light beam to enter the dielectric block at an angle of incidence such that total internal reflection conditions are satisfied at the interface of the dielectric block and the film layer, and
a photodetector means which comprises a plurality of photodetector elements and detects the intensity of the light beam reflected in total internal reflection at the interface, wherein the improvement comprises the steps of
dividing the plurality of photodetector elements into a plurality of groups,
differentiating the sums of the outputs of the photodetector elements in adjacent two groups in the direction in which the photodetector elements are arranged and
analyzing the sample by obtaining an angle of reflection at which the intensity of the light reflected at the interface takes an absolute minimum on the basis of the differentials.

61. A measuring method for analyzing a sample by the use of a measuring apparatus comprising
a measuring chip consisting of a dielectric block, a film layer formed on one face of the dielectric block and a sample holding system which holds the sample on the surface of the film layer,
a light source which emits a light beam,
an optical system which causes the light beam to enter the dielectric block at an angle of incidence such that total internal reflection conditions are satisfied at the interface of the dielectric block and the film layer, and
a photodetector means which comprises a plurality of photodetector elements and detects the intensity of the light beam reflected in total internal reflection at the interface, wherein the improvement comprises the steps of
calculating averages of outputs of a predetermined number of adjacent photodetector elements in sequence in the direction in which the photodetector elements are arranged, differentiating the averages in the direction in which the photodetector elements are arranged and analyzing the sample by obtaining an angle of reflection at which the intensity of the light reflected at the interface takes an absolute minimum on the basis of the differentials.

62. A measuring apparatus comprising
a measuring chip consisting of a dielectric block, a film layer formed on one face of the dielectric block and a sample holding system which holds the sample on the surface of the film layer,
a light source which emits a light beam,
an optical system which causes the light beam to enter the dielectric block at an angle of incidence such that total internal reflection conditions are satisfied at the interface of the dielectric block and the film layer, and
a photodetector means which comprises a plurality of photodetector elements and detects the intensity of the light beam reflected in total internal reflection at the interface, wherein the improvement comprises,
an operation means which divides the plurality of photodetector elements into a plurality of groups, differentiates the sums of the outputs of the photodetector elements in adjacent two groups in the direction in which the photodetector elements are arranged and obtains an angle of reflection at which the intensity of the light reflected at the interface takes an absolute minimum on the basis of the differentials.

63. A measuring apparatus comprising
a measuring chip consisting of a dielectric block, a film layer formed on one face of the dielectric block and a sample holding system which holds the sample on the surface of the film layer,
a light source which emits a light beam,
an optical system which causes the light beam to enter the dielectric block at an angle of incidence such that total internal reflection conditions are satisfied at the interface of the dielectric block and the film layer, and
a photodetector means which comprises a plurality of photodetector elements and detects the intensity of the light beam reflected in total internal reflection at the interface, wherein the improvement comprises
an operation means which calculates averages of outputs of a predetermined number of adjacent photodetector elements in sequence in the direction in which the photodetector elements are arranged, differentiates the averages in the direction in which the photodetector elements are arranged and obtains an angle of reflection at which the intensity of the light reflected at the interface takes an absolute minimum on the basis of the differentials.

64. A measuring method for analyzing a sample by the use of a measuring apparatus comprising
a measuring chip consisting of a dielectric block, a film layer formed on one face of the dielectric block and a sample holding system which holds the sample on the surface of the film layer,
a light source which emits a light beam,
an optical system which causes the light beam to enter the dielectric block at an angle of incidence such that total internal reflection conditions are satisfied at the interface of the dielectric block and the film layer, and
a photodetector means which comprises a plurality of photodetector elements and detects the intensity of the light beam reflected in total internal reflection at the interface, wherein the improvement comprises the steps of
while causing said light beam to intermittently impinge upon the dielectric block, moving the optical system and the dielectric block relatively to each other so that the position in which the light beam impinges upon the interface changes, measuring the intensity of the light beam reflected in total internal reflection in each position of the interface a plurality of times in a time series by dividing the plurality of photodetector elements into a plurality of groups and differentiating the sums of the outputs of the photodetector elements in adjacent two groups in the direction in which the photodetector elements are arranged, smoothing a plurality of pieces of measured data obtained for each position of the interface thereby obtaining a piece of smoothed data for each position, statistically processing a plurality of pieces of smoothed data for different positions of the interface and obtaining data representative of the intensities of the light beam reflected at the interface.

65. A measuring method for analyzing a sample by the use of a measuring apparatus comprising
a measuring chip consisting of a dielectric block, a film layer formed on one face of the dielectric block and a sample holding system which holds the sample on the surface of the film layer,
a light source which emits a light beam,
an optical system which causes the light beam to enter the dielectric block at an angle of incidence such that total internal reflection conditions are satisfied at the interface of the dielectric block and the film layer, and
a photodetector means which comprises a plurality of photodetector elements and detects the intensity of the light beam reflected in total internal reflection at the interface, wherein the improvement comprises the steps of
while causing said light beam to intermittently impinge upon the dielectric block, moving the optical system and the dielectric block relatively to each other so that the position in which the light beam impinges upon the interface changes, measuring the intensity of the light beam reflected in total internal reflection in each position of the interface a plurality of times in a time series by calculating averages of outputs of a predetermined number of adjacent photodetector elements in sequence in the direction in which the photodetector elements are arranged and differentiating the averages in the direction in which the photodetector elements are arranged, smoothing a plurality of pieces of measured data obtained for each position of the interface thereby obtaining a piece of smoothed data for each position, statistically processing a plurality of pieces of smoothed data for different positions of the interface and obtaining data representative of the intensities of the light beam reflected at the interface.

66. A measuring method for analyzing a sample by the use of a measuring apparatus comprising
a measuring chip consisting of a dielectric block, a film layer formed on one face of the dielectric block and a sample holding system which holds the sample on the surface of the film layer,
a light source which emits a light beam,
an optical system which causes the light beam to enter the dielectric block at an angle of incidence such that total internal reflection conditions are satisfied at the interface of the dielectric block and the film layer, and
a photodetector means which comprises a plurality of photodetector elements and detects the intensity of the light beam reflected in total internal reflection at the interface, wherein the improvement comprises the steps of while causing said light beam to intermittently impinge upon the dielectric block, arranging the optical system to be able to cause the light beam to impinge upon the interface in a plurality of different positions, measuring the intensity of the light beam reflected in total internal reflection in each position of the interface a plurality of times in a time series by dividing the plurality of photodetector elements into a plurality of groups and differentiating the sums of the outputs of the photodetector elements in adjacent two groups in the direction in which the photodetector elements are arranged, smoothing a plurality of pieces of measured data obtained for each position of the interface thereby obtaining a piece of smoothed data for each position, statistically processing a plurality of pieces of smoothed data for different positions of the interface and obtaining data representative of the intensities of the light beam reflected at the interface.

67. A measuring method for analyzing a sample by the use of a measuring apparatus comprising
a measuring chip consisting of a dielectric block, a film layer formed on one face of the dielectric block and a sample holding system which holds the sample on the surface of the film layer,
a light source which emits a light beam,
an optical system which causes the light beam to enter the dielectric block at an angle of incidence such that total internal reflection conditions are satisfied at the interface of the dielectric block and the film layer, and
a photodetector means which comprises a plurality of photodetector elements and detects the intensity of the light beam reflected in total internal reflection at the interface, wherein the improvement comprises the steps of
while causing said light beam to intermittently impinge upon the dielectric block, arranging the optical system to be able to cause the light beam to impinge upon the interface in a plurality of different positions, measuring the intensity of the light beam reflected in total internal reflection in each position of the interface a plurality of times in a time series by calculating averages of outputs of a predetermined number of adjacent photodetector elements in sequence in the direction in which the photodetector elements are arranged and differentiating the averages in the direction in which the photodetector elements are arranged, smoothing a plurality of pieces of measured data obtained for each position of the interface thereby obtaining a piece of smoothed data for each position, statistically processing a plurality of pieces of smoothed data for different positions of the interface and obtaining data representative of the intensities of the light beam reflected at the interface.

68. A measuring apparatus utilizing the phenomenon of attenuation in total internal reflection comprising
a measuring chip consisting of a dielectric block, a film layer formed on one face of the dielectric block and a sample holding system which holds the sample on the surface of the film layer,
a light source which emits a light beam,
an optical system which causes the light beam to enter the dielectric block at an angle of incidence such that total internal reflection conditions are satisfied at the interface of the dielectric block and the film layer,
a photodetector means which comprises a plurality of photodetector elements and detects the intensity of the light beam reflected in total internal reflection at the interface,
an intermittent light beam projecting means which causes said light beam to intermittently impinge upon the dielectric block,
a relative movement means which moves the optical system and the dielectric block relatively to each other so that the position in which the light beam impinges upon the interface changes, and
an operation means which measures the intensity of the light beam reflected in total internal reflection in each position of the interface a plurality of times in a time series by dividing the plurality of photodetector elements into a plurality of groups and differentiating the sums of the outputs of the photodetector elements in adjacent two groups in the direction in which the photodetector elements are arranged, smoothes a plurality of pieces of measured data obtained for each position of the interface thereby obtaining a piece of smoothed data for each position, statistically processes a plurality of pieces of smoothed data for different positions of the interface and obtains data representative of the intensities of the light beam reflected at the interface.

69. A measuring apparatus utilizing the phenomenon of attenuation in total internal reflection comprising
a measuring chip consisting of a dielectric block, a film layer formed on one face of the dielectric block and a sample holding system which holds the sample on the surface of the film layer,
a light source which emits a light beam,
an optical system which causes the light beam to enter the dielectric block at an angle of incidence such that total internal reflection conditions are satisfied at the interface of the dielectric block and the film layer,
a photodetector means which comprises a plurality of photodetector elements and detects the intensity of the light beam reflected in total internal reflection at the interface,
an intermittent light beam projecting means which causes said light beam to intermittently impinge upon the dielectric block,
a relative movement means which moves the optical system and the dielectric block relatively to each other so that the position in which the light beam impinges upon the interface changes, and
an operation means which measures the intensity of the light beam reflected in total internal reflection in each position of the interface a plurality of times in a time series by calculating averages of outputs of a predetermined number of adjacent photodetector elements in sequence in the direction in which the photodetector elements are arranged and differentiating the averages in the direction in which the photodetector elements are arranged, smoothes a plurality of pieces of measured data obtained for each position of the interface thereby obtaining a piece of smoothed data for each position, statistically processes a plurality of pieces of smoothed data for different positions of the interface and obtains data representative of the intensities of the light beam reflected at the interface.

70. A measuring apparatus utilizing the phenomenon of attenuation in total internal reflection comprising
a measuring chip consisting of a dielectric block, a film layer formed on one face of the dielectric block and a sample holding system which holds the sample on the surface of the film layer,
a light source which emits a light beam, an optical system which causes the light beam to enter the dielectric block at an angle of incidence such that total internal reflection conditions are satisfied at the interface of the dielectric block and the film layer, and is arranged to be able to cause the light beam to impinge upon the interface in a plurality of different positions, a photodetector means which comprises a plurality of photodetector elements and detects the intensity of the light beam reflected in total internal reflection at the interface, an intermittent light beam projecting means which causes said light beam to intermittently impinge upon the dielectric block, and an operation means which measures the intensity of the light beam reflected in total internal reflection in each position of the interface a plurality of times in a time series by dividing the plurality of photodetector elements into a plurality of groups and differentiating the sums of the outputs of the photodetector elements in adjacent two groups in the direction in which the photodetector elements are arranged, smoothes a plurality of pieces of measured data obtained for each position of the interface thereby obtaining a piece of smoothed data for each position, statistically processes a plurality of pieces of smoothed data for different positions of the interface and obtains data representative of the intensities of the light beam reflected at the interface.

71. A measuring apparatus utilizing the phenomenon of attenuation in total internal reflection comprising a measuring chip consisting of a dielectric block, a film layer formed on one face of the dielectric block and a sample holding system which holds the sample on the surface of the film layer, a light source which emits a light beam, an optical system which causes the light beam to enter the dielectric block at an angle of incidence such that total internal reflection conditions are satisfied at the interface of the dielectric block and the film layer, and is arranged to be able to cause the light beam to impinge upon the interface in a plurality of different positions, a photodetector means which comprises a plurality of photodetector elements and detects the intensity of the light beam reflected in total internal reflection at the interface, an intermittent light beam projecting means which causes said light beam to intermittently impinge upon the dielectric block, and an operation means which measures the intensity of the light beam reflected in total internal reflection in each position of the interface a plurality of times in a time series by calculating averages of outputs of a predetermined number of adjacent photodetector elements in sequence in the direction in which the photodetector elements are arranged and differentiating the averages in the direction in which the photodetector elements are arranged, smoothes a plurality of pieces of measured data obtained for each position of the interface thereby obtaining a piece of smoothed data for each position, statistically processes a plurality of pieces of smoothed data for different positions of the interface and obtains data representative of the intensities of the light beam reflected at the interface.

72. A measuring apparatus utilizing the phenomenon of attenuation in total internal reflection comprising a dielectric block, a film layer which is formed on one face of the dielectric block and is brought into contact with a sample, a light source which emits a light beam, an optical system which causes the light beam to enter the dielectric block so that total internal reflection conditions are satisfied at the interface of the dielectric block and the film layer and various angles of incidence of the light beam to the interface of the dielectric block and the film layer can be obtained, a photodetector means which detects the intensity of the light beam reflected in total internal reflection at the interface, thereby detecting a state of attenuation in total internal reflection, and a light beam projecting unit which controls said light beam to intermittently impinge upon said dielectric block in order to control temperature fluctuations in said dielectric block.

73. The apparatus of claim 72, wherein the film layer is a metal layer.

74. The apparatus of claim 72, wherein a predetermined time period is used to control the intermittent impingement of the light beam on the dielectric block.

75. The apparatus of claim 73, wherein a predetermined time period is used to control the intermittent impingement of the light beam on the dielectric block.

76. A measuring apparatus utilizing the phenomenon of attenuation in total internal reflection comprising a dielectric block, a clad layer which is formed on one face of the dielectric block, an optical waveguide layer which is formed on the clad layer and is brought into contact with a sample, a light source which emits a light beam, an optical system which causes the light beam to enter the dielectric block so that total internal reflection conditions are satisfied at the interface of the dielectric block and the clad layer and various angles of incidence of the light beam to the interface of the dielectric block and the clad layer can be obtained, a photodetector means which detects the intensity of the light beam reflected in total internal reflection at the interface, thereby detecting a state of attenuation in total internal reflection, and a light beam projecting unit which controls said light beam to intermittently impinge upon said dielectric block in order to control temperature fluctuations in said dielectric block.

77. The apparatus of claim 76, wherein a predetermined time period is used to control the intermittent impingement of the light beam on the dielectric block.

78. The measuring apparatus as defined in claim 7, wherein the intensity of the light beam reflected in total internal reflection at the interface of the dielectric block and the film layer, which is in contact with the sample, is measured a plurality of times in a time series.

79. The measuring apparatus as defined in claim 14, wherein the intensity of the light beam reflected in total internal reflection at the interface of the dielectric block and the film layer, which is in contact with the sample, is measured a plurality of times in a time series.

80. The measuring apparatus as defined in claim 21, wherein the intensity of the light beam reflected in total internal reflection at the interface of the dielectric block and the film layer, which is in contact with the sample, is measured a plurality of times in a time series.

* * * * *